US009975999B2

(12) United States Patent
Tamura et al.

(10) Patent No.: US 9,975,999 B2
(45) Date of Patent: May 22, 2018

(54) LIQUID ORGANOPOLYSILOXANE AND USES THEREOF

(71) Applicant: Dow Corning Toray Co., Ltd., Tokyo (JP)

(72) Inventors: Seiki Tamura, Ichihara (JP); Tatsuo Souda, Ichihara (JP); Tomohiro Iimura, Ichihara (JP); Sayuri Sawayama, Ichihara (JP); Seiji Hori, Ichihara (JP); Haruhiko Furukawa, Ichihara (JP)

(73) Assignee: DOW CORNING TORAY CO., LTD., Tokyo (JP)

( * ) Notice: Subject to any disclaimer, the term of this patent is extended or adjusted under 35 U.S.C. 154(b) by 918 days.

(21) Appl. No.: 14/369,423

(22) PCT Filed: Dec. 25, 2012

(86) PCT No.: PCT/JP2012/084317
§ 371 (c)(1),
(2) Date: Jun. 27, 2014

(87) PCT Pub. No.: WO2013/100207
PCT Pub. Date: Jul. 4, 2013

(65) Prior Publication Data
US 2014/0364394 A1 Dec. 11, 2014

(30) Foreign Application Priority Data
Dec. 27, 2011 (JP) ................ 2011-286976

(51) Int. Cl.
| C08G 77/38 | (2006.01) |
| C08G 77/12 | (2006.01) |
| C08G 77/50 | (2006.01) |
| A61Q 1/02 | (2006.01) |
| A61Q 1/10 | (2006.01) |
| A61Q 5/02 | (2006.01) |
| A61Q 5/04 | (2006.01) |
| A61Q 5/10 | (2006.01) |
| A61Q 5/12 | (2006.01) |
| A61Q 15/00 | (2006.01) |
| A61Q 19/00 | (2006.01) |
| A61K 8/893 | (2006.01) |
| A61K 8/92 | (2006.01) |

(52) U.S. Cl.
CPC .............. *C08G 77/38* (2013.01); *A61K 8/893* (2013.01); *A61K 8/92* (2013.01); *A61Q 1/02* (2013.01); *A61Q 1/10* (2013.01); *A61Q 5/02* (2013.01); *A61Q 5/04* (2013.01); *A61Q 5/10* (2013.01); *A61Q 5/12* (2013.01); *A61Q 15/00* (2013.01); *A61Q 19/00* (2013.01); *C08G 77/50* (2013.01); *C08G 77/12* (2013.01)

(58) Field of Classification Search
CPC ......... C08G 77/12; C08G 77/38; C08G 77/50
See application file for complete search history.

(56) References Cited

U.S. PATENT DOCUMENTS

| 4,431,789 A | 2/1984 | Okazaki et al. |
| 4,515,979 A | 5/1985 | Otsuki et al. |
| 4,689,383 A | 8/1987 | Riffle et al. |
| 4,853,474 A | 8/1989 | Bahr et al. |
| 4,908,228 A | 3/1990 | Lo |
| 5,136,068 A | 8/1992 | Bahr et al. |
| 5,225,509 A | 7/1993 | Heinrich et al. |
| 5,288,831 A | 2/1994 | Ichinohe et al. |
| 5,387,417 A | 2/1995 | Rentsch |
| 5,397,367 A | 3/1995 | Fey et al. |
| 5,625,024 A | 4/1997 | Schlitte et al. |
| 5,654,362 A | 8/1997 | Schulz, Jr. et al. |
| 5,981,680 A | 11/1999 | Petroff et al. |
| 6,353,076 B1 | 3/2002 | Barr et al. |
| 6,605,183 B1 | 8/2003 | Rautschek et al. |
| 6,784,271 B2 | 8/2004 | Nakanishi |
| 7,105,581 B2 | 9/2006 | Burger et al. |
| 7,378,482 B2 | 5/2008 | Asch et al. |
| 7,429,636 B2 | 9/2008 | Asch et al. |
| 7,432,338 B2 | 10/2008 | Chapman et al. |
| 7,449,536 B2 | 11/2008 | Chapman et al. |
| 7,482,419 B2 | 1/2009 | Caprasse et al. |
| 7,645,360 B2 | 1/2010 | Burger et al. |
| 7,709,671 B2 | 5/2010 | Nishijima et al. |
| 7,771,709 B2 | 8/2010 | Nakanishi et al. |
| 2002/0131947 A1 | 9/2002 | Nakanishi |
| 2005/0261133 A1* | 11/2005 | Nakanishi ............ C08G 77/045 504/358 |

(Continued)

FOREIGN PATENT DOCUMENTS

| CA | 2 139 057 A1 | 6/1995 |
| EP | 0 381 318 A2 | 8/1990 |
| JP | S 55-041210 A | 3/1980 |

(Continued)

OTHER PUBLICATIONS

International Search Report for Application No. PCT/JP2012/084317 dated May 28, 2013, 3 pages.
English language abstract for JPS 55-041210 extracted from PAJ database on Aug. 27, 2014, 1 page.
English language abstract for JPS 57-149290 extracted from espacenet.com database on Aug. 27, 2014, 2 pages.
English language abstract for JPS 60-018525 extracted from espacenet.com database on Aug. 27, 2014, 2 pages.
English language abstract for JPS 62-195389 extracted from PAJ database on Aug. 27, 2014, 1 page.
English language abstract for JPS 63-248410 extracted from PAJ database on Aug. 27, 2014, 1 page.

(Continued)

*Primary Examiner* — Joseph R Kosack
(74) *Attorney, Agent, or Firm* — Howard & Howard Attorneys PLLC

(57) ABSTRACT

A liquid organopolysiloxane having fluidity at least 100° C., a silicon-bonded glycerin derivative group, and a cross-linked structure comprising a carbon-silicon bond at the crosslinking portion.

20 Claims, No Drawings

(56) References Cited

U.S. PATENT DOCUMENTS

| | | | |
|---|---|---|---|
| 2011/0015337 | A1 | 1/2011 | Sakuta et al. |
| 2014/0004065 | A1 | 1/2014 | Souda et al. |

FOREIGN PATENT DOCUMENTS

| | | | |
|---|---|---|---|
| JP | S 57-149290 A | 9/1982 | |
| JP | S 60-018525 A | 1/1985 | |
| JP | S 62-195389 A | 8/1987 | |
| JP | S 63-248410 A | 10/1988 | |
| JP | H 02-302438 A | 12/1990 | |
| JP | H 06-089147 B2 | 11/1994 | |
| JP | H 07-185212 A | 7/1995 | |
| JP | H 07-330907 A | 12/1995 | |
| JP | H 08-000908 A | 1/1996 | |
| JP | 2613124 B | 5/1997 | |
| JP | H 09-165315 A | 6/1997 | |
| JP | H 09-165318 A | 6/1997 | |
| JP | 2844453 B | 1/1999 | |
| JP | 2001-115390 A | 4/2001 | |
| JP | 2001-512164 A | 8/2001 | |
| JP | 2002-179798 A | 6/2002 | |
| JP | 3389311 B | 3/2003 | |
| JP | 2004-174495 A | 6/2004 | |
| JP | 2005-042097 A | 2/2005 | |
| JP | 2005-089494 A | 4/2005 | |
| JP | 2005-120293 A | 5/2005 | |
| JP | 2005-523980 A | 8/2005 | |
| JP | 2005-529989 A | 10/2005 | |
| JP | 2005-344076 A | 12/2005 | |
| JP | 2006-511645 A | 4/2006 | |
| JP | 2006-511646 A | 4/2006 | |
| JP | 2006-218472 A | 8/2006 | |
| JP | H 07-292119 A | 10/2006 | |
| JP | 2007-532754 A | 11/2007 | |
| JP | 4009382 B | 11/2007 | |
| JP | 2008-542010 A | 11/2008 | |
| JP | 2009-262080 A | 11/2009 | |
| JP | 4485134 B2 | 6/2010 | |
| WO | WO 02/055588 A1 | 7/2002 | |
| WO | WO 2004/046226 A1 | 6/2004 | |
| WO | WO 2007/109240 A2 | 9/2007 | |
| WO | WO 2009/006091 A2 | 1/2009 | |
| WO | WO 2011/028770 A1 | 3/2011 | |
| WO | WO 2011/136397 A1 | 11/2011 | |

OTHER PUBLICATIONS

English language abstract for JPH 02-302438 extracted from PAJ database on Aug. 27, 2014, 1 page.
English language abstract for JPH 06-089147 extracted from espacenet.com database on Aug. 27, 2014, 2 pages.
English language abstract for JPH 07-185212 extracted from espacenet.com database on Aug. 27, 2014, 1 page.
English language abstract and machine-assisted English translation for JPH 07-330907 extracted from the PAJ database on Aug. 27, 2014, 20 pages.
English language abstract for JPH 08-000908 extracted from espacenet.com database on Aug. 27, 2014, 2 pages.
Machine-assisted English translation for JP 2613124 extracted from the PAJ database on Aug. 27, 2014, 43 pages.
English language abstract and machine-assisted English translation for JPH 09-165315 extracted from the PAJ database on Aug. 27, 2014, 31 pages.
English language abstract and machine-assisted English translation for JPH 09-165318 extracted from the PAJ database on Aug. 27, 2014, 30 pages.
Machine-assisted English translation for JP 2844453 extracted from the PAJ database on Aug. 27, 2014, 36 pages.
English language abstract for JP 2001-115390 extracted from espacenet.com database on Aug. 27, 2014, 2 pages.
English language abstract not found for JP 2001-512164; however, see English language equivalent U.S. Pat. No. 6,353,076. Original document extracted from espacenet.com database on Aug. 27, 2014, 67 pages.
English language abstract for JP 2002-179798 extracted from espacenet.com database on Aug. 27, 2014, 2 pages.
Machine-assisted English translation for JP 3389311 extracted from the PAJ database on Aug. 27, 2014, 42 pages.
English language abstract for JP 2004-174495 extracted from espacenet.com database on Aug. 27, 2014, 2 pages.
English language abstract for JP 2005-042097 extracted from espacenet.com database on Aug. 27, 2014, 2 pages.
English language abstract and machine-assisted English translation for JP 2005-089494 extracted from the PAJ database on Aug. 27, 2014, 30 pages.
English language abstract and machine-assisted English translation for JP 2005-120293 extracted from the PAJ database on Aug. 27, 2014, 82 pages.
English language abstract not found for JP 2005-523980; however, see English language equivalent U.S. Pat. No. 7,429,636. Original document extracted from espacenet.com database on Aug. 27, 2014, 44 pages.
English language abstract not found for JP 2005-529989; however, see English language equivalent U.S. Pat. No. 7,378,482. Original document extracted from espacenet.com database on Aug. 27, 2014, 52 pages.
English language abstract and machine-assisted English translation for JP 2005-344076 extracted from the PAJ database on Aug. 27, 2014, 23 pages.
English language abstract not found for JP 2006-511645; however, see English language equivalent U.S. Pat. No. 7,432,338. Original document extracted from espacenet.com database on Aug. 27, 2014, 33 pages.
English language abstract not found for JP 2006-511646; however, see English language equivalent U.S. Pat. No. 7,449,536. Original document extracted from espacenet.com database on Aug. 27, 2014, 29 pages.
English language abstract and machine-assisted English translation for JP 2006-218472 extracted from the PAJ database on Aug. 27, 2014, 27 pages.
English language abstract not found for JPH 07-292119; however, see English language equivalent U.S. Pat. No. 5,625,024. Original document extracted from espacenet.com database on Aug. 27, 2014, 16 pages.
Machine-assisted English translation for JP 4009382 extracted from the PAJ database on Aug. 27, 2014, 72 pages.
English language abstract not found for JP 2007-532754; however, see English language equivalent U.S. Pat. No. 7,482,419. Original document extracted from espacenet.com database on Aug. 27, 2014, 38 pages.
English language abstract not found for JP 2008-542010; however, see English language equivalent U.S. Pat. No. 7,645,360. Original document extracted from espacenet.com database on Aug. 27, 2014, 22 pages.
English language abstract and machine-assisted English translation for JP 2009-262080 extracted from the PAJ database on Aug. 27, 2014, 41 pages.
English language abstract and machine-assisted English translation for JP 4485134 extracted from the PAJ database on Aug. 27, 2014, 92 pages.
English language abstract for WO 02/055588 extracted from espacenet.com database on Aug. 27, 2014, 2 pages.
English language abstract for WO 2004/046226 extracted from espacenet.com database on Aug. 27, 2014, 2 pages.

* cited by examiner

LIQUID ORGANOPOLYSILOXANE AND USES THEREOF

RELATED APPLICATIONS

This application is the National Stage of International Patent Application No. PCT/JP2012/084317, filed on Dec. 25, 2012, which claims priority to and all the advantages of Japanese Patent Application No. 2011-286976, filed on Dec. 27, 2011, the content of which is incorporated herein by reference.

TECHNICAL FIELD

The present invention relates to a novel liquid organopolysiloxane having a crosslinked structure and uses thereof.

BACKGROUND ART

As a liquid organopolysiloxane having a hydrophilic group and a crosslinking portion, a product obtained by reacting a particular alkylene oxide derivative, a particular silicone derivative, and a particular isocyanate compound has been reported as being excellent as an industrial use anti-foaming agent (see Patent Document 1). However, this material uses an isocyanate, which has high hazardous properties, as a raw material. Therefore, from the perspectives of safety, cost for refinement, and the like, there are obstacles in using such a material.

Additionally, as a liquid organopolysiloxane having a hydrophilic group and a crosslinking portion, an organopolysiloxane-polyoxyalkylene in which at least two organopolysiloxane-polyoxyalkylene molecules are crosslinked using a crosslinking compound free of internal hydrolysable bonds is disclosed. It is also reported that such a liquid organopolysiloxane is useful as an emulsifier (Patent Document 2). A great deal of applied research regarding this material has been conducted and the following technologies have been reported: a polar liquid in nonpolar liquid emulsion (Patent Document 3); a vaseline-containing emulsion free of oily stickiness (Patent Document 4); a hair conditioning composition (Patent Document 5); and a defoaming composition and a silicone anti-foaming composition (Patent Documents 6 and 7).

However, while the material proposed in Patent Document 2 has excellent characteristics for emulsifying/dispersing water in a hydrocarbon oil, ester oil, or similar non-silicone oil, water cannot be stably emulsified/dispersed in a system containing a large amount of silicone oil. Furthermore, when the obtained emulsion is stored for an extended period of time, there is a problem in that the emulsion produces an odor.

On the other hand, a polysiloxane-polyether base copolymer comprising a T unit and random bonded organopolysiloxane units and straight polyether units in which the organopolysiloxane and the polyether units are bonded via Si—O—C or Si—C bonds is disclosed (Patent Document 8). It is reported that such a copolymer has improved characteristics as a lacquer coating additive. However, this material is manufactured according to a method in which a straight alkenyl-containing polyether having a terminal OH group is added via hydrosilylation to an organopolysiloxane having a Si—H group. Then, the remaining Si—H groups and the terminal OH groups of the polyether portion bonded to the siloxane are condensed by dehydrogenation in the presence of a strong base. As a result, disconnecting of the organopolysiloxane portion caused by the strong base occurs easily, and achieving constant quality and performance is difficult. Additionally, because the crosslinked portions contain Si—O—C bonds, there is a problem in that hydrolysis occurs when compounded in a formulation including water, which leads to a gradual decline in effectiveness.

As a hydrolysis resistant liquid organopolysiloxane having a hydrophilic group and a crosslinking portion, a polyether-polysiloxane-copolymer that has alkylene groups having from 2 to 10 carbons at both terminals, and that is crosslinked by a polyether in which a free valence of said group is further bonded to one silicon atom of the copolymer (Patent Document 9); and a branched polyether-polysiloxane-copolymer having a constituent expressed by the general formula: $Y[—C_nH_{2n}—(R_2SiO)_m-A_p-R_2Si-G]_x$ (Patent Document 10) are known. Additionally, a polysiloxane copolymer is disclosed that can be manufactured by reacting an organopolysiloxane having at least one Si—H bond per molecule with a substantially linear compound that is addable via hydrosilylation and, thereafter, further reacting with an organic compound having at least two isocyanate groups per molecule (Patent Document 11). Furthermore, a surfactant comprising a crosslinked body of an active hydrogen-containing modified silicone and a crosslinking agent, wherein the viscosity (at 25° C.) of the crosslinked body is from 500 to 100,000,000 mPa·s is reported (Patent Document 12). However, applicable fields of this material are primarily limited to anti-foaming agents, and use as a cosmetic composition is not reported.

Additionally, as technologies related to a liquid organopolysiloxane having a hydrophilic group and a crosslinking portion, organohydrogen silicon compounds comprising at least one silicon-bonded hydrogen atom and at least one cyclosiloxane ring per molecule; and applications as a curable composition for paper coating are reported (Patent Documents 13 to 16). However, in these citations, there is no recitation about liquid types in which the hydrophilic group is modified or applications in cosmetic composition.

As described above, materials used in the field of cosmetic compositions as liquid organopolysiloxanes having a hydrophilic group and a crosslinking portion are limited to only the organopolysiloxane-polyoxyalkylene recited in Patent Document 2, and there is a need to solve the various problems thereof.

Now, a great deal of research into reducing the odor of polyether modified polysiloxanes that do not have crosslinking portions (polyoxyalkylene group-containing organopolysiloxanes) has been conducted. The first cause of odorization over time of a polyether modified polysiloxane that was reported was the aldehyde and acid produced as a result of oxidation degradation (rancidity) over time of the polyether moiety in the polyether modified polysiloxane composition. Examples of technologies to suppress this oxidation degradation include the methods recited in Patent Documents 17 and 18 in which tocopherol, phytic acid, or a similar anitioxidant component is added to the polyether modified polysiloxane composition.

However, the use of only an anti-oxidizing agent results in the insufficient suppression of the odorization over time of a formulation based on the polyether modified polysiloxane and, as a result, other causes were investigated. As a result, Patent Document 19 recites that propionaldehyde originating from unreacted propenyl-etherified polyoxyalkylene is a cause of the odor.

The polyether modified polysiloxane composition is typically synthesized via a hydrosilylation reaction of an organohydrogenpolysiloxane having a silicon-bonded hydrogen group and a polyoxyalkylene having an allyl ether group at a terminal. Patent Document 19 recites that, in the production of the polyether modified polysiloxane composition, a double bond of the allyl etherified polyoxyalkylene migrates inward due to the influence of a platinum catalyst and a portion of the allyl-etherified polyoxyalkylene becomes a propenyl-etherified polyoxyalkylene and remains in the polyether modified polysiloxane composition as-is without reacting with the organohydrogenpolysiloxane. Patent Document 19 also recites that the propenyl-etherified polyoxyalkylene degrades over time, thus producing ketones and aldehydes which results in the odorization. Moreover, hydrolysis in the presence of an acid is disclosed as a useful deodorization method.

However, while this deodorization method could be thought to be useful if all of the allyl groups of the polyoxyalkylene remaining in the composition were replaced with propenyl groups, in actuality, a significant proportion of the allyl-etherified polyoxyalkylene which is not easily hydrolyzed remains. As a result, the composition cannot be sufficiently deodorized using the deodorization method of Patent Document 19. On the other hand, if a strong acid is used that can hydrolyze the allyl-etherified polyoxyalkylene, the carbon-oxygen bond at the polyoxyalkylene site and/or the silicon-oxygen bond at the polysiloxane site may disconnect, so using such an acid is inappropriate. Additionally, in order to perform the hydrolysis reaction in a quantitative manner, excessive amounts of water and acid are needed. These excessive amounts of water and acid complicate post treatment processes and, therefore, this deodorization method is not preferable.

In order to resolve this problem, methods for suppressing the production of propionaldehyde have been disclosed (Patent Documents 20 to 23). In these methods, a hydrogenation treatment is performed as a deodorization method of the polyether modified polysiloxane composition in order to alkylate the alkenyl groups (double bonds) included in the alkenyl group-containing polyoxyalkylene (including both propenyl-etherified polyoxyalkylene and allyl-etherified polyoxyalkylene) remaining in the composition. However, even with a polyether modified polysiloxane composition deodorized using a hydrogenation reaction, in cases where a formulation including water and an alcohol is compounded, it may be difficult to achieve sufficient deodorization over time or under elevated temperature conditions.

A cause of the odorization is acetal and similar aldehyde condensation products that are free of unsaturated bonds that remain in the composition. Thus, for the purpose of completely eliminating the acetal and other aldehyde condensation products, technology in which treatment using the acid aqueous solution and hydrogenation treatment are combined (Patent Document 24); and technologies in which hydrogenation treatment and treatment using a solid acid catalyst are combined (Patent Documents 25 and 26) are disclosed. The technology recited in Patent Document 24 is applied not only to polyether-modified silicones, but also to glycerin-modified silicones and sugar-modified silicones. That is, it is acknowledged that performing at least hydrogenation treatment is preferable in the deodorization of hydrophilic silicones exemplified by polyether modified polysiloxane, which is a raw material suitable for use in cosmetic products.

On the other hand, Patent Documents 27 to 40 recite technologies related to glycerin-modified silicones that do not have crosslinked portions, and application to these types of cosmetic compositions has been heavily researched. Recently, it has been thought that glycerin-modified silicone was superior to polyether-modified silicone from the perspective of oxidation stability and, thus, glycerin-modified silicone has attracted attention as a surfactant having greater safety. For example, in Germany, a demand for the replacement of raw materials having polyether groups with non-polyether raw materials has increased due to a negative perception of the safety of products comprising polyoxyethylene (PEG) due to testing done by a consumer information magazine company. Moreover, in South Korea, increased interest in non-polyether silicone surfactants has emerged due to a concern that products containing polyoxyethylene (PEG) may irritate the skin because formalin may be produced as a result of oxidation degradation of PEG.

In light of the above, there is a global trend toward changing the entire formulation of end consumer products such as cosmetic products, and the like, to PEG-FREE formulations. In concord with this trend, there is a demand for progression from the old polyether-modified silicone technology to non-polyether hydrophilic silicone in the field of silicone-based surfactants as well. However, conventional glycerin-modified silicone have significant problems in that they do not appear in patent document searches. This is because even if glycerin-modified silicone is used as an emulsifier for a water-in-oil emulsion, it cannot be used in an actual formulation because performance is low. As a result, there is no choice but to use a more reliable polyether-modified silicone emulsifier in combination with the glycerin-modified silicone, which makes it impossible to achieve the goal of shifting all cosmetic compositions to PEG-FREE formulations.

However, a liquid organopolysiloxane having a glycerin derivative group and a crosslinking portion in which the crosslinking portion links the organopolysiloxane portion and the organic portion via a Si—C bond has not been disclosed, and use of the same in cosmetic compositions and external use preparations is not known.

PRIOR ART DOCUMENTS

Patent Documents

Patent Document 1: Japanese Unexamined Patent Application Publication No. S-63-248410A
Patent Document 2: U.S. Pat. No. 4,853,474
Patent Document 3: U.S. Pat. No. 5,136,068
Patent Document 4: U.S. Pat. No. 5,387,417
Patent Document 5: European Patent No. 0381318
Patent Document 6: Japanese Unexamined Patent Application Publication No. H-08-000908
Patent Document 7: Japanese Unexamined Patent Application Publication No. H-07-185212
Patent Document 8: Japanese Unexamined Patent Application Publication No. H-07-292119
Patent Document 9: Japanese Unexamined Patent Application Publication No. 2001-115390A
Patent Document 10: Japanese Unexamined Patent Application Publication No. 2004-174495A
Patent Document 11: Japanese Unexamined Patent Application Publication (Translation of PCT Application) No. 2008-542010A
Patent Document 12: Japanese Unexamined Patent Application Publication No. 2009-262080A
Patent Document 13: Japanese Unexamined Patent Application Publication (Translation of PCT Application) No. 2005-523980A
Patent Document 14: Japanese Unexamined Patent Application Publication (Translation of PCT Application) No. 2005-529989A Patent Document 15: Japanese Unexamined Patent Application Publication (Translation of PCT Application) No. 2006-511645A
Patent Document 16: Japanese Unexamined Patent Application Publication (Translation of PCT Application) No. 2006-511646A
Patent Document 17: Japanese Examined Patent Application Publication No. S-55-041210
Patent Document 18: Japanese Unexamined Patent Application Publication No. S-60-018525A
Patent Document 19: Japanese Unexamined Patent Application Publication No. H-02-302438A
Patent Document 20: U.S. Pat. No. 5,225,509
Patent Document 21: Japanese Unexamined Patent Application Publication No. H-07-330907A
Patent Document 22: Japanese Unexamined Patent Application Publication No. H-09-165315A
Patent Document 23: Japanese Unexamined Patent Application Publication No. H-09-165318A
Patent Document 24: WO2002/055588
Patent Document 25: WO2004/046226
Patent Document 26: Japanese Unexamined Patent Application Publication No. 2005-120293A
Patent Document 27: Japanese Examined Patent Application Publication No. S-62-34039 (Japanese Unexamined Patent Application Publication No. S-57-149290)
Patent Document 28: Japanese Patent No. 2583412 (Japanese Unexamined Patent Application Publication No. S-62-195389)
Patent Document 29: U.S. Pat. No. 4,689,383
Patent Document 30: U.S. Pat. No. 4,908,228
Patent Document 31: Japanese Examined Patent Application Publication No. H-06-089147 (Japanese Patent No. 1956013)
Patent Document 32: Japanese Patent No. 2613124 (Japanese Unexamined Patent Application Publication No. H-04-188795)
Patent Document 33: Japanese Patent No. 2844453 (Japanese Unexamined Patent Application Publication No. H-02-228958)
Patent Document 34: Japanese Patent No. 3389311 (Japanese Unexamined Patent Application Publication No. H-07-238170)
Patent Document 35: Japanese Patent No. 3976226 (Japanese Unexamined Patent Application Publication No. 2002-179798)
Patent Document 36: Japanese Patent No. 4485134 (Japanese Unexamined Patent Application Publication No. 2004-339244)
Patent Document 37: Japanese Unexamined Patent Application Publication No. 2005-042097A
Patent Document 38: Japanese Unexamined Patent Application Publication No. 2005-089494A
Patent Document 39: Japanese Unexamined Patent Application Publication No. 2005-344076A
Patent Document 40: Japanese Unexamined Patent Application Publication No. 2006-218472A

SUMMARY OF INVENTION

Technical Problems

The present invention was developed in order to solve the problems described above. A first object of the present invention is to provide a novel liquid organopolysiloxane and a manufacturing method of the same, in which the novel liquid organopolysiloxane has affinity with various oil agents, and has superior emulsifying characteristics, imparts superior tactile sensation, and, in cases where compounded in an external use preparation or cosmetic composition comprising water and an oil, takes advantage of the effects of water to suppress oiliness and provide a smooth feeling when applying, a well-conforming, natural feeling to the skin, excellent moisturizing effects, a lack of stickiness, and similar superior sensations during use.

A second object of the present invention is to provide a tactile sensation improver, a film-forming agent, a binder, a viscosity adjusting agent, a moisturizing agent, a skin adhesive, a surfactant, an emulsifier, a powder dispersing agent, or a similar raw material including the liquid organopolysiloxane, for use in an external use preparation or a cosmetic composition; and to provide a cosmetic composition or an external use preparation comprising the liquid organopolysiloxane.

Furthermore, a third object of the present invention is to provide an external use preparation or a cosmetic composition having superior emulsion stability that is free of compounds containing polyoxyethylene structures and which, by using the liquid organopolysiloxane as a raw material of the external use preparation or the cosmetic composition, complies with the global trend for changing the entire formulation of end consumer products such as cosmetic products and the like to PEG-FREE formulations.

Solution to Problems

As a result of diligent studies in order to achieve the aforementioned objectives, the inventors of the present invention have completed the present invention. Specifically, the first object of the present invention is achieved by a liquid organopolysiloxane having fluidity at at least 100° C., a silicon-bonded glycerin derivative group, and a crosslinked structure comprising a carbon-silicon bond at the crosslinking portion.

The glycerin derivative group is preferably bonded to a silicon atom via a linking group that is at least divalent and is preferably a glycerin derivative group-containing organic group comprising at least one type of hydrophilic unit selected from hydrophilic units represented by structural formulae (4-1) to (4-3) below.

(4-1)

In this formula, W is a hydrogen atom or an alkyl group having from 1 to 20 carbons.

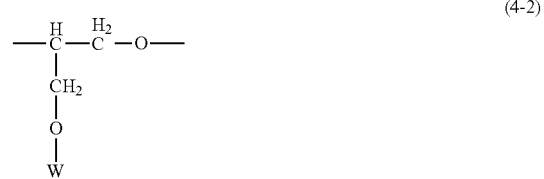
(4-2)

In this formula, W is synonymous with the group described above.

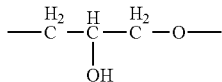 (4-3)

Additionally, the glycerin derivative group is preferably a hydrophilic segment comprising at least one linearly bonded hydrophilic unit selected from the hydrophilic units represented by the structural formulae (4-1) to (4-3) above; or the glycerin derivative group is preferably a glycerin derivative group-containing organic group bonded to the silicon atom via a linking group that is at least divalent, comprising at least one type of hydrophilic unit selected from the hydrophilic units represented by the structural formulae (4-1) to (4-3) above, and a branch unit selected from groups represented by structural formulae (4-4) to (4-6) below.

Additionally, preferably the glycerin derivative group is bonded to the silicon atom via a linking group that is at least divalent, and an average value of the number of repetitions of the hydrophilic unit represented by the structural formulae (4-1) to (4-3) is in a range from 1.1 to 2.9. Particularly, the glycerin derivative group is preferably a diglycerin derivative group-containing organic group expressed by general formula (5-1) below:

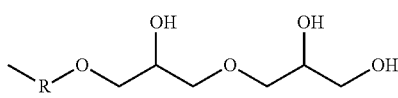 (5-1)

(wherein R is a divalent organic group); or general formula (5-2) below:

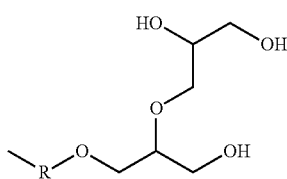 (5-2)

(wherein R is synonymous with that described above).

Furthermore, particularly, the liquid organopolysiloxane of the present invention preferably comprises in the molecule:
a substituted or unsubstituted, straight or branched monovalent hydrocarbon group having from 9 to 60 carbons;
an alkyl group substituted by a chain polysiloxane structure expressed by general formula (4) below:

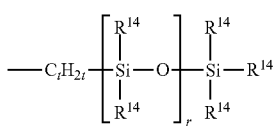 (4)

(wherein $R^{14}$ are each independently substituted or unsubstituted, straight or branched monovalent hydrocarbon groups having from 1 to 30 carbons, hydroxyl groups, or hydrogen atoms and at least one of the $R^{14}$ moieties is the monovalent hydrocarbon group; t is a number in a range from 2 to 10; and r is a number in a range from 1 to 100); and
when expressed as a functional group $L^i$ and i=1, a silylalkyl group having a siloxane dendron structure expressed by general formula (3) below:

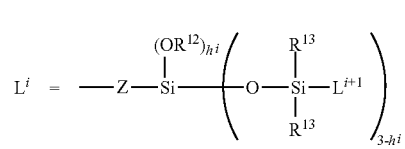 (3)

(wherein $R^{12}$ is a substituted or unsubstituted, straight or branched monovalent hydrocarbon group having from 1 to 30 carbons;
$R^{13}$ are each independently a phenyl group or an alkyl group having from 1 to 6 carbons;
Z is a divalent organic group;
i represents a generation of the aforementioned silylalkyl group represented by $L^i$ and is an integer of 1 to k when k is a number of generations that is a number of repetitions of the silylalkyl group; the number of generations k is an integer from 1 to 10; $L^{i+1}$ is the silylalkyl group when i is less than k, and the $R^{13}$ moiety when i=k; and $h^i$ is a number in a range of 0 to 3).

The liquid organopolysiloxane can be obtained by reacting:
(A) an organohydrogenpolysiloxane;
(B) a glycerin derivative group-containing organic compound having reactive unsaturated group; and
(C) at least one type of organic compound selected from the group consisting of (C1) an organic compound having an average number of reactive unsaturated group in the molecule that is greater than 1 and (C2) an organic compound having not less than one reactive unsaturated group and not less than one epoxy group in the molecule.

An average value of a number of silicon-bonded hydrogen atoms per molecule of the component (A), which reacts with the reactive unsaturated groups of the component (C) constituting the crosslinking portion, is greater than 0.1 and less than 2.0.

The component (A) is preferably expressed by average composition formula (1):

$$R^1{}_aH_bSiO_{(4-a-b)/2} \quad (1)$$

(wherein $R^1$ are each independently monovalent organic groups, $1.0 \leq a \leq 3.0$, and $0.001 \leq b \leq 1.5$).

The component (C) is preferably at least one organic compound selected from (C1-1) to (C1-5) and (C2-1) to (C2-2): (C1-1) an α,ω-diene expressed by general formula (2-1):

 (2-1)

(wherein $1 \leq x \leq 20$);
(C1-2) an α,ω-diyne expressed by general formula (2-2):

 (2-2)

(wherein $1 \leq x \leq 20$);
(C1-3) an α,ω-ene-yne expressed by general formula (2-3):

 (2-3)

(wherein $1 \leq x \leq 20$);

(C1-4) a bisalkenyl polyether compound expressed by general formula (2-4):

$$C_mH_{2m-1}O(C_nH_{2n}O)_yC_mH_{2m-1} \quad (2-4)$$

(wherein 2≤m≤20, 2≤n≤4, y is a total value of the repetitions of the oxyethylene unit, the oxypropylene unit, and the oxybutylene unit, and 1≤y≤180);

(C1-5) an unsaturated group-containing silicone compound expressed by average composition formula (2-5):

$$R^2{}_pR^3{}_qSiO_{(4-p-q)/2} \quad (2-5)$$

(wherein $R^2$ may each be independent, but are monovalent organic groups that are different from $R^3$;
$R^3$ are each independently monovalent unsaturated aliphatic hydrocarbon groups having from 2 to 30 carbons, 1.0≤p≤2.5, and 0.001≤q≤1.5);

(C2-1) an unsaturated epoxy compound expressed by general formula (2-6):

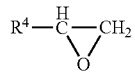

(2-6)

(wherein $R^4$ is a substituted or unsubstituted, straight or branched monovalent hydrocarbon group having one reactive unsaturated group and from 2 to 20 carbons); and (C2-2) an unsaturated group-containing cycloaliphatic epoxy compound expressed by general formula (2-7):

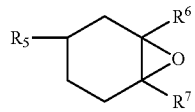

(2-7)

(wherein $R^5$ is a substituted or unsubstituted, straight or branched monovalent hydrocarbon group having one reactive unsaturated group and from 2 to 20 carbons,
$R^6$ is a hydrogen atom or a methyl group, and
$R^7$ is a hydrogen atom or a methyl group).

The monovalent organic group $R^1$ moiety in the average composition formula (1) is preferably selected from (D1) to (D10) below:

(D1) a substituted or unsubstituted, straight or branched monovalent hydrocarbon group having from 1 to 60 carbons;

(D2) a polyoxyalkylene group expressed by —$R^8O(AO)_zR^9$ (wherein AO is an oxyalkylene group having from 2 to 4 carbons, $R^8$ is a substituted or unsubstituted, straight or branched divalent hydrocarbon group having from 3 to 5 carbons, $R^9$ is a hydrogen atom or a substituted or unsubstituted, straight or branched monovalent hydrocarbon group having from 1 to 24 carbons or a substituted or unsubstituted, straight or branched acyl group having from 2 to 24 carbons, and z=1 to 100);

(D3) a substituted or unsubstituted, straight or branched alkoxy group having from 1 to 30 carbons;

(D4) a hydroxyl group;

(D5) an ester group expressed by —$R^{10}$—$COOR^{11}$ (wherein $R^{10}$ is a substituted or unsubstituted, straight or branched divalent hydrocarbon group having from 2 to 20 carbons, and $R^{11}$ is a substituted or unsubstituted, straight or branched monovalent hydrocarbon group having from 1 to 30 carbons);

(D6) an ester group expressed by —$R^{17}$—$OCOR^{18}$ (wherein $R^{17}$ is a substituted or unsubstituted, straight or branched divalent hydrocarbon group having from 2 to 20 carbons, and $R^{18}$ is a substituted or unsubstituted, straight or branched monovalent hydrocarbon group having from 1 to 30 carbons);

(D7) $L^1$ here, $L^1$ is a silylalkyl group having a siloxane dendron structure and, when i=1, is expressed by general formula (3) below:

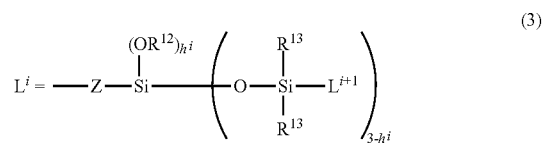

(3)

(wherein $R^{12}$ is a substituted or unsubstituted, straight or branched monovalent hydrocarbon group having from 1 to 30 carbons;

$R^{13}$ are each independently a phenyl group or an alkyl group having from 1 to 6 carbons;

Z is a divalent organic group;

i represents a generation of the aforementioned silylalkyl group represented by $L^i$ and is an integer of 1 to k when k is a number of generations that is a number of repetitions of the silylalkyl group; the number of generations k is an integer from 1 to 10; $L^{i+1}$ is the silylalkyl group when i is less than k, and the $R^{13}$ moiety when i=k; and $h^i$ is a number in a range of 0 to 3);

(D8) an alkyl group substituted by a chain polysiloxane structure expressed by general formula (4) below:

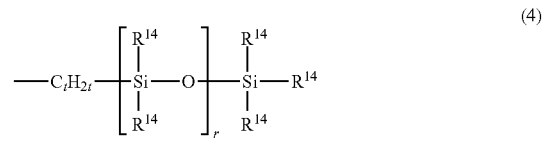

(4)

(wherein $R^{14}$ are each independently substituted or unsubstituted, straight or branched monovalent hydrocarbon groups having from 1 to 30 carbons, hydroxyl groups, or hydrogen atoms and at least one of the $R^{14}$ moieties is the monovalent hydrocarbon group; t is a number in a range from 2 to 10; and r is a number in a range from 1 to 100);

(D9) an epoxy group expressed by general formula (5) below:

(5)

(wherein $R^{15}$ is a substituted or unsubstituted, straight or branched divalent hydrocarbon group having from 2 to 20 carbons); and (D10) a cycloaliphatic epoxy group expressed by general formula (6) below:

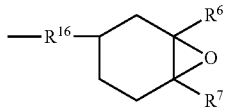

(6)

(wherein $R^{16}$ is a substituted or unsubstituted, straight or branched divalent hydrocarbon group having from 2 to 20 carbons, and $R^6$ and $R^7$ are synonymous with those described above).

Furthermore, the first object of the present invention is achieved by a manufacturing method for a liquid organopolysiloxane comprising reacting:

(A) an organohydrogenpolysiloxane;
(B) a glycerin derivative group-containing organic compound having reactive unsaturated group; and
(C) at least one type of organic compound selected from the group consisting of (C1) an organic compound having an average number of reactive unsaturated group in the molecule that is greater than 1 and (C2) an organic compound having not less than one reactive unsaturated group and not less than one epoxy group in the molecule.

The organohydrogenpolysiloxane (A) and the glycerin derivative group-containing organic compound having reactive unsaturated group (B) are preferably reacted and, thereafter, the (C) at least one type of organic compound selected from the group consisting of (C1) the organic compound having an average number of reactive unsaturated group in the molecule that is greater than 1 and (C2) the organic compound having not less than one reactive unsaturated group and not less than one epoxy group in the molecule is preferably reacted with the organohydrogenpolysiloxane (A).

In the manufacturing method for a liquid organopolysiloxane, (Q) an organic compound having one reactive unsaturated group in the molecule (with the exception of the component (C2)) may be further reacted.

The second object of the present invention can be achieved by a raw material for use in an external use preparation or a cosmetic composition or an external use preparation or cosmetic composition comprising the liquid organopolysiloxane; a composition comprising at least one type of oil agent in addition to the liquid organopolysiloxane; and a raw material for use in an external use preparation or a cosmetic composition or an external use preparation or cosmetic composition comprising the composition. The composition may be in the form of an emulsion.

The raw material for use in an external use preparation or a cosmetic composition can be a tactile sensation improver, a film-forming agent, a binder, a viscosity adjuster, a thickening agent, a moisturizing agent, a skin adhesive, a surfactant, an emulsifier, or a powder dispersing agent.

The third object of the present invention can be achieved by an external use preparation or a cosmetic composition comprising the liquid organopolysiloxane, characterized by not comprising a compound including an oxyalkylene structure where an average value of the number of repetitions of the oxyalkylene unit is two or more. Additionally, odor can be reduced and the liquid organopolysiloxane or composition thereof of the present invention can be advantageously used in an external use preparation or a cosmetic composition by adding one or more acidic substances thereto and, thereafter, removing volatile components by heating or reducing pressure.

Advantageous Effects of Invention

According to the present invention, a novel liquid organopolysiloxane can be provided that has affinity with various oil agents, and has superior emulsifying characteristics, imparts superior tactile sensation, and, in cases where compounded in an external use preparation or cosmetic composition comprising water and an oil agent, takes advantage of the effects of water to suppress oiliness and provide a smooth feeling when applying, a well-conforming, natural feeling to the skin, excellent moisturizing effects, a lack of stickiness, and similar superior sensations during use.

Additionally, the liquid organopolysiloxane of the present invention can display superior emulsifying performance with respect to both nonpolar oil agents and polar oil agents in emulsions in which both water and an oil agent are present. The emulsion may also comprise a polyhydroxy alcohol. Thus, it is possible to design external use preparations or cosmetic compositions with various formulations by compounding the liquid organopolysiloxane of the present invention in an external use preparation or a cosmetic composition.

Furthermore, the liquid organopolysiloxane of the present invention has emulsifying performance as an emulsifier for use in water-in-oil emulsions that is superior to that of known glycerin-modified silicones. Therefore, it is possible to formulate/design a variety of W/O emulsions including oil agents that do not comprise compounds having polyoxyethylene (PEG) structures. As a result, problems caused by the oxidation degradation of the polyoxyethylene (PEG) can be essentially improved. In the conventional technology, in cases where a conventional glycerin-modified silicone is used as an emulsifier for a water-in-oil emulsion, there are problems in that emulsifying performance of the conventional glycerin-modified silicone alone is insufficient and, thus it is not appropriate for use in an actual formulation (because it cannot maintain the stability of the system). Therefore, there has been no choice but to use a more reliable polyether-modified silicone emulsifier in combination with the glycerin-modified silicone, which makes it impossible to achieve the goal of shifting all cosmetic compositions to PEG-FREE formulations. However, the liquid organopolysiloxane of the present invention is advantageous in that it has superior performance as said emulsifier and can maintain the stability of a practical formulation of a cosmetic composition without the need to add a polyether-modified silicone or similar PEG material.

That is, by using the liquid organopolysiloxane of the present invention, it is unnecessary to use other hydrophilic silicone emulsifiers having PEG structures or similar nonionic surfactants, and it is possible to prepare a water-in-oil emulsion composition or the like having sufficient stability. Moreover, it is possible to shift the entire formulation of the cosmetic composition or the external use preparation to a PEG-FREE formulation (i.e. a formulation that does not comprise compounds having polyoxyethylene (PEG) structures). In other words, by using the liquid organopolysiloxane of the present invention, the cosmetic products industry can institute a business strategy that is extremely environmentally friendly and which complies with the global trend for changing the entire formulation of end consumer products such as cosmetic products and the like to PEG-FREE formulations.

Furthermore, the liquid organopolysiloxane of the present invention has superior powder dispersion stability, and can uniformly and finely disperse a powder and can, particularly, enhance the storage stability of a composition comprising a powder.

Due to the functionality thereof, the liquid organopolysiloxane of the present invention can be advantageously used as a tactile sensation improver, a film-forming agent, a binder, a viscosity adjusting agent, a moisturizing agent, a skin adhesive, a surfactant, an emulsifier, a powder dispersing agent, or a similar raw material for use in an external use preparation or a cosmetic composition; and can be arbitrarily compounded in a cosmetic composition or an external use preparation. Particularly, the present invention can provide a nonaqueous emulsion composition that is usable as a drug delivery system. Additionally, the liquid organopolysiloxane of the present invention can be used with an oil agent in a composition because it can be uniformly mixed with oil agents. Furthermore, a composition comprising an oil agent in conjunction with the liquid organopolysiloxane of the present invention has superior storage stability. Additionally, odor of the liquid organopolysiloxane of the present invention can be easily reduced by acidizing and, therefore, design of cosmetic compositions in which functionality related to odor is important, particularly scent-less or low-scent cosmetic compositions, or cosmetic compositions imparted with a particular scent is easy.

DESCRIPTION OF EMBODIMENTS

Liquid Organopolysiloxane and Manufacturing Method Thereof

A first aspect of the present invention is a liquid organopolysiloxane having fluidity at least 100° C., a silicon-bonded glycerin derivative group, and a crosslinked structure comprising a carbon-silicon bond at the crosslinking portion.

The liquid organopolysiloxane of the present invention has a crosslinked structure comprising a crosslinking portion that has a carbon-silicon bond, and the crosslinked structure also includes a polysiloxane chain. Here, the crosslinking portion has a different binding site than the glycerin derivative group, and is preferred to be a moiety (crosslinking point) forming the crosslinked structure between chain, cyclic, or branch chain molecules comprising an organopolysiloxane chain, a chain organic molecular chain, or a combination thereof, originating from each reaction component described below. The liquid organopolysiloxane of the present invention has a structure in which the polysiloxane chain and other molecules are loosely crosslinked. More specifically, with the liquid organopolysiloxane of the present invention, crosslinking density is low to the degree that fluidity is exhibited at least 100° C. and, therefore, is a liquid when heated from room temperature (25° C.) to at least 100° C. Properties and characteristics of the liquid organopolysiloxane of the present invention differ from those of three-dimensionally crosslinking organopolysiloxanes or rubber-like siloxanes in which the crosslinking density is high in that the liquid organopolysiloxane of the present invention has miscibility and solubility with other oil agents and solvents.

The liquid organopolysiloxane of the present invention is a liquid having fluidity at least 100° C. In the present invention, "having fluidity at least 100° C." means that after being placed in a predetermined container (such that the liquid surface is in a horizontal state) and said container being inclined, the liquid surface of the organopolysiloxane can, after one hour, return to said horizontal state. Here, "horizontal" refers to a plane intersecting the direction of gravitational force at a right angle. Note that it is obvious that the organopolysiloxane of the present invention has fluidity at temperatures of 100° C. and higher, but the scope of the present invention also encompasses a liquid organopolysiloxane with crosslinking density low to the degree that a liquidity is expressed by heating to at least 100% even when the liquid organopolysiloxane is a semi-gel or soft solid that does not exhibit fluidity at temperatures of room temperature (25° C.) and lower. The organopolysiloxane of the present invention has fluidity at least 100° C., but more preferably also exhibits liquidity in a range from 100° C. or less to room temperature. Specifically, the organopolysiloxane of the present invention preferably is a liquid having fluidity at 80° C., more preferably is a liquid having fluidity at 40° C., and even more preferably is a liquid having fluidity at room temperature (25° C.).

A loss factor tan δ at a shear frequency of 10 Hz of the liquid organopolysiloxane of the present invention is preferably not less than 1. The loss factor is a ratio (G"/G') of a storage shear modulus (G') and a loss shear modulus (G"), and indicates how much an object to be measured absorbs energy when the object is deformed. The loss factor tan δ can be measured by means of a dynamic viscoelasticity measuring instrument. In general, as the value of tan δ increases, the ability of absorbing energy and then converting said energy to heat or the like increases, and as a result, repulsion decreases.

The organopolysiloxane having a loss factor tan δ at a shear frequency of 10 Hz of not less than 1 has reduced repulsion, and does not exhibit a function as an elastic body such as a common rubber. In terms of molecular structure, this means that compared to common silicone rubbers, the degree of crosslinking of the organopolysiloxane is considerably reduced. On the other hand, with a non-crosslinking liquid such as water on which torque is not exerted, a loss factor at a shear frequency of 10 Hz cannot be measured.

The liquid organopolysiloxane of the present invention has a silicon-bonded glycerin derivative group. The glycerin derivative group constitutes a hydrophilic site of the liquid organopolysiloxane of the present invention. The structure of the glycerin derivative-modified group is not limited provided that the structure has a glycerin derivative site, but the glycerin derivative residue is preferably bonded to the silicon atom via a divalent organic group.

Here, "glycerin derivative residue" refers to a hydrophilic group having a (poly)glycerin structure, and refers to a hydrophilic group having a monoglycerin, a diglycerin, a triglycerin, a tetraglycerin, and at least a pentaglycerin structure. Additionally, the terminal hydroxyl group may be partially capped with an alkyl group. Furthermore, the (poly)glycerin structure may be straight or branched, and may be a structure that is branched in a dendritic manner as well.

The glycerin derivative group described above is preferably bonded to a silicon atom via a linking group that is at least divalent and is preferably a glycerin derivative group-containing organic group comprising at least one type of hydrophilic unit selected from hydrophilic units represented by structural formulae (4-1) to (4-3) below.

(4-1)

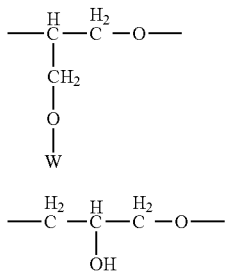

(4-2)

(4-3)

In formulae (4-1) to (4-3), W is a hydrogen atom or an alkyl group having from 1 to 20 carbons, and preferably is a hydrogen atom. Particularly, when W is a hydrogen atom, oxidation in air does not occur easily, and aldehydes such as formaldehyde and the like, and antigenic compounds such as formate esters and the like; are not easily produced over time while in storage. Therefore, when W is a hydrogen atom, there is a benefit of high environmental compatibility.

The hydrophilic units represented by structural formulae (4-1) to (4-3) are hydrophilic units included in a hydrophilic group derived from a hydrophilic compound selected principally from polyhydric alcohols including glycerin, polyglycerins (also called "polyglycerols"), and polyglycidyl ethers or compounds in which terminal hydroxyl groups thereof are partially capped by hydrocarbon groups. Furthermore, note that the glycerin derivative group according to the present invention may be a hydrophilic group optionally comprising a hydrophilic structure (polyether structure) including an oxyalkylene unit expressed by $-C_nH_{2n}O-$ (e.g. an oxyethylene unit or an oxypropylene unit). However, in cases where the entire formulation of the cosmetic composition or the external use preparation is changed to a PEG-FREE formulation (i.e. a formulation that does not comprise compounds having polyoxyethylene (PEG) structures), the glycerin derivative group according to the present invention preferably does not comprise an oxyalkylene structure including two or more oxyalkylene units in the molecule.

The glycerin derivative group may be, for example, a hydrophilic group that does not have a branched structure such as a monoglycerin-modified group or a diglycerin-modified group, and may also be a hydrophilic group that has a partial branched structure in the functional group such as a polyglycerol group or a polyglycidylether group.

More specifically, the glycerin derivative group may be a hydrophilic segment bonded to the silicon atom via a linking group that is at least divalent, comprising at least one linearly bonded hydrophilic unit selected from hydrophilic units represented by the following structural formulae (3-3) to (3-5). Similarly, the glycerin derivative group may be a hydrophilic segment bonded to the silicon atom via a linking group that is at least divalent, comprising not less than one of at least one type of hydrophilic unit selected from hydrophilic units represented by structural formulae (3-3) to (3-5) above, and a branch unit selected from groups represented by structural formulae (4-4) to (4-6) below.

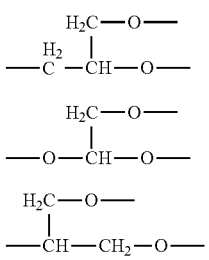

(4-4)

(4-5)

(4-6)

In structural formulae (4-4) to (4-6), the at least one hydrophilic unit selected from the hydrophilic units represented by the structural formulae (4-1) to (4-3) are each independently bonded to the two oxygen atoms. The hydrophilic unit may further be bonded to a branch unit selected from groups represented by structural formulae (4-4) to (4-6). Moreover the hydrophilic unit may be formed so as to have a dendroid-shape polyether structure, a polyglycerol structure, or a polyglycidyl ether structure obtained by branching into multiple generations. For example, the structure of the glycerin derivative group which has one branch unit represented by structural formula (4-4) and two branch units represented by structural formula (4-6) and which is branched in a dendritic manner is shown below, but it goes without saying that dendroid-shape polyglycerol structure is not limited to this example.

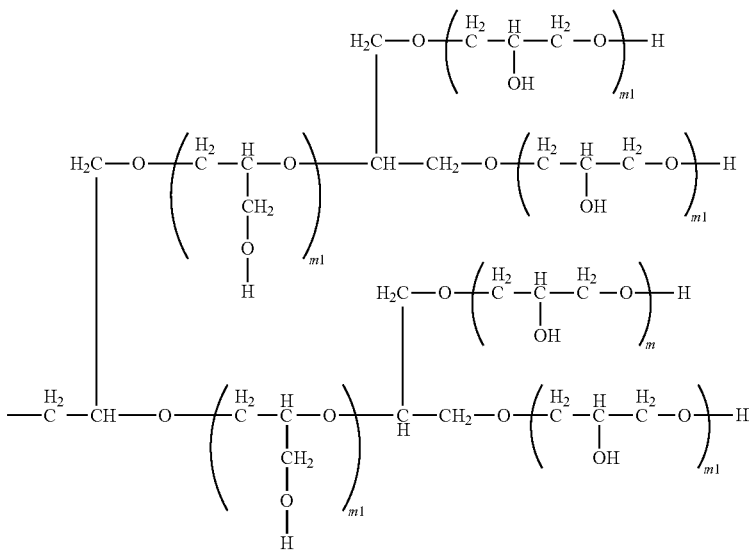

(wherein m1 is a number in a range from 0 to 50, provided that not all of the m1 moieties are 0).

The linking group that is at least divalent is a bonding site with respect to the silicon atom included in the glycerin derivative group, and a structure thereof is not particularly limited. Examples thereof include, ethylene groups, propylene groups, butylene groups, hexylene groups, and similar alkylene groups; ethylene phenylene groups, propylene phenylene groups, and similar alkylene phenylene groups; ethylene benzylene groups and similar alkylene aralkylene groups; ethyleneoxy phenylene groups, propyleneoxy phenylene groups, and similar alkyleneoxy phenylene groups; methyleneoxy benzylene groups, ethyleneoxy benzylene groups, propyleneoxy benzylene groups, and similar alkyleneoxy benzylene groups; and, furthermore, groups described below. Note that there are preferably from 0 to 3 and more preferably 0 or 1 ether bonds in the linking group that is at least divalent.

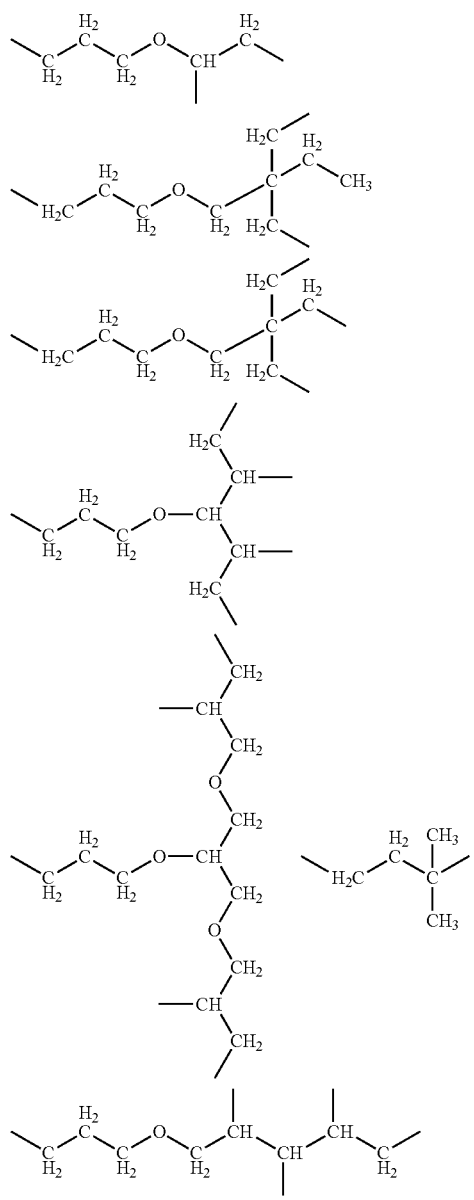

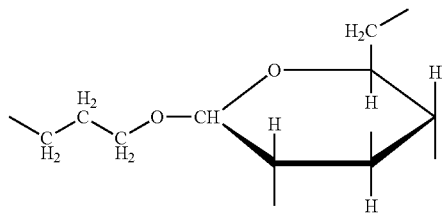

More preferably, the glycerin derivative group is a hydrophilic group represented by structural formulae (6-1) to (6-4) below, which are generally hydrophilic groups derived from polyglycerin-based compounds.

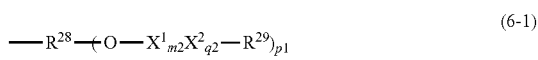

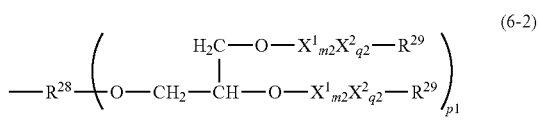

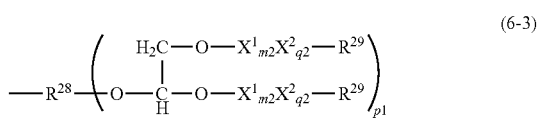

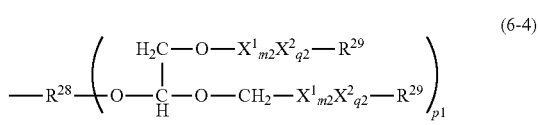

In formulae (6-1) to (6-4), $R^{28}$ is an organic group having (p1+1) valency, and p1 is a number that is greater than or equal to 1 and less than or equal to 3. As the aforementioned $R^{28}$, the same groups as the aforementioned linking groups that are at least divalent may be mentioned.

It is more preferable that p1 is equal to 1 and that $R^{28}$ is a group selected from divalent organic groups expressed by the following general formulae.

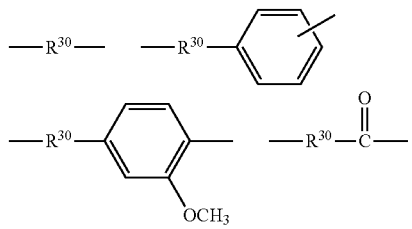

In these formulae, $R^{30}$ may have a substituent, and are each independently a straight or branched chain alkylene group or alkenylene group having from 2 to 22 carbons, or an arylene group having from 6 to 22 carbons.

$X^1$ are each independently at least one hydrophilic unit selected from the hydrophilic units expressed by general formulae (4-1-1) to (4-3-1) below, and m2 is a number in a range of 1 to 5, and is more preferably from 1 to 4.

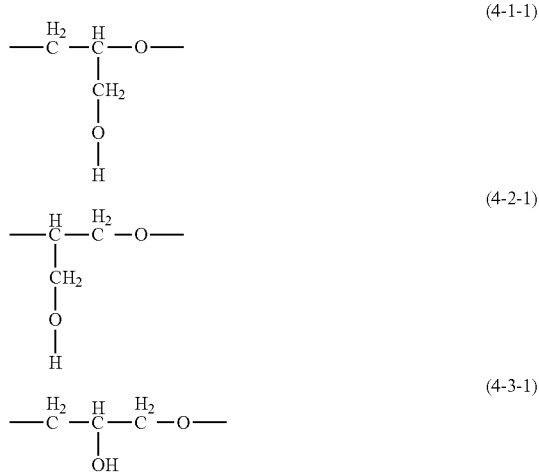

(4-1-1)

(4-2-1)

(4-3-1)

$X^2$ is an optional oxyalkylene unit that may comprise the glycerin derivative group, and q2 is a number in a range from 0 to 50. q2 is preferably a number in a range from 0 to 30, and more preferably is 0.

Note that $X^2$ is preferably an oxyethylene unit or oxypropylene unit. Additionally, when $X^2$ is continuously bonded, at least one type of polyoxyalkylene unit expressed by $-(C_2H_4O)_{t1}(C_3H_6O)_{t2}-$ (wherein t1 and t2 are each a number not less than 0, and (t1+t2) is a number in a range from 0 to 50 and preferably a number in a range from 0 to 30) can be included in the glycerin derivative group. However, in cases where the entire formulation of the cosmetic composition or the external use preparation is changed to a PEG-FREE formulation, the glycerin derivative group according to the present invention preferably does not comprise (in the molecule) an oxyalkylene structure wherein an average value of the number of repetitions of the oxyalkylene unit is two or more.

Here, the manner in which $X^1$ and $X^2$ are bonded can be block or random. That is, the glycerin derivative group may be a hydrophilic group in which hydrophilic segments, which are obtained by bonding hydrophilic units expressed by general formulae (4-1-1) to (4-3-1) above in a block manner, are bonded to hydrophilic segments comprising polyoxyalkylene units, and may be a hydrophilic group in which these constituent units are bonded in a random manner. An example thereof is a bonding pattern such as $-(X^2)_{m1}-X^1-(X^2)_{m2}-X^1-$.

$R^{29}$ is a hydrogen atom or a group selected from the group consisting of glycidyl groups, acyl groups, and alkyl groups having from 1 to 20 carbons.

It is particularly preferable for the glycerin derivative group to be a hydrophilic group derived from a (poly) glycerin represented by structural formula (6-1-1) below from the perspective of affinity and emulsifying characteristics with respect to oil agents of the liquid organopolysiloxane according to the present invention.

$R^{28'}-O-X^1{}_{m2}-R^{29}$ (6-1-1)

In the formula, $R^{28'}$ is a divalent organic group, and can be a group synonymous with those mentioned above. $X^1$ and $R^{29}$ are synonymous with the groups described above, and m2 is a number in a range of 1 to 5.

In the liquid organopolysiloxane according to the present invention, from the perspectives of affinity and emulsifying characteristics with respect to the oil agents, use as various treatment agents (surfactants or surface treatment agents), and particularly use as a powder treatment agent and use as a cosmetic raw material, the glycerin derivative group is a hydrophilic group derived from a (poly)glycerin compound and is most preferably a hydrophilic group derived from (poly)glycerin. Specifically, the glycerin derivative group is a (poly)glycerin monoallyl ether or a (poly)glyceryl eugenol, which are examples of hydrophilic groups derived from glycerin compounds having a monoglycerin, diglycerin, triglycerin, or tetraglycerin structure.

In the liquid organopolysiloxane according to the present invention, from the perspectives of affinity with respect to oil agents and emulsifying characteristics by which a PEG-FREE formulation is achievable, the glycerin derivative group is particularly preferably a diglycerin derivative group.

In the diglycerin derivative group, the average value of the number of repetitions of the hydrophilic unit expressed in structural formulae (4-1) to (4-3) is in a range from 1.1 to 2.9, and the average value of the number of repetitions is preferably in a range from 1.5 to 2.4, more preferably in a range from 1.8 to 2.2, and most preferably an average of 2. It is advantageous that the average value of the number of repetitions of the hydrophilic unit is within the range described above because a water-in-oil emulsion composition that is stable over extended periods of time can be obtained.

The number of repetitions of the glycerin unit may be an average value. A content of the diglycerin derivative group in which the number of repetitions of the glycerin unit is 2 is preferably more than 30 wt. %, more preferably 50 wt. % or more, and even more preferably 80 wt. % or more, with respect to all of the other glycerin derivative groups. Most preferable is a pure form in which purity of the diglycerin derivative group is greater than 98 wt. %. Additionally, when a PEG-FREE formulation is a goal, it is necessary that the same functional group does not comprise an oxyalkylene structure wherein an average value of the number of repetitions of the oxyalkylene unit is two or more.

The diglycerin derivative group is more preferably a diglycerin derivative group represented by structural formula (5) below:

$-R-O-X_{m3}-H$ (5)

In this formula, R is a divalent organic group, and examples thereof are synonymous with the groups described as examples of the divalent linking groups. Preferably, R is a divalent linking group that does not comprise an oxyalkylene structure wherein an average value of the number of repetitions of the oxyalkylene unit is two or more. X is at least one type of glycerin unit selected from the hydrophilic units represented by the structural formulae (4-1) to (4-3). m3 represents the number of repetitions of the glycerin unit, and is on average, a number in a range from 1.5 to 2.4. Note that the preferable range of the number of repetitions of each glycerin unit is the same as that described above.

Most preferably, the glycerin derivative group is a diglycerin derivative group-containing organic group expressed by general formula (5-1) below:

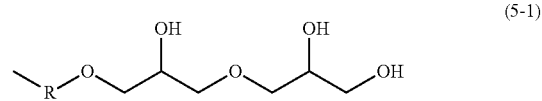

(5-1)

(wherein R is a divalent organic group); or general formula (5-2) below:

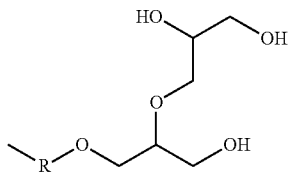
(5-2)

(wherein R is synonymous with that described above).

In the liquid organopolysiloxane according to the present invention, the diglycerin derivative group-containing organic group is preferably a hydrophilic groups derived from a diglycerin monoallyl ether or a diglyceryl eugenol.

The liquid organopolysiloxane of the present invention can be manufactured by reacting:
(A) an organohydrogenpolysiloxane;
(B) a glycerin derivative group-containing organic compound having reactive unsaturated group; and
(C) at least one type of organic compound selected from the group consisting of (C1) an organic compound having an average number of reactive unsaturated group in the molecule that is greater than 1 and (C2) an organic compound having not less than one reactive unsaturated group and not less than one epoxy group in the molecule.

The organohydrogenpolysiloxane (A) is not particularly limited provided that it has a silicon-bonded hydrogen atom, and preferably has, on average, more than one, more preferably from 1.01 to 100, even more preferably from 1.1 to 50, yet even more preferably from 1.2 to 25, and particularly preferably from 1.3 to 10 silicon-bonded hydrogen atoms per molecule. Straight, branched, or reticulated organopolysiloxanes can be used. The positions of the silicon-bonded hydrogen atoms on the organohydrogenpolysiloxane are not restricted, and the silicon-bonded hydrogen atoms may be present on the main chain or at the terminal. One type of organohydrogenpolysiloxane may be used as the component (A) or two or more types of organohydrogenpolysiloxanes may be used.

Examples of the component (A) include 1,1,3,3-tetramethyldisiloxane, 1,3,5,7-tetramethyl cyclotetrasiloxane, methylhydrogenpolysiloxane capped at both molecular terminals with trimethylsiloxy groups, a dimethylsiloxane.methyl hydrogen siloxane copolymer capped at both molecular terminals with trimethylsiloxy groups, dimethylsiloxane capped at both molecular terminals with dimethylhydrogensiloxy groups, dimethylpolysiloxane capped at both molecular terminals with dimethylhydrogensiloxy groups, a dimethylsiloxane.methyl hydrogen siloxane copolymer capped at both molecular terminals with dimethylhydrogensiloxy groups, a methylhydrogensiloxane.diphenylsiloxane copolymer capped at both molecular terminals with trimethylsiloxy groups, a methylhydrogensiloxane.diphenylsiloxane.dimethylsiloxane copolymer capped at both molecular terminals with trimethylsiloxy groups, a copolymer comprising a $(CH_3)_2HSiO_{1/2}$ unit and a $SiO_{4/2}$ unit, and a copolymer comprising a $(CH_3)_2HSiO_{1/2}$ unit, a $SiO_{4/2}$ unit, and a $(C_6H_5)SiO_{3/2}$ unit.

The component (A) is preferably expressed by average composition formula (1):

$$R^1_a H_b SiO_{(4-a-b)/2} \quad (1)$$

(wherein $R^1$ are each independently monovalent organic groups, $1.0 \leq a \leq 3.0$, and $0.001 \leq b \leq 1.5$).

The molecular structure of the organohydrogenpolysiloxane (A) is not particularly limited and examples thereof include straight, straight having partially branched, branched chains, cyclic, and dendritic structures. Of these, straight structures are preferable. Additionally, a molecular weight thereof is not particularly limited and products having a low molecular weight to products having a high molecular weight can be used. Specifically, a number-average molecular weight is preferably in a range from 100 to 1,000,000 and more preferably in a range from 300 to 500,000.

Examples of such organohydrogenpolysiloxanes includes those expressed by the following structural formulae:

$$R^1_3SiO(R^1_2SiO)_v(R^1SiHO)_w SiR^1_3 \quad (i)$$

$$HR^1_2SiO(R^1_2SiO)_v(R^1SiHO)_{z1} SiR^1_3 \quad (ii)$$

$$HR^1_2SiO(R^1_2SiO)_v(R^1SiHO)_{z1} SiR^1_2H \quad (iii)$$

(wherein $R^1$ is synonymous with that described above, v is 0 or a positive integer, w is a positive integer, and z1 is 0 or a positive integer). These organohydrogenpolysiloxanes are straight organohydrogenpolysiloxanes having a silicon-bonded hydrogen atom on (i) only the sidechain, (ii) the sidechain or one molecular terminal, or (iii) the sidechain or both molecular terminals.

The monovalent organic group is not particularly limited but is preferably selected from (D1) to (D10) below:
(D1) a substituted or unsubstituted, straight or branched monovalent hydrocarbon group having from 1 to 60 carbons;
(D2) a polyoxyalkylene group expressed by $-R^8O(AO)_z R^9$ (wherein AO is an oxyalkylene group having from 2 to 4 carbons, $R^8$ is a substituted or unsubstituted, straight or branched divalent hydrocarbon group having from 3 to 5 carbons, $R^9$ is a hydrogen atom or a substituted or unsubstituted, straight or branched monovalent hydrocarbon group having from 1 to 24 carbons or a substituted or unsubstituted, straight or branched acyl group having from 2 to 24 carbons, and z=1 to 100);
(D3) a substituted or unsubstituted, straight or branched alkoxy group having from 1 to 30 carbons;
(D4) a hydroxyl group;
(D5) an ester group expressed by $-R^{10}-COOR^{11}$ (wherein $R^{19}$ is a substituted or unsubstituted, straight or branched divalent hydrocarbon group having from 2 to 20 carbons, and $R^{11}$ is a substituted or unsubstituted, straight or branched monovalent hydrocarbon group having from 1 to 30 carbons);
(D6) an ester group expressed by $-R^{17}-OCOR^{18}$ (wherein $R^{17}$ is a substituted or unsubstituted, straight or branched divalent hydrocarbon group having from 2 to 20 carbons, and $R^{18}$ is a substituted or unsubstituted, straight or branched monovalent hydrocarbon group having from 1 to 30 carbons);
(D7) $L^1$
here, $L^1$ is a silylalkyl group having a siloxane dendron structure and, when i=1, is expressed by general formula (3) below:

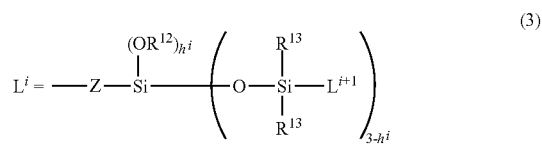
(3)

(wherein R$^{12}$ is a substituted or unsubstituted, straight or branched monovalent hydrocarbon group having from 1 to 30 carbons;
R$^{13}$ are each independently a phenyl group or an alkyl group having from 1 to 6 carbons;
Z represents a divalent organic group;
i represents a generation of the aforementioned silylalkyl group represented by L$^i$ and is an integer of 1 to k when k is a number of generations that is a number of repetitions of the silylalkyl group; the number of generations k is an integer from 1 to 10; L$^{i+1}$ is the silylalkyl group when i is less than k, and the R$^{13}$ moiety when i=k; and h$^i$ is a number in a range of 0 to 3);
(D8) an alkyl group substituted by a chain polysiloxane structure expressed by general formula (4) below:

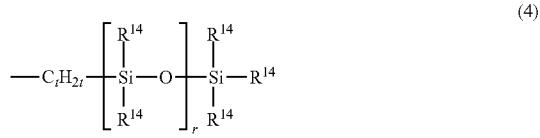

(wherein R$^{14}$ are each independently substituted or unsubstituted, straight or branched monovalent hydrocarbon groups having from 1 to 30 carbons, hydroxyl groups, or hydrogen atoms and at least one of the R$^{14}$ moieties is the monovalent hydrocarbon group; t is a number in a range from 2 to 10; and r is a number in a range from 1 to 100);
(D9) an epoxy group expressed by general formula (5) below:

(wherein R$^{15}$ is a substituted or unsubstituted, straight or branched divalent hydrocarbon group having from 2 to 20 carbons); and
(D10) a cycloaliphatic epoxy group expressed by general formula (6) below:

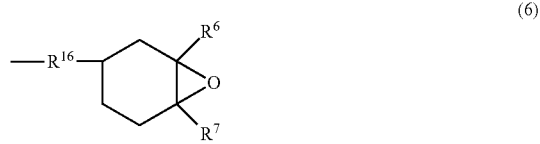

(wherein R$^{16}$ is a substituted or unsubstituted, straight or branched divalent hydrocarbon group having from 2 to 20 carbons, and R$^6$ and R$^7$ are synonymous with those described above).

From the perspectives of affinity with respect to oil agents and emulsifying characteristics by which a PEG-FREE formulation is achievable, the liquid organopolysiloxane according to the present invention preferably further comprises at least one monovalent organic group selected from:
(D1-1) a substituted or unsubstituted, straight or branched monovalent hydrocarbon group having from 9 to 60 carbons;
(D8) the alkyl group substituted by a chain polysiloxane structure expressed in general formula (4) above; and
(D7) a silylalkyl group having a siloxane dendron structure expressed by functional group L$^1$. This monovalent group is introduced into the molecule of the liquid organopolysiloxane according to the present invention by reacting the corresponding component (C) with the component (A). These functional groups have high hydrophobicity and have superior affinity with oil agents, and therefore, using such with the glycerin derivative group is advantageous because the emulsifying characteristics (applicability to a wide range of oil agent types) of the liquid organopolysiloxane according to the present invention can be further improved. Two or more types of these functional groups can be preferably introduced into the molecule.

Examples of the substituted or unsubstituted, straight or branched monovalent hydrocarbon group in (D1), (D2), and (D5) to (D8) include alkyl groups such as a methyl group, an ethyl group, a propyl group, a butyl group, a pentyl group, a hexyl group, a heptyl group, an octyl group, and the like; cycloalkyl groups such as a cyclopentyl group, a cyclohexyl group, and the like; alkenyl groups such as a vinyl group, an allyl group, a butenyl group, and the like; aryl groups such as a phenyl group, a tolyl group, and the like; aralkyl groups such as a benzyl group and the like; and groups wherein the hydrogen atoms bonded to the carbon atoms of these groups are substituted at least partially by fluorine or a similar halogen atom, or an epoxy group, a glycidyl group, an acyl group, a carboxyl group, an amino group, a methacryl group, a mercapto group, or a similar organic group. The monovalent hydrocarbon group is preferably a group other than an alkenyl group, and is more preferably a methyl group, an ethyl group, or a phenyl group.

The substituted or unsubstituted, straight or branched divalent hydrocarbon group in (D2), (D5), (D6), (D9), and (D10) is as recited above.

Examples of the substituted or unsubstituted, straight or branched alkoxy group in (D3) include a methoxy group, an ethoxy group, an isopropoxy group, a butoxy group, and similar lower alkoxy groups; a lauryl alkoxy group, a myristyl alkoxy group, a palmityl alkoxy group, an oleyl alkoxy group, a stearyl alkoxy group, a behenyl alkoxy group, and similar higher alkoxy groups; and the like.

Among the phenyl group or the alkyl group having from 1 to 6 carbons in (D7), examples of the alkyl group having from 1 to 6 carbons include methyl, ethyl, n-propyl, i-propyl, n-butyl, i-butyl, s-butyl, pentyl, neopentyl, cyclopentyl, hexyl, and similar straight, branched, or cyclic alkyl groups.

In the aforementioned general formula (3), in the case of i=k, R$^4$ is preferably a methyl group or a phenyl group. In particular, R$^4$ is preferably a methyl group when i=k.

From a technical standpoint, the number of generations k is preferably an integer from 1 to 3, and more preferably is 1 or 2. In each of the number of generations, the group represented by L$^1$ is represented as follows. In the formula, R$^{12}$, R$^{13}$, and Z are the same groups as described above.

When the number of generations is k=1, L$^1$ is expressed by the following general formula (3-1).

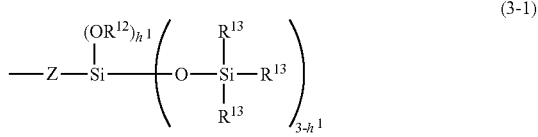

When the number of generations is k=2, L$^1$ is expressed by the following general formula (3-2).

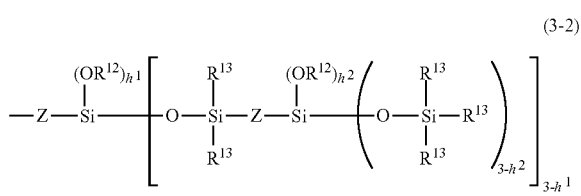

(3-2)

When the number of generations is k=3, $L^1$ is expressed by the following general formula (3-3).

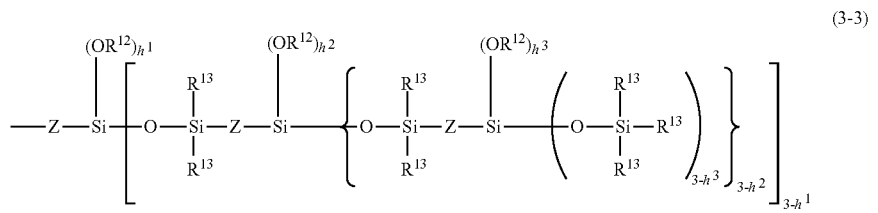

(3-3)

In the case of the number of generations is from 1 to 3, the structures expressed by the general formulae (3-1) to (3-3) each of $h^1$, $h^2$ and $h^3$ moieties is independently a number in a range from 0 to 3. These $h^i$ moieties are preferably a number in a range from 0 to 1, and $h^i$ is, in particular, preferably 0.

In general formulae (3) and (3-1) to (3-3), Z are each independently a divalent organic group, and specific examples thereof include a divalent organic group formed by addition-reacting a silicon-bonded hydrogen atom and a functional group having an unsaturated hydrocarbon group such as an alkenyl group, an acryloxy group, a methacryloxy group, or the like at the terminal. Depending on the method for introducing the silylalkyl group having a siloxane dendron structure, the functional group can be appropriately selected and is not restricted to the functional groups described above. Preferably, Z are each independently a group selected from divalent organic groups expressed by the following general formula.

—$R^{19}$—

$R^{19}$—CO—

—$R^{19}$—COO—$R^{20}$—

—CO—$R^{19}$—

—$R^{19}$—OCO—$R^{20}$—

—$R^{19}$—CONH—$R^{20}$—

—$R^{19}$—$R^{20}$—

Of these, the Z in $L^1$ is preferably a divalent organic group expressed by general formula —$R^{19}$— that is introduced by a reaction between a silicon-bonded hydrogen atom and an alkenyl group. Likewise, Z is preferably a divalent organic group expressed by general formula —$R^{19}$—COO—$R^{20}$— that is introduced by a reaction between a silicon-bonded hydrogen atom and an unsaturated carboxylic ester group. On the other hand, in the silylalkyl group represented by $L^i$, in which the number of generations k is 2 or more, and $L^i$ is $L^2$ to $L^k$, Z is preferably an alkylene group having 2 to 10 carbons and, in particular, is preferably a group selected from an ethylene group, a propylene group, a methylethylene group and a hexylene group, and most preferably is an ethylene group.

In the general formula described above, $R^{19}$ are each independently a substituted or unsubstituted straight or branched chain alkylene group or alkenylene group having from 2 to 22 carbons or an arylene group having from 6 to 22 carbons. More specifically, examples of $R^{19}$ include an ethylene group, a propylene group, a butylene group, a hexylene group, and similar straight alkylene groups; a methylmethylene group, a methylethylene group, a 1-methylpentylene group, a 1,4-dimethylbutylene group, and similar branched alkylene groups, $R^{20}$ is preferably a group selected from an ethylene group, a propylene group, a methylethylene group, and a hexylene group.

In the general formula described above, $R^{20}$ is a group selected from divalent organic groups expressed by the following formula.

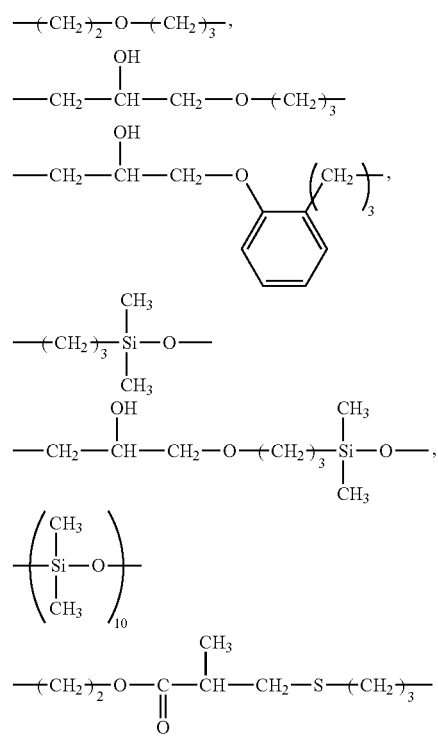

The glycerin derivative group-containing organic compound having reactive unsaturated group (B) is preferably a glycerin derivative having a carbon-carbon double bond at the terminal of the molecular chain (a). This is a (poly) glycerin derivative having an allyl(poly)glycerol, allyl polyglycidyl ether, (poly)glycerin monoallyl ether, or similar reactive functional group having an alkenyl group or the like at the molecular terminal, and can be synthesized according to a known method.

In the liquid organopolysiloxane according to the present invention, from the perspectives of affinity and emulsifying characteristics with respect to the oil agents, use as various treatment agents (surfactants or surface treatment agents), and particularly use as a powder treatment agent and use as a cosmetic raw material, the component (B) is specifically a (poly)glycerin monoallyl ether or a (poly)glyceryl eugenol, of which examples are (poly)glycerin compounds having a monoglycerin, a diglycerin, a triglycerin, or a tetraglycerin structure. A preferable structure of the glycerin residue moiety of the glycerin derivative group and a structure and the like of a compound that provides a preferable derivative group are as described above.

Examples of (C1) the organic compound having an average number of reactive unsaturated group in the molecule that is greater than 1, preferably is from 1.01 to 10, more preferably is from 1.2 to 8, even more preferably is from 1.5 to 6, and particularly preferably is from 2.0 to 4.5 as the component (C) is not structurally limited provided that it has an reactive unsaturated group and preferably a carbon-carbon double bond, and straight, branched, or reticulated organic compounds can be used. The organic compound is preferably an organopolysiloxane or an unsaturated aliphatic hydrocarbon. The positions of the reactive unsaturated group on the organic compound and preferably on the organopolysiloxane or the unsaturated aliphatic hydrocarbon are not restricted, and the reactive unsaturated group may be present on the main chain or at the terminal. However, from the perspective of ease of control of the crosslinking density, using a highly pure compound having two reactive unsaturated groups in one molecule, for example, a compound where these groups are positioned at both molecular terminals, is preferable.

The reactive unsaturated group is preferably present in the unsaturated aliphatic hydrocarbon group. The unsaturated aliphatic hydrocarbon group preferably has from 2 to 30 carbons, and more preferably has from 2 to 20 carbons. Examples of the monovalent unsaturated aliphatic hydrocarbon group having from 2 to 30 carbons include linear or branched alkenyl groups such as a vinyl group, a 1-propenyl group, an allyl group, an isopropenyl group, a 1-butenyl group, a 2-butenyl group, a pentenyl group, a hexenyl group, and the like; cycloalkenyl groups such as a cyclopentenyl group, a cyclohexenyl group, and the like; cycloalkenylalkyl groups such as a cyclopentenylethyl group, a cyclohexenylethyl group, a cyclohexenylpropyl group, and the like; and alkynyl groups such as an ethynyl group, a propargyl group, and the like. An alkenyl group is preferable, and a vinyl group and a hexenyl group are, in particular, preferable.

In cases where the component (C1) is the organopolysiloxane, the unsaturated aliphatic hydrocarbon group containing an reactive unsaturated group is preferably bonded to a silicon atom. Additionally, in cases where the component (C1) is the organopolysiloxane, the group bonded to the silicon atom, other than the unsaturated aliphatic hydrocarbon, can be a substituted or unsubstituted monovalent hydrocarbon group or a monovalent organic group having a reactive functional group.

The substituted or unsubstituted monovalent hydrocarbon group is typically a substituted or unsubstituted, straight or branched monovalent saturated hydrocarbon group having from 1 to 30 carbons, preferably from 1 to 10 carbons, and more preferably from 1 to 4 carbons, or a monovalent aromatic hydrocarbon group having from 6 to 30 carbons and more preferably from 6 to 12 carbons. The component (C1) may have a hydroxyl group, or an alkoxy group having 1 to 12 carbon atoms such as a methoxy group, an ethoxy group, a propoxy group, a butoxy group, or the like, as the monovalent organic group.

Examples of monovalent saturated hydrocarbon groups having from 1 to 30 carbons include straight or branched alkyl groups such as methyl groups, ethyl groups, n-propyl groups, isopropyl groups, n-butyl groups, isobutyl groups, sec-butyl groups, tert-butyl groups, pentyl groups, hexyl groups, heptyl groups, octyl groups, nonyl groups, decyl groups, and the like; and cycloalkyl groups such as cyclopentyl groups, cyclohexyl groups, cycloheptyl groups, cyclooctyl groups, and the like.

Examples of monovalent aromatic hydrocarbon groups having from 6 to 30 carbons include aryl groups such as a phenyl group, a tolyl group, a xylyl group, a mesityl group and the like. A phenyl group is preferable. The aromatic hydrocarbon groups in the specification of the present application encompass groups in which aromatic hydrocarbons and aliphatic saturated hydrocarbons are combined, in addition to groups consisting of aromatic hydrocarbons. Examples of the groups in which aromatic hydrocarbons and saturated hydrocarbons are combined include aralkyl groups such as a benzyl group, a phenethyl group and the like.

The hydrogen atoms on the monovalent hydrocarbon may be substituted with one or more substituents. The aforementioned substituents may be selected from the group consisting of halogen atoms such as a fluorine atom, a chlorine atom, a bromine atom, and an iodine atom, a hydroxyl group, an amide group, an ester group, a carboxyl group, and an isocyanate group. A monovalent saturated or aromatic hydrocarbon group having at least one substituent described above is preferable. Specific examples thereof include a 3,3,3-trifluoropropyl group, a 3-chloropropyl group, a 3-hydroxypropyl group, a 3-(2-hydroxyethoxy)propyl group, a 3-carboxypropyl group, a 10-carboxydecyl group, a 3-isocyanatepropyl group and the like.

Examples of monovalent organic groups having reactive functional groups include a monovalent saturated or aromatic hydrocarbon group having a reactive functional group selected from the group consisting of a hydroxyl group, a mercapto group, an epoxy group, an amino group, an amide group, an ester group, a carboxyl group, and an isocyanate group. The number of the reactive functional groups present on the monovalent organic group may be one or plural. Preferably, the $R^1$ moiety is a monovalent saturated or aromatic hydrocarbon group having at least one reactive functional group described above. Examples of reactive functional groups include a 3-hydroxypropyl group, a 3-(2-hydroxyethoxy)propyl group, a 3-mercaptopropyl group, a 2,3-epoxypropyl group, 3,4-epoxybutyl group, a 4,5-epoxypentyl group, a 2-glycidoxyethyl group, a 3-glycidoxypropyl group, a 4-glycidoxybutyl group, a 2-(3,4-epoxycyclohexyl)ethyl group, a 3-(3,4-epoxycyclohexyl)propyl group, an aminopropyl group, a N-methylaminopropyl group, a N-butylaminopropyl group, a N,N-dibutylaminopropyl group, a 3-(2-aminoethoxy)propyl group, a 3-(2-aminoethylamino)propyl group, a 3-carboxypropyl group, a 10-carboxydecyl group, a 3-isocyanatepropyl group and the like.

The component (C1) is preferably a straight or branched polysiloxane. The linear component (C1) is preferably a polymer containing a diorganosiloxane unit and a triorganosiloxy unit. Examples thereof include a dimethylpolysiloxane in which both molecular terminals are capped with dimethylvinylsiloxy groups, a copolymer of methylphenylsiloxane and dimethylsiloxane in which both molecular terminals are capped with dimethylvinylsiloxy groups, a copolymer of methylvinylsiloxane and dimethylsiloxane in which both molecular terminals are capped with dimethylvinylsiloxy groups, a copolymer of methylvinylsiloxane and dimethylsiloxane in which both molecular terminals are capped with trimethylsiloxy groups, a copolymer of methylphenylsiloxane, methylvinylsiloxane and dimethylsiloxane in which both molecular terminals are capped with trimethylsiloxy groups, a copolymer of methylvinylsiloxane and dimethylsiloxane in which both molecular terminals are capped with silanol groups, polymers in which a part of methyl groups of the aforementioned polymers is replaced with an alkyl group other than a methyl group, such as an ethyl group, a propyl group or the like, or a halogenated alkyl group such as a 3,3,3-trifluoropropyl group or the like, and a mixture of two or more types of the aforementioned polymers. In particular, a straight diorganopolysiloxane having unsaturated aliphatic hydrocarbon groups, and in particular, alkenyl groups, only at both molecular terminals is preferable.

The branched component (C1) in particular, is preferably a polymer containing a diorganosiloxane unit, an organosilsesquioxane unit, and a triorganosiloxy unit. The silicon-bonded organic groups in the units described above are preferably monovalent hydrocarbon groups such as alkyl groups such as a methyl group, an ethyl group, a propyl group and the like; alkenyl groups such as a vinyl group, an allyl group, a butenyl group, a hexenyl group and the like; aryl groups such as a phenyl group, a tolyl group and the like; a halogenated alkyl groups such as a 3,3,3-trifluoropropyl group and the like; and the like. Although the organic groups may have a trace amount of a hydroxyl group, and an alkoxy group such as a methoxy group or the like, at least two silicon-bonded organic groups in this polymer must be an unsaturated aliphatic hydrocarbon group, and in particular, an alkenyl group. Additionally, a ratio of the units is not particularly restricted, but in this polymer, it is preferable that the diorganosiloxane unit be in an amount ranging from 80.00% by mol to 99.65% by mol, the organosilsesquioxane unit be in an amount ranging from 0.10% by mol to 10.00% by mol, the triorganosiloxy unit be in an amount ranging from 0.10% by mol to 10.00% by mol, and the triorganosiloxy unit be the remaining amount.

Examples of the component (C1) include (C1-5) unsaturated group-containing silicone compounds expressed by the average composition formula (2-5):

$$R^2_p R^3_q SiO_{(4-p-q)/2} \quad (2\text{-}5)$$

(wherein $R^2$ may each be independent, but are monovalent organic groups that are different from $R^3$;
$R^3$ are each independently monovalent unsaturated aliphatic hydrocarbon groups having from 2 to 30 carbons, $1.0 \leq p \leq 2.5$, and $0.001 \leq q \leq 1.5$). The monovalent unsaturated aliphatic hydrocarbon group having from 2 to 30 carbons is the synonymous with that described above.

In the average composition formula (2-5), the monovalent organic group $R^2$ is not particularly limited, but is preferably selected from (E1) to (E6) below:
(E1) a substituted or unsubstituted, straight or branched monovalent hydrocarbon group having from 1 to 60 carbons (with the exception of monovalent hydrocarbon groups having from 2 to 20 carbons and an aliphatic unsaturated group);
(E2) a hydroxyl group
(E3) an ester group expressed by —$R^{10}$—$COOR^{11}$ (wherein $R^{10}$ and $R^{11}$ are synonymous with those described above);
(E4) an ester group expressed by —$R^{17}$—$OCOR^{18}$ (wherein $R^{17}$ and $R^{18}$ are synonymous with those described above);

(E5) an amide group expressed by —$R^{21}$—$NR^{22}COR^{23}$ (wherein $R^{21}$ is a substituted or unsubstituted, straight or branched divalent hydrocarbon group having from 2 to 20 carbons, $R^{22}$ is a hydrogen atom or a substituted or unsubstituted, straight or branched monovalent hydrocarbon group having from 1 to 20 carbons, and $R^{23}$ is a substituted or unsubstituted, straight or branched monovalent hydrocarbon group having from 1 to 30 carbons); and
(E6) an amide group expressed by —$R^{24}$—$CONR^{25}R^{26}$ (wherein $R^{24}$ is a substituted or unsubstituted, straight or branched divalent hydrocarbon group having from 2 to 20 carbons, and $R^{25}$ and $R^{26}$ are each independently a hydrogen atom or a substituted or unsubstituted, straight or branched monovalent hydrocarbon group having from 1 to 20 carbons).

The definitions, types, and the like of the substituted or unsubstituted, straight or branched monovalent hydrocarbon groups or divalent hydrocarbon groups are as described above.

On the other hand, the component (C1) may be an unsaturated aliphatic hydrocarbon. Examples of unsaturated aliphatic hydrocarbons include various dienes, diynes, enynes and similar products having two or more reactive unsaturated group. In view of crosslinking, dienes, diynes, and enynes are preferable. Dienes, diynes, and enynes are compounds having a structure in which at least two reactive unsaturated group are separated by one or more, and preferably two or more single bonds in a molecule. The unsaturated aliphatic hydrocarbon group may be present at the terminal of the molecular chain, or as a pendant group in the molecular chain.

Examples of unsaturated aliphatic hydrocarbons as the component (C1) include α,ω-unsaturated alkene and alkyne having from 2 to 30 carbons. Examples of the component (C1) include (C1-1) an α,ω-diene expressed by general formula (2-1):

$$CH_2=CH(CH_2)_xCH=CH_2 \quad (2\text{-}1)$$

(wherein $1 \leq x \leq 20$); (C1-2) an α,ω-diyne expressed by general formula (2-2):

$$CH\equiv C(CH_2)_xC\equiv CH_2 \quad (2\text{-}2)$$

(wherein $1 \leq x \leq 20$); (C1-3) an α,ω-ene-yne expressed by general formula (2-3):

$$CH_2=CH(CH_2)_xC\equiv CH \quad (2\text{-}3)$$

(wherein $1 \leq x \leq 20$); and (C1-4) a bisalkenyl polyether compound expressed by general formula (2-4):

$$C_mH_{2m-1}O(C_nH_{2n}O)_yC_mH_{2m-1} \quad (2\text{-}4)$$

(wherein $2 \leq m \leq 20$, $2 \leq n \leq 4$, y is a total value of the repetitions of the oxyethylene unit, the oxypropylene unit, and the oxybutylene unit, and $1 \leq y \leq 180$).

Specific examples of unsaturated aliphatic hydrocarbons as the component (C1) include 1,4-pentadiene, 1,5-hexadiene, 1,6-heptadiene, 1,7-octadiene, 1,8-nonadiene, 1,9-decadiene, 1,11-dodecadiene, 1,13-tetradecadiene, 1,19-eicosadiene, 1,3-butadiene, 1,5-hexadiyne, 1-hexene-5-yne, and the like.

The component (C1) can be used alone or two or more components having different structures can be used. That is, the component (C1) may be a mixture of one or more types of organopolysiloxanes and one or more types of unsaturated aliphatic hydrocarbons. Therefore, "having a number of reactive unsaturated group greater than 1 on average" means having more than one reactive unsaturated group on average per molecule in the case of using two or more types of organopolysiloxanes and/or unsaturated aliphatic hydrocarbons.

Examples of (C2) the organic compound having one or more reactive unsaturated group and one or more epoxy groups in the molecule as the component (C) are not structurally limited provided that a total of two or more, preferably from 2 to 10, more preferably from 2 to 7, even more preferably from 2 to 5, and particularly preferably from 2 to 4 reactive unsaturated group and epoxy groups in the molecule. Straight, branched, and reticulated organic compounds can be used. The organic compound is preferably an organopolysiloxane or an unsaturated aliphatic hydrocarbon. The positions of the reactive unsaturated group on the organic compound and preferably on the organopolysiloxane or the unsaturated aliphatic hydrocarbon are not restricted, and the reactive unsaturated group may be present on the main chain or at the terminal. However, from the perspective of ease of control of the crosslinking density, using a highly pure compound in which the total of reactive unsaturated groups and epoxy groups in one molecule is 2 is preferable.

The reactive unsaturated group is preferably present in the unsaturated aliphatic hydrocarbon group. Examples of the unsaturated aliphatic hydrocarbon group includes those described above.

In cases where the component (C2) is an organopolysiloxane, the unsaturated aliphatic hydrocarbon group having reactive unsaturated group and/or epoxy groups is preferably bonded to the silicon atom. Additionally, in cases where the component (C2) is an organopolysiloxane, the group bonded to the silicon atom, other than the unsaturated aliphatic hydrocarbon or the epoxy group, can be the substituted or unsubstituted monovalent hydrocarbon group or the monovalent organic group having a reactive functional group described above.

The component (C2) is preferably an epoxy group-containing unsaturated aliphatic hydrocarbon having at least one epoxy group. Examples of the unsaturated aliphatic hydrocarbon include compounds having the unsaturated aliphatic hydrocarbon group described above. A compound having a monovalent unsaturated aliphatic hydrocarbon group is preferable.

Examples of the component (C2) include: (C2-1) an unsaturated epoxy compound expressed by general formula (2-6):

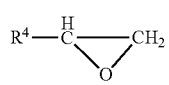

(2-6)

(wherein $R^4$ is a substituted or unsubstituted, straight or branched monovalent hydrocarbon group having one reactive unsaturated group and from 2 to 20 carbons); and
(C2-2) an unsaturated group-containing cycloaliphatic epoxy compound expressed by general formula (2-7):

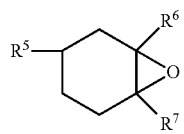

(2-7)

(wherein $R^5$ is a substituted or unsubstituted, straight or branched monovalent hydrocarbon group having one reactive unsaturated group and from 2 to 20 carbons,
$R^6$ is a hydrogen atom or a methyl group, and
$R^7$ is a hydrogen atom or a methyl group). The definitions, types, and the like of the reactive unsaturated groups in the general formulae above, and the substituted or unsubstituted, straight or branched monovalent hydrocarbon groups are as described above.

Specific examples of epoxy group-containing unsaturated aliphatic hydrocarbons as the component (C2) include an allylglycidylether, a methallylglycidylether, 1-methyl-4-isopropenylcyclohexene oxide, 1,4-dimethylcyclohexene oxide, 4-vinylcyclohexene oxide, a vinylnorbornene monooxide, a dicyclopentadiene monooxide, a butadiene monooxide, 1,2-epoxy-5-hexene, 1,2-epoxy-9-decene, and 2,6-dimethyl-2,3-epoxy-7-octene. Of these, 4-vinylcyclohexene oxide is preferable.

The component (C2) can be used alone or two or more components having different structures can be used.

The reaction for manufacturing the liquid organopolysiloxane of the present invention may be performed in the presence or in the absence of a reaction solvent, and can be performed according to a known method. The unsaturated group and the Si—H group in the present invention are reacted via a hydrosilylation reaction. Additionally, in cases where crosslinking is performed using an epoxide of (C2) the organic compound having one or more reactive unsaturated groups and one or more epoxy groups in the molecule, bonding caused by the reaction of the unsaturated group and the Si—H group and ether bonds generation caused by the self ring-opening polymerization of the epoxy groups (cationic polymerization reaction that occurs in the presence of a SiH group and a platinum catalyst) both occur. Thus, the crosslinking is carried out. In order to promote this reaction, irradiation using ultraviolet light or similar high energy beams can be applied or a common cation polymerization catalyst can be further added.

The reaction solvent is not particularly limited provided that it is nonreactive, and examples thereof include ethanol, isopropyl alcohol, and similar alcohol-based solvents; toluene, xylene, and similar aromatic hydrocarbon-based solvents; dioxane, THF, and similar ether-based solvents; n-hexane, cyclohexane, n-heptane, cycloheptane, methylcyclohexane, and similar aliphatic hydrocarbon-based solvents; and carbon tetrachloride and similar chlorinated hydrocarbon-based organic solvents. An oil agent described hereinafter may also be used as the reaction solvent. In cases where the oil agent is used as the reaction solvent, a composition comprising an organopolysiloxane and an oil agent can be directly obtained after the hydrosilylation reaction (the crosslinking).

The hydrosilylation reaction may be performed in the absence of a catalyst, but preferably is performed in the presence of a catalyst because the reaction can be carried out at a low temperature and in a shorter period of time. Examples of the hydrosilylation reaction catalyst include platinum, ruthenium, rhodium, palladium, osmium, iridium, and similar compounds, and platinum compounds are particularly effective due to their high catalytic activity. Examples of the platinum compound include chloroplatinic acid; platinum metal; platinum metal supported on a carrier such as platinum supported on alumina, platinum supported on silica, platinum supported on carbon black, or the like; and a platinum complex such as platinum-vinylsiloxane complex, platinum-phosphine complex, platinum-phosphite complex, platinum alcoholate catalyst, or the like. A usage amount of the catalyst is about 0.5 to 1000 ppm in terms of platinum metal, when using a platinum catalyst.

A reaction temperature of the hydrosilylation reaction is typically from 30 to 120° C., and a reaction time is typically from 10 minutes to 24 hours and preferably from 1 to 10 hours.

The component (A) is crosslinked by the component (C) as a result of the hydrosilylation reaction or the cationic polymerization reaction of the epoxy groups, and the polysiloxane chains originating from the component (A) are linked via the crosslinking portion having the carbon-silicon bond originating from the component (C). Additionally, the component (A) comprises a glycerin derivative group originating from the component (B). Thus, the liquid organopolysiloxane of the present invention can be obtained. However, the component (B) may have more than one reactive unsaturated groups in the molecule and, in this case, the component (B) can be used as a crosslinking component to complement the function of the component (C).

Note that the liquid organopolysiloxane of the present invention typically has a structure that is linked by the crosslinking portion having the carbon-silicon bond originating from the component (C) but may also have a portion crosslinked by the Si—O—C bond. This is because, in cases where such a structure has a silanol group, an alkoxy group or similar functional groups that are condensation reactable with the components (A) to (C), aside from the linking being formable between the polysiloxane chains, in cases where the crosslinking conditions are severe, the hydroxyl groups in the glycerin derivative group originating from the component (B) may partially react with the Si—H groups of the component (A) and linking may be formed therebetween as a side effect.

The component (A) is crosslinked by the component (C) as a result of the hydrosilylation reaction, and the polysiloxane chains originating from the component (A) are linked via the crosslinking portion having the carbon-silicon bond originating from the component (C). Additionally, the component (A) comprises a glycerin derivative group originating from the component (B). Thus, the liquid organopolysiloxane of the present invention can be obtained.

Furthermore, the liquid organopolysiloxane may be subjected to a hydrogenation treatment for the purpose of post-reaction improvement of odor caused by the remaining unsaturated compound. Methods of the hydrogenation treatment include a method in which pressurized hydrogen gas is used and a method in which a hydrogenation agent such as a metal hydride or the like is used. Furthermore, there are homogeneous reaction and heterogeneous reaction methods of hydrogenation treatments. One method can be performed alone or a combination of multiple methods can be used. However, taking into consideration the advantage that the catalyst that is used will not remain in the finished product, a heterogeneous catalytic hydrogenation reaction using a solid catalyst is most preferable.

Examples of solid catalysts (hydrogenation catalyst) that can be used include common platinum-based catalyst, palladium-based catalysts, and similar noble metal-based catalysts, and also nickel-based catalysts. Specific examples thereof include nickel, palladium, platinum, rhodium, cobalt, and similar elements, and also platinum-palladium, nickel-copper-chromium, nickel-copper-zinc, nickel-tungsten, nickel-molybdenum, and similar catalysts comprising combinations of a plurality of metals. Examples of an optional catalyst carrier include activated carbon, silica, silica alumina, alumina, zeolite, and the like. Additional examples of solid catalysts include Cu—Cr, Cu—Zn, Cu—Si, Cu—Fe—Al, Cu—Zn—Ti, and similar copper-containing hydrogenation catalysts, and the like. A form of the hydrogenation catalyst cannot be summarized because it will vary depending on the type of reaction vessel used, but typically can be appropriately selected from a powder, granule, pellet, or similar form. Additionally, the platinum catalyst used in the synthesis process (the hydrosilylation reaction) can be used as-is. One hydrogenation catalyst may be used alone or a combination of two or more of the hydrogenation catalysts may be used.

The hydrogenation treatment can be used to refine a crude product of the liquid organopolysiloxane obtained via the hydrosilylation reaction described above. Specifically, a crude product can be refined by deodorization resulting from the hydrogenation treatment in a solvent or without a solvent in the presence of a hydrogenation catalyst. Such a refined product can be preferably used in an external use preparation or a cosmetic composition in which reduction of odor and compatibility with other components are desired. Additionally, a stripping treatment in which light matter is removed by distillation by bringing a nitrogen gas into contact with a crude product or a hydrogenated product of the liquid organopolysiloxane under reduced pressure can be preferably carried out as the pre-step or post-step of the deodorization.

When manufacturing the liquid organopolysiloxane of the present invention, the component (A) and the component (B) are reacted and, thereafter, the component (C) may be further reacted with the component (A); or the component (A) and the component (C) are reacted and, thereafter, the component (B) may be further reacted with the component (A).

In cases where the component (A) and the component (B) are reacted and, thereafter, the component (C) is further reacted with the component (A), the average value of silicon-bonded hydrogen atoms per molecule of the component (A) that reacts with the reactive unsaturated groups of the component (C) is preferably not less than 0.1 and less than 2. That is, the number of silicon-bonded hydrogen atoms (per molecule of the component (A)) that constitute the crosslinking portion and that react with the reactive unsaturated groups in the component (C) is, on average, not less than 1.0, and preferably is in a range from 0.2 to 1.5, and more preferably is in a range from 0.6 to 1.3.

When manufacturing the liquid organopolysiloxane of the present invention, (Q) an organic compound having one unsaturated bond in the molecule (with the exception of the component (C2)) may be further reacted in addition to the component (A), the component (B), and the component (C). One type of the component (Q) may be used or a combination of two or more types may be used. The reactions are preferably performed sequentially in the presence of a hydrosilylation reaction catalyst. Note that the definitions, types, and the like of the reactive unsaturated groups in the component (Q) are as described above.

For example, in cases where the component (A) and the component (B) are reacted and, thereafter, the component (C) is further reacted with the component (A), the component (Q) may be reacted with the component (A) before the component (A) and the component (B) are reacted, the component (Q) may be reacted with the component (A) after the component (A) and the component (B) are reacted, or the component (Q) may be reacted with the component (A) after the reaction of the component (C).

For example, in cases where the component (A) and the component (C) are reacted and, thereafter, the component (B) is further reacted with the component (A), the component (Q) may be reacted with the component (A) before the component (A) and the component (C) are reacted, the component (Q) may be reacted with the component (A) after the component (A) and the component (C) are reacted, or the component (Q) may be reacted with the component (A) after the reaction of the component (B).

Examples of the component (Q) include (Q1) a siloxane dendron compound having one reactive unsaturated group in the molecule, and (Q2) a hydrocarbon compound having one reactive unsaturated group in the molecule, a chain organopolysiloxane having one reactive unsaturated group in the molecule, or the like.

Preferable examples of (Q1) the siloxane dendron compound having one reactive unsaturated group in the molecule include compounds having a siloxane dendron structure that have one carbon-carbon double bond at a molecular terminal, said compounds being expressed by general formula (3') below:

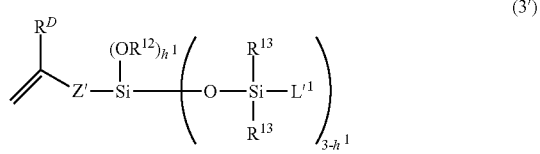

(3')

wherein
$R^{12}$ and $R^{13}$ are synonymous with those described above, $R^D$ is a hydrogen atom or a methyl group;
Z' is a divalent organic group;
$h^1$ is a number in a range from 0 to 3;
$L^{'1}$ is the $R^{13}$ moiety or, when j=1, a silylalkyl group expressed by general formula (3") below:

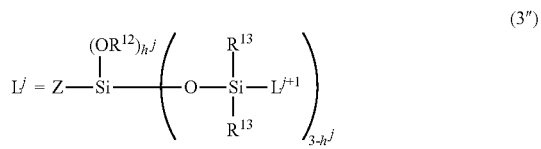

(3")

(wherein $R^{12}$ and $R^{13}$ are synonymous with those described above;
Z is a divalent organic group;
j indicates the number of generations of the silylalkyl group that is represented by $L^j$, when the number of generations (the number of repetitions) of the silylalkyl group is k', j is an integer of 1 to k', and the number of generations k' is an integer from 1 to 9; $L^{j+1}$ is the silylalkyl group when j is less than k' and is the $R^{13}$ moiety when j=k'; and $h^j$ is a number in a range from 0 to 3). The divalent organic groups in the general formulae (3') and (3") are synonymous with those described above.

Preferable examples of the hydrocarbon compound having one reactive unsaturated group in the molecule or the chain organopolysiloxane having one reactive unsaturated group in the molecule (Q2) include monounsaturated hydrocarbon compounds expressed by the following general formula:

R'—R²'

(wherein R' is an unsaturated organic group, and preferably a substituted or unsubstituted, straight or branched unsaturated hydrocarbon group having from 2 to 5 carbons;

examples of the unsaturated hydrocarbon group having from 2 to 5 carbons include vinyl groups, allyl groups, butenyl groups, and similar alkenyl groups; and
$R^{2'}$ is a substituted or unsubstituted, straight or branched monovalent hydrocarbon group having from 7 to 58 carbons); and
monounsaturated chain siloxane compounds expressed by general formula (4-1) below:

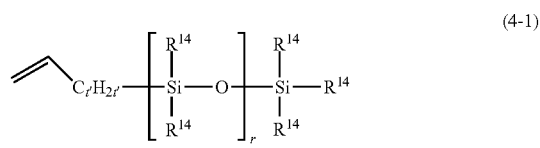

(4-1)

(wherein $R^{14}$ and t' are numbers in a range from 0 to 8 and r is a number in a range from 1 to 500). Examples of the chain organopolysiloxane having one reactive unsaturated group in the molecule include a dimethylpolysiloxane capped at one molecular terminal with a vinyl group, a methylphenylpolysiloxane capped at one molecular terminal with a vinyl group, and the like.

The hydrocarbon compound having one reactive unsaturated group in the molecule (Q2) is preferably a monounsaturated hydrocarbons having from 9 to 30 carbons and is more preferably a 1-alkene. Examples of the 1-alkene include 1-nonene, 1-decene, 1-undecene, 1-dodecene, 1-tridecene, 1-tetradecene, and the like. Examples of the chain organopolysiloxane having one reactive unsaturated group in the molecule include a dimethylpolysiloxane capped at one molecular terminal with a vinyl group, a methylphenylpolysiloxane capped at one molecular terminal with a vinyl group, and the like.

When manufacturing the liquid organopolysiloxane of the present invention, a step of acidizing the liquid organopolysiloxane of the present invention obtained via the hydrosilylation reaction of the component (A), the component (B), the component (C), and the optional component (Q) using at least one type of acidic substance is preferably carried out. As a result, the odor of the liquid organopolysiloxane can be reduced.

The acidic substance is not particularly limited, and may be any acid that matches the definition of a Lewis-acid, a Brønsted acid, or an Arrhenius acid. The acidic substance used in the present invention is preferably a water soluble acid. Thus, the acidic substance used in the present invention is preferably an Arrhenius acid, which emits protons into an aqueous solution. One type of the acidic substance may be used alone or two or more types of acidic substances may be used. In the present invention, by using the acidic substance described above, the liquid organopolysiloxane can be substantially deodorized and the generation of odor over time can be completely suppressed without disconnecting of the carbon-oxygen bonds or the silicon-oxygen bonds occurring.

The acidic substance can be selected from the group consisting of an inorganic acid, an organic acid, an acidic inorganic salt, a solid acid, and an acidic platinum catalyst.

The inorganic acid is not particularly limited and examples thereof include hydrochloric acid, sulfuric acid, nitric acid, phosphoric acid, carbonic acid, boric acid, sulfonic acid, sulfinic acid, and the like. Note that it is preferable that the inorganic acid is not a benzene sulfonic acid or similar acid having an organic group.

The organic acid is not particularly limited and monocarboxylic acid (including monohydroxymonocarboxylic acid and dihydroxymonocarboxylic acid), dicarboxylic acid (including monohydroxydicarboxylic acid and dihydroxydicarboxylic acid), polycarboxylic acid, and the like can be used. Examples thereof include: formic acid, acetic acid, trifluoroacetic acid, propionic acid, butyric acid, valeric acid, caproic acid, enanthic acid, caprylic acid, pelargonic acid, capric acid, undecanoic acid, and similar straight saturated aliphatic monocarboxylic acids (alkane acids); 2-methyl propanoate, 2-methyl butanoate, trimethyl propanoate, 2-methyl pentanoate, trimethyl acetate, and similar branched saturated aliphatic monocarboxylic acids (alkane acids); acrylic acid, methacrylic acid, crotonic acid, isocrotonic acid, acetovinyl acid, acetoallyl acid, hexenoic acid, heptenoic acid, octenoic acid, and similar unsaturated aliphatic monocarboxylic acids (alkene acids); propiolic acid, tetrolic acid, allyl acetate, hexynoic acid, octynoic acid, and similar unsaturated aliphatic monocarboxylic acids (alkyne acids); pentadienoic acid, sorbic acid, and similar polyunsaturated aliphatic monocarboxylic acids; citric acid, lactic acid, glycolic acid, α-oxy butyric acid, and similar α-hydroxymonocarboxylic acids; 2-hydroxyvaleric acid, 2-hydroxycaproic acid, β-oxy butyric acid, and similar β-hydroxymonocarboxylic acids; γ-oxy butyric acid and similar γ-hydroxymonocarboxylic acids; glyceric acid and similar dihydroxymonocarboxylic acids; hydroxy(meth)acrylate and other hydroxymonocarboxylic acids; oxalic acid, malonic acid, succinic acid, glutaric acid, adipic acid, and similar saturated aliphatic dicarboxylic acids; tartronic acid, malic acid, and similar monohydroxy saturated aliphatic dicarboxylic acid tartrates and similar dihydroxy saturated aliphatic dicarboxylic acids; maleic acid, fumaric acid, and similar unsaturated aliphatic dicarboxylic acids; benzoic acid and similar aromatic monocarboxylic acids; phthalic acid and similar aromatic dicarboxylic acids; glycine, alanine, valine, leucine, glutamic acid, aspartic acid, PL-pyrrolidone carboxylic acid, and similar amino acids; and gallic acid and similar polycarboxylic acids.

Additionally, alkyl sulfuric acid, alkyl phosphoric acid, phenol, and the like can be used as the organic acid. Note that it is not preferable that a higher fatty acid or a salt thereof be used as the organic acid.

The acidic inorganic salt is not limited, but preferably is water soluble. Particularly preferable is a water soluble acidic inorganic salt that is solid at 25° C., and, when 50 g thereof is dissolved in 1 L of ion exchanged water, the solution has a pH at 25° C. of not higher than 4, preferably not higher than 3.5, and more preferably not higher than 2.0. In cases where the acidic inorganic salt is solid at room temperature (25° C.), as necessary, the acidic inorganic salt can be easily removed via filtration. Additionally, in cases where the acidic inorganic salt is water soluble, as necessary, the acidic inorganic salt can be easily rinsed off using water. Note that pH values in the present invention are values that are measured using a pH meter having a glass electrode in a sample aqueous solution at room temperature (25° C.).

Examples that can be used as the acidic inorganic salt include acidic inorganic salts in which at least a monovalent hydrogen atom of the inorganic acid that is at least divalent is neutralized by a base. Examples of the inorganic acid that is at least divalent include sulfuric acid, sulfurous acid, and the like. Examples of the base include an alkali metal, ammonia, or the like.

More specifically, the acidic inorganic salt is preferably at least one type of acidic inorganic salt comprising a hydrogensulfate ion ($HSO_4^-$) or a hydrogensulfite ion ($HSO_3^-$) and a monovalent cation ($M^+$). Examples of the monovalent cation ($M^+$) include alkali metal ions or an ammonium ion. Particularly, the monovalent cation is preferably at least one type selected from the group consisting of a sodium ion, a potassium ion, and an ammonium ion.

Specific examples of the acidic inorganic salt include lithium hydrogensulfate, sodium hydrogensulfate, potassium hydrogensulfate, rubidium hydrogensulfate, cesium hydrogensulfate, ammonium hydrogensulfate, sodium hydrogensulfite, or hydrates thereof, and also $AlCl_3$, $FeCl_3$, $TiCl_4$, $BF_3.Et_2O$, and similar Lewis-acids. The pH of aqueous solutions in which 50 g of any of the acidic inorganic salts is dissolved in 1 L of ion exchanged water is as shown in the Tables below. From the perspective of the technical benefit of reducing odor, the water soluble acidic inorganic salt having a pH of not higher than 2.0 is preferably at least one type of acidic inorganic salt selected from the group consisting of sodium hydrogensulfate, potassium hydrogensulfate, and ammonium hydrogensulfate.

TABLE 1

| Acidic inorganic salt | pH (50 g/L) |
| --- | --- |
| Sodium hydrogensulfate | 1.5 or lower |
| Potassium hydrogensulfate | 2.0 or lower |
| Ammonium hydrogensulfate | 1.5 or lower |
| Sodium hydrogensulfite | 3.5 |

Examples of the solid acid include activated clay, acidic clay, a solid acidic zirconium dioxide, a strong acidic cation exchange resin, a fluorinated sulfonic acid resin, alumina, silica alumina, zeolite, and similar acidic solid substances. Of these, a solid acidic zirconium dioxide is preferable. Examples of the solid acidic zirconium dioxide include products prepared at not lower than 300° C. after treating zirconium hydroxide with sulfuric acid; more specifically, aluminum hydroxides or hydrous oxides, zirconium hydroxides or hydrous oxides, a solid acidic zirconium prepared by first obtaining a molded product by mixing and molding a sulfuric acid-containing compound, then baking said molded product at a temperature where a tetragonal-structured zirconia is formed, specifically at a temperature of not lower than 300° C., and specifically zirconia sulfate, and the like. Examples of commercially available products of the solid acidic zirconium dioxide include SZA-60 (manufactured by Japan Energy Corporation). The strong acidic cation exchange resin is, for example, a cation exchange resin where a functional group is a sulfonic acid group (—$SO_3H$), and examples of commercially available products thereof include Amberlyst 15, Amberlyst 16, Amberlyst 31, Amberlyst 35, and the like (manufactured by Organo Corporation) The fluorinated sulfonic acid resin is a perfluorinated polymer having a suspended sulfonic acid group bonded to the polymer chain, and specific examples thereof include the product described in Japanese Examined Patent Application Publication No. S59-4446, and the like.

Examples of the acidic platinum catalyst include chloroplatinic acid, an alcohol-modified chloroplatinic acid, an olefin complex of chloroplatinic acid, a ketone complex of chloroplatinic acid, a vinylsiloxane complex of chloroplatinic acid, a platinum tetrachloride, and the like. Of these, chloroplatinic acid is preferable.

The acidizing process described above can be carried out by bringing the liquid organopolysiloxane into contact with the acidic substance in a desired manner.

Specifically, for example, the acidizing process can be carried out by adding at least one type of the acidic substance and, optionally, water, an alcohol, or a similar organic solvent to a reaction system comprising the liquid organopolysiloxane (e.g. in a flask or similar reaction vessel) and mixing, or the like.

Particularly, it is preferable that least one type of the acidic substance and water is added to a reaction system comprising the liquid organopolysiloxane and then, while heating, the mixture is agitated or kneaded/pulverized using mechanical forces. Additionally, this treatment is preferably carried out in the presence of a lower monohydric alcohol or similar solvent. The acidizing process can be carried out at any temperature and treatment time, and can be carried out at a temperature from 0 to 200° C. and more preferably from 50 to 100° C. for a reaction time of from 0.5 to 24 hours and more preferably from about 1 to 10 hours. A content of the acidic substance can be appropriately selected depending on the acid strength, the treatment apparatus, the treatment time, and the treatment temperature. However, in cases where, for example, the acidic substance is sodium hydrogensulfate, potassium hydrogensulfate, ammonium hydrogensulfate, citric acid, glycolic acid, phosphoric acid, or a similar medium-strength acid, the content is preferably in a range from 10 to 500 ppm and more preferably in a range from 20 to 200 ppm in the liquid organopolysiloxane. Additionally, in cases where the acidic substance is hydrochloric acid, sulfuric acid, or a similar high-strength acidic substance, the content is preferably in a range from 0.1 to 50 ppm in the liquid organopolysiloxane; and in cases where the acidic substance is a weak-strength acidic substance or a solid acid exemplified by activated clay, acidic clay, solid acidic zirconium dioxide, strong acidic cation exchange resin, fluorinated sulfonic acid resin, zeolite, and the like, the content is preferably in a range from 500 to 10,000 ppm in the liquid organopolysiloxane.

With the manufacturing method for a liquid organopolysiloxane of the present invention, a heating and/or pressure reducing process (stripping process) is preferably included after the acidizing process. The low boiling point component that is the odor-causing substance can be removed (stripped) via the heating and/or pressure reducing process. Additionally, a large amount of the odor-causing substance can be removed by carrying out the acidizing process again after the stripping. Here, cases where the acidic substance remains in the reaction system are advantageous because it is not necessary to add a new acidic substance and it is sufficient to only add water. That is, the acidizing process and the stripping process can respectively be carried out two or more times for the purpose of increasing the reduction of odor.

The "low boiling point component" removed by the stripping process includes propionaldehyde and similar carbonyl compounds that are thought to be the odor-causing substance, and also the reaction solvent and similar volatile components used in the synthesis and the like of the liquid organopolysiloxane.

Note that the stripping process may be performed before the acidizing process.

It is possible to use known reaction conditions for the stripping process, but stripping under normal pressure or under reduced pressure is preferable, and stripping at a temperature of 120° C. or lower is preferable. In order to effectively perform the stripping, the stripping is preferably performed under reduced pressure or, for example, performed under a nitrogen gas or similar inert gas stream. A specific example of the removing operation of the low boiling point component is one in which the liquid organopolysiloxane or composition thereof, or hydrogenated product thereof comprising a low boiling point component is placed in a flask having a refluxing cooler, a nitrogen injection port, or the like; and, while supplying nitrogen gas, the internal pressure is reduced and internal temperature is increased and the pressure and temperature are maintained so as to be constant. Thus, the light matter is removed. Here, typically, a pressure reduction parameter is from 0.1 to 10.0 kPa, a heating temperature is from 50 to 170° C., and a treatment time is from 10 minutes to 24 hours.

In the present invention, the liquid organopolysiloxane may be neutralized using a basic substance after the acidizing process. Examples of the basic substance include sodium hydroxide, potassium hydroxide, calcium hydroxide, barium hydroxide, ammonia water, sodium hydrogen carbonate, and similar inorganic salt groups; basic amino acids, amines, pyridines, and similar organic bases; and the like. An amount of the basic substance is preferably an amount needed to neutralize a reaction system comprising the liquid organopolysiloxane but, as necessary, the amount of the basic substance may be adjusted to an amount by which weak acidity or weak alkalinity is obtained.

In the present invention, a hydrogenation treatment may be performed before and/or after the acidizing process or before and/or after the stripping process.

Furthermore, after the acidizing process, adding an alkaline buffer (trisodium phosphate, tripotassium phosphate, trisodium citrate, sodium acetate, or the like) at an amount corresponding to 100 ppm to 50,000 ppm in the obtained liquid organopolysiloxane or composition thereof is preferable from the perspective of reducing odor.

Composition Comprising the Liquid Organopolysiloxane

The present invention relates to a composition comprising the liquid organopolysiloxane. A compounded amount of the liquid organopolysiloxane in the composition is not particularly limited, but is from 1 to 99 wt. % (mass %), preferably from 5 to 95 wt. % (mass %), more preferably from 10 to 90 wt. % (mass %), even more preferably from 20 to 80 wt. % (mass %), and yet even more preferably from 30 to 70 wt. % (mass %) based on a total weight (mass) of the composition. The composition of the present invention preferably has fluidity at 25° C.

The composition of the present invention can comprise at least one type of oil agent in addition to the liquid organopolysiloxane. The oil agent is not particularly limited and can be a solid, semi-solid, or liquid oil agent. Specific examples include silicone oils, hydrocarbon oils, ester oils, vegetable oils and fats, animal oils and fats, fatty acids, higher alcohols, triglycerides, artificial sebums, fluorine-based oil agents. One type of oil agent may be used or two or more types may be used.

Specific examples of silicone oils include straight organopolysiloxane expressed by the following general formula (7), cyclic organopolysiloxanes expressed by the general formula (8), and branched organopolysiloxanes expressed by the general formula (9).

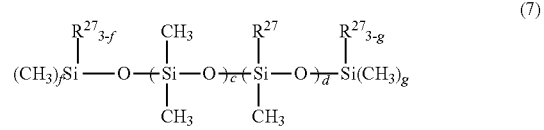

(7)

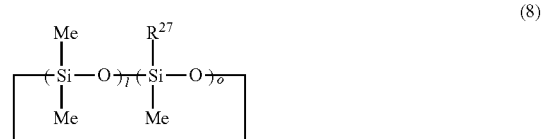

(8)

(9)

In formulae (7) to (9) above, $R^{27}$ is a hydrogen atom, hydroxyl group or a group selected from a monovalent unsubstituted or fluorine substituted alkyl group having from 2 to 30 carbons, an aryl group, an amino substituted alkyl group, an alkoxy group, and a group expressed by $(CH_3)_3SiO\{(CH_3)_2SiO\}_u Si(CH_3)_2CH_2CH_2-$. Specific examples thereof include ethyl groups, propyl groups, butyl groups, pentyl groups, hexyl groups, heptyl groups, octyl groups, decyl groups, dodecyl groups, and similar saturated aliphatic hydrocarbon groups; vinyl groups, allyl group, hexenyl groups, and similar unsaturated aliphatic hydrocarbon groups; cyclopentyl groups, cyclohexyl groups, and similar saturated cycloaliphatic hydrocarbon groups; phenyl groups, tolyl groups, naphthyl groups, and similar aromatic hydrocarbon groups; and groups wherein the hydrogen atoms bonded to the carbon atoms of these groups are substituted partially by an organic group having a halogen atom, an epoxy group, a carboxyl group, an amino group, a (meth)acryl group, a mercapto group, or the like, or a group substituted by a trimethylsiloxy group and bonded via a divalent hydrocarbon group and/or a chain polydimethyl siloxane bond. c is an integer from 0 to 1,000; d is an integer from 0 to 1,000; c+d is an integer from 1 to 2,000; f and g are each independently 0, 1, 2, or 3; l and o are each independently an integer from 0 to 8, provided that $3 \le l+o \le 8$; s is an integer from 1 to 4; and u is an integer from 0 to 500.

Examples of silicone oils having the structure described above include cyclic organopolysiloxanes such as hexamethyl cyclotrisiloxane (D3), octamethyl cyclotetrasiloxane (D4), decamethyl cyclopentasiloxane (D5), dodecamethyl-cyclohexasiloxane (D6), 1,1-diethylhexamethyl cyclotetrasiloxane, phenylheptamethyl cyclotetrasiloxane, 1,1-diphenylhexamethyl cyclotetrasiloxane, 1,3,5,7-tetravinyltetramethyl cyclotetrasiloxane, 1,3,5,7-tetramethyl cyclotetrasiloxane, 1,3,5,7-tetracyclohexyltetramethyl cyclotetrasiloxane, tris(3,3,3-trifluoropropyl) trimethylcyclotrisiloxane, 1,3,5,7-tetra(3-methacryloxypropyl) tetramethyl cyclotetrasiloxane, 1,3,5,7-tetra(3-acryloxypropyl) tetramethyl cyclotetrasiloxane, 1,3,5,7-tetra(3-carboxypropyl) tetramethyl cyclotetrasiloxane, 1,3,5,7-tetra(3-vinyloxypropyl) tetramethyl cyclotetrasiloxane, 1,3,5,7-tetra(p-vinylphenyl) tetramethyl cyclotetrasiloxane, 1,3,5,7-tetra[3-(p-vinylphenyl) propyl]tetramethyl cyclotetrasiloxane, 1,3,5,7-tetra(N-acryloyl-N-methyl-3-aminopropyl) tetramethyl cyclotetrasiloxane, 1,3,5,7-tetra(N,N-bis(lauroyl)-3-aminopropyl) tetramethyl cyclotetrasiloxane, and the like. Examples of straight organopolysiloxanes include a dimethylpolysiloxane in which both molecular terminals are capped with trimethylsiloxy groups (dimethylsilicone with a low viscosity such as 2 cSt or 6 cSt to dimethylsilicone with a high viscosity such as 1,000,000 cSt), an organohydrogenpolysiloxane, a methylphenylpolysiloxane in which both molecular terminals are capped with trimethylsiloxy groups, a copolymer of methylphenylsiloxane and dimethylsiloxane in which both molecular terminals are capped with trimethylsiloxy groups, a diphenylpolysiloxane in which both molecular terminals are capped with trimethylsiloxy groups, a copolymer of diphenylsiloxane and dimethylsiloxane in which both molecular terminals are capped with trimethylsiloxy groups, a trimethylpentaphenyltrisiloxane, a phenyl (trimethylsiloxy) siloxane, a methylalkylpolysiloxane in which both molecular terminals are capped with trimethylsiloxy groups, a copolymer of methylalkylsiloxane and dimethylpolysiloxane in which both molecular terminals are capped with trimethylsiloxy groups, a copolymer of methyl (3,3,3-trifluoropropyl) siloxane and dimethylsiloxane in which both molecular terminals are capped with trimethylsiloxy groups, an α,ω-dihydroxypolydimethylsiloxane, an α,ω-diethoxypolydimethylsiloxane, a 1,1,1,3,5,5,5-heptamethyl-3-octyltrisiloxane, a 1,1,1,3,5,5,5-heptamethyl-3-dodecyltrisiloxane, a 1,1,1,3,5,5,5-heptamethyl-3-hexadecyltrisiloxane, a tristrimethylsiloxymethylsilane, a tristrimethylsiloxyalkylsilane, a tetrakistrimethylsiloxysilane, a tetramethyl-1,3-dihydroxydisiloxane, an octamethyl-1,7-dihydroxytetrasiloxane, a hexamethyl-1,5-diethoxytrisiloxane, a hexamethyldisiloxane, an octamethyltrisiloxane, a higher alkoxy-modified silicone, a higher fatty acid-modified silicone, a carbinol-modified silicone (hydrocarbyl functional siloxane), a long chain alkyl-modified silicone, an amino-modified silicone, an amide-modified silicone, a quarternary ammonium salt-modified silicone, and the like. The liquid organopolysiloxane of the present invention can stably disperse various powders in an oil phase comprising these silicone oils, and can also stably emulsify/disperse an aqueous phase in oil phase.

Examples of the hydrocarbon oil include liquid paraffin, light liquid isoparaffin, heavy liquid isoparaffin, vaseline, n-paraffin, isoparaffin, isododecane, isohexadecane, polyisobutylene, hydrogenated polyisobutylene, polybutene, ozokerite, ceresin, microcrystalline wax, paraffin wax, polyethylene wax, polyethylene/polypropylene wax, squalane, squalene, pristane, polyisoprene, wax, and the like. The liquid organopolysiloxane of the present invention can stably disperse various powders in an oil phase comprising these hydrocarbon oils, and can also stably emulsify/disperse an aqueous phase in the oil phase.

Examples of the ester oil include hexyldecyl octanoate, cetyl octanoate, isopropyl myristate, isopropyl palmitate, butyl stearate, hexyl laurate, myristyl myristate, oleyl oleate, decyl oleate, octyldodecyl myristate, hexyldecyl dimethyloctanoate, cetyl lactate, myristyl lactate, diethyl phthalate, dibutyl phthalate, lanolin acetate, ethylene glycol monostearate, propylene glycol monostearate, propylene glycol dioleate, glyceryl monostearate, glyceryl monooleate, glyceryl tri-2-ethylhexanoate, trimethylolpropane tri-2-ethylhexanoate, ditrimethylolpropane triethylhexanoate, ditrimethylolpropane (isostearate/sebacate), trimethylolpropane trioctanoate, trimethylolpropane triisostearate, diisopropyl adipate, diisobutyl adipate, 2-hexyldecyl adipate, di-2-heptylundecyl adipate, diisostearyl malate, hydrogenated castor oil monoisostearate, N-alkylglycol monoisostearate, octyldodecyl isostearate, isopropyl isostearate, isocetyl isostearate, ethylene glycol di-2-ethylhexanoate, cetyl 2-ethylhexanoate, pentaerythritol tetra-2-ethylhexanoate, octyldodecyl gum ester, ethyl oleate, octyldodecyl oleate, neopentylglycol dicaprate, triethyl citrate, 2-ethylhexyl succinate, dioctyl succinate, isocetyl stearate, diisopropyl sebacate, di-2-ethylhexyl sebacate, diethyl sebacate, dioctyl sebacate, dibutyloctyl sebacate, cetyl palmitate, octyldodecyl palmitate, octyl palmitate, 2-ethylhexyl palmitate, 2-hexyldecyl palmitate, 2-heptylundecyl palmitate, cholesteryl 12-hydroxystearate, dipentaerythritol fatty acid ester, 2-hexyldecyl myristate, ethyl laurate, 2-octyldodecyl N-lauroyl-L-glutamate, di(cholesteryl/behenyl/octyldodecyl) N-lauroyl-L-glutamate, di(cholesteryl/octyldodecyl) N-lauroyl-L-glutamate, di(phytosteryl/behenyl/octyldodecyl) N-lauroyl-L-glutamate, di(phytosteryl/octyldodecyl) N-lauroyl-L-glutamate, isopropyl N-lauroylsarcosinate, diisostearyl malate, neopentylglycol dioctanoate, isodecyl neopentanoate, isotridecyl neopentanoate, isostearyl neopentanoate, isononyl isononanoate, isotridecyl isononanoate, octyl isononanoate, isotridecyl isononanoate, diethylpentanediol dineopentanoate, methylpentanediol dineopentanoate, octyldodecyl neodecanoate, 2-butyl-2-ethyl-1,3-propanediol dioctanoate, pentaerythrityl tetraoctanoate, pentaerythrityl hydrogenated rosin, pentaerythrityl triethylhexanoate, dipentaerythrityl (hydroxystearate/stearate/rosinate), polyglyceryl tetraisostearate, polyglyceryl-nonaisostearate, polyglyceryl-8 deca(erucate/isostearate/ricinoleate), (hexyldecanoic acid/sebacic acid) diglyceryl oligoester, glycol distearate (ethylene glycol distearate), diisopropyl dimer dilinoleate, diisostearyl dimer dilinoleate, di(isostearyl/phytosteryl) dimer dilinoleate, (phytosteryl/behenyl) dimer dilinoleate, (phytosteryl/isostearyl/cetyl/stearyl/behenyl) dimer dilinoleate, dimer dilinoleyl dimer dilinoleate, dimer dilinoleyl diisostearate, dimer dilinoleyl hydrogenated rosin condensate, dimer dilinoleic acid hardened castor oil, hydroxyalkyl dimer dilinoleyl ether, glyceryl triisooctanoate, glyceryl triisostearate, glyceryl trimyristate, glyceryl triisopalmitate, glyceryl trioctanoate, glyceryl trioleate, glyceryl diisostearate, glyceryl tri(caprylate/caprate), glyceryl tri (caprylate/caprate/myristate/stearate), hydrogenated rosin triglyceride (hydrogenated ester gum), rosin triglyceride (ester gum), glyceryl behenate eicosane dioate, glyceryl di-2-heptylundecanoate, diglyceryl myristate isostearate, cholesteryl acetate, cholesteryl nonanoate, cholesteryl stearate, cholesteryl isostearate, cholesteryl oleate, cholesteryl 12-hydroxystearate, cholesteryl ester of macadamia nut oil fatty acid, phytosteryl ester of macadamia nut oil fatty acid, phytosteryl isostearate, cholesteryl ester of soft lanolin fatty acid, cholesteryl ester of hard lanolin fatty acid, cholesteryl ester of long-chain branched fatty acid, cholesteryl ester of long-chain α-hydroxy fatty acid, octyldodecyl ricinoleate, octyldodecyl ester of lanolin fatty acid, octyldodecyl erucate, isostearic acid hardened castor oil, ethyl ester of avocado fatty acid, isopropyl ester of lanolin fatty acid, and the like. The liquid organopolysiloxane of the present invention can stably disperse various powders in an oil phase comprising these ester oils, and can also stably emulsify/disperse an aqueous phase in the oil phase.

Examples of natural animal or vegetable oils and fats and semi-synthetic oils and fats include oils and fats such as avocado oil, linseed oil, almond oil, ibota wax, perilla oil, olive oil, cacao butter, kapok wax, kaya oil, carnauba wax, liver oil, candelilla wax, beef tallow, neatsfoot oil, beef bone fat, hydrogenated beef tallow, apricot kernel oil, spermaceti wax, hydrogenated oil, wheat germ oil, sesame oil, rice germ oil, rice bran oil, sugar cane wax, sasanqua oil, safflower oil, shea butter, Chinese tung oil, cinnamon oil, jojoba wax, olive squalane, shellac wax, turtle oil, soybean oil, tea seed oil, camellia oil, evening primrose oil, corn oil, lard, rapeseed oil, Japanese tung oil, rice bran wax, germ oil, horse fat, persic oil, palm oil, palm kernel oil, castor oil, hydrogenated castor oil, castor oil fatty acid methyl ester, sunflower oil, grape oil, bayberry wax, jojoba oil, hydrogenated jojoba ester, macadamia nut oil, beeswax, mink oil, cottonseed oil, cotton wax, Japanese wax, Japanese wax kernel oil, montan wax, coconut oil, hydrogenated coconut oil, tri-coconut oil fatty acid glyceride, mutton tallow, peanut oil, lanolin, liquid lanolin, reduced lanolin, lanolin alcohol, hard lanolin, lanolin acetate, lanolin fatty acid isopropyl ester, POE lanolin alcohol ether, POE lanolin alcohol acetate, lanolin fatty acid polyethylene glycol, POE hydrogenated lanolin alcohol ether, egg yolk oil, and the like. However, from the perspective of increasing environmental compatibility and changing the entire formulation of the cosmetic composition or the external use preparation to a PEG-FREE formulation, a component having a non-POE (polyoxyethylene) structure is preferably selected.

Examples of higher fatty acids include lauric acid, myristic acid, palmitic acid, stearic acid, behenic acid, undecylenic acid, oleic acid, linolic acid, linolenic acid, arachidonic acid, eicosapentaenoic acid (EPA), docosahexaenoic acid (DHA), isostearic acid, 12-hydroxystearic acid, and the like.

Examples of higher alcohols include lauryl alcohol, myristyl alcohol, palmityl alcohol, stearyl alcohol, behenyl alcohol, hexadecyl alcohol, oleyl alcohol, isostearyl alcohol, hexyldodecanol, octyldodecanol, cetostearyl alcohol, 2-decyltetradecinol, cholesterol, sitosterol, phytosterol, lanosterol, POE cholesterol ether, monostearyl glycerol ether (batyl alcohol), monooleyl glycerol ether (selachyl alcohol), and the like.

Examples of the fluorine-based oil agent include perfluoropolyether, perfluorodecalin, perfluorooctane, and the like, and one or two or more types of these oil agents can be used as necessary.

A compounded amount of the oil agent in the composition of the present invention is not particularly limited, but is from 0.1 to 95 wt. % (mass %), preferably from 1 to 90 wt. % (mass %), more preferably from 2 to 80 wt. % (mass %), even more preferably from 3 to 70 wt. % (mass %), and yet even more preferably from 5 to 60 wt. % (mass %) based on a total weight (mass) of the composition.

The liquid organopolysiloxane of the present invention has a hydrophobic silicone chain and a hydrophilic glycerin derivative group and, therefore, functions as a surfactant or an emulsifier. Thus, the composition comprising the liquid organopolysiloxane of the present invention and at least one type of oil agent can take the form of an emulsion. The emulsion form is not particularly limited and can be an oil-in-water emulsion, a water-in-oil emulsion, or similar water-based-oil-based emulsion composition; an oil-in-alcohol (polyol) emulsion, an alcohol-in-oil (polyol) emulsion, or similar arbitrary form of emulsion.

The composition of the present invention can comprise water. A compounded amount of the water in the composition of the present invention is not particularly limited, but is from 1 to 90 wt. % (mass %), preferably from 5 to 80 wt. % (mass %), more preferably from 10 to 70 wt. % (mass %), even more preferably from 20 to 60 wt. % (mass %), and yet even more preferably from 30 to 50 wt. % (mass %) based on a total weight (mass) of the composition.

The liquid organopolysiloxane of the present invention has a hydrophobic silicone chain and a hydrophilic glycerin derivative group and, therefore, functions as a surfactant or an emulsifier. That is, by mixing the organopolysiloxane elastomer of the present invention and water (or water and a hydrophilic medium), each component can be uniformly dispersed. Therefore, the present invention can be particularly advantageously used as a hydrous composition.

The hydrous composition described above can be the liquid organopolysiloxane of the present invention, and the hydrous composition can be in the form of a hydrous gel composition, or an emulsion composition. The emulsion form is not particularly limited and can be an oil-in-water emulsion, a water-in-oil emulsion, or similar water-based-oil-based emulsion composition; an oil-in-alcohol (e.g. polyol) emulsion, an alcohol-in-oil (e.g. polyol) emulsion, or similar arbitrary form of emulsion. Particularly, a water-in-oil emulsion composition or an alcohol-in-oil (e.g. polyol) emulsion is preferable.

An average particle size of the emulsion particle formed through emulsifying using the liquid organopolysiloxane of the present invention can be measured by a conventional measurement device using a laser diffraction/scattering method or the like. The emulsion composition according to the present invention is preferably a polar solvent-in-oil emulsion, but may be an oil-in-polar solvent emulsion.

Additionally, the emulsion composition according to the present invention may be a transparent micro-emulsion in which the measured average particle size is not more than 0.1 μm, or may be a large particulate white turbid emulsion in which the average particle size is more than 10.0 μm. Furthermore, the emulsion particles may be micronized for the purpose of improving the stability and transparency of the appearance of the emulsion. An emulsion having a particle size from 0.5 to 20 μm can be selected for the purpose of improving sensation during use and adhesion characteristics to hair and skin.

The emulsion and the like described above may be produced by blending the liquid organopolysiloxane of the present invention or composition comprising the same and water by means of mechanical forces using an apparatus such as a homomixer, a paddle mixer, a Henschel mixer, a homo-disper, a colloid mill, a propeller stirrer, a homogenizer, an in-line continuous emulsifier, an ultrasonic emulsifier, or a vacuum kneader, or the like. Additionally, in the manufacturing method of the emulsion composition, the content and compounding ratio of the water is as described above and, depending on the form and use of the emulsion, is preferably selected from a range of 1 to 99 wt. % of the entire emulsion composition.

The composition of the present invention can comprise at least one type of alcohol. The alcohol preferably has water miscibility and more preferably is a lower alcohol or a polyhydric alcohol.

Examples of lower alcohols include ethanol, isopropanol, n-propanol, t-butanol, s-butanol, and the like. Examples of polyhydric alcohols include divalent alcohols such as 1,3-butylene glycol, 1,2-butylene glycol, propylene glycol, trimethylene glycol, tetramethylene glycol, 2,3-butylene glycol, pentamethylene glycol, 2-buten-1,4-diol, dibutylene glycol, pentyl glycol, hexylene glycol, octylene glycol, and the like; trivalent alcohols such as glycerol, trimethylol propane, 1,2,6-hexanetriol, and the like; polyhydric alcohols having 4 or more valences such as pentaerythritol, xylitol, and the like; and sugar alcohols such as sorbitol, mannitol, maltitol, maltotriose, sucrose, erythritol, glucose, fructose, a starch-decomposed product, maltose, xylitose, starch-decomposed sugar-reduced alcohol, and the like. Furthermore, examples other than low-molecule polyhydric alcohols include polyhydric alcohol polymers such as diethylene glycol, dipropylene glycol, triethylene glycol, polypropylene glycol, tetraethylene glycol, diglycerol, polyethylene glycol, triglycerol, tetraglycerol, polyglycerol, and the like. However, from the perspective of increasing environmental compatibility and changing the entire formulation of the cosmetic composition or the external use preparation to a PEG-FREE formulation, a non-polyether structure polyhydric alcohol and/or lower monohydric alcohol is preferably selected.

A compounded amount of the alcohol in the composition of the present invention is not particularly limited, but is from 0.1 to 50 wt. % (mass %), preferably from 1 to 40 wt. % (mass %), more preferably from 2 to 30 wt. % (mass %), even more preferably from 3 to 20 wt. % (mass %), and yet even more preferably from 4 to 10 wt. % (mass %) based on a total weight (mass) of the composition.

The liquid organopolysiloxane of the present invention or the composition comprising the same has, in essence, small tendencies to deteriorate due to oxidation caused by the oxygen in the air. Thus, it is not necessary to add a phenol, a hydroquinone, a benzoquinone, an aromatic amine, a vitamin, or similar antioxidant in order to prevent oxidation deterioration; or take steps to increase oxidation stability. However, adding such an antioxidant, for example, BHT(2,6-di-t-butyl-p-cresol), vitamin C, vitamin E, or the like, will result in a further increase in stability. In this case, an added amount of the antioxidant that is used is in a range (by weight (mass)) from 10 to 1,000 ppm and preferably from 50 to 500 ppm of the liquid organopolysiloxane.

Raw Material for Use in an External Use Preparation or a Cosmetic Composition

The liquid organopolysiloxane of the present invention or the composition comprising the same can be advantageously used as a raw material for an external use preparation and a cosmetic composition for use on a human body.

A ratio of the liquid organopolysiloxane or the composition comprising the same in the raw material for an external use preparation and a cosmetic composition is preferably from 50 to 100 wt. % (mass %), more preferably from 80 to 100 wt. % (mass %), and even more preferably from 90 to 100 wt. % (mass %) based on the total weight (mass) of the raw material. A ratio of the raw material compounded in the external use preparation or the cosmetic composition is not particularly limited but, for example, can be from 0.1 to 90 wt. % (mass %), and is preferably from 1 to 80 wt. % (mass %), more preferably from 2 to 70 wt. % (mass %), and even more preferably from 5 to 50 wt. % (mass %) based on the total weight (mass) of the external use preparation or the cosmetic composition.

Examples of raw materials for use in an external use preparation and a cosmetic composition of the present invention include a tactile sensation improver, a film-forming agent, a binder, a viscosity adjusting agent, a moisturizing agent, a skin adhesive, a surfactant, an emulsifier, or a powder dispersing agent.

While explicit gelling and solidification is not necessary, in cases where the viscosity of the compounded system is to be appropriately increased, or in cases where the viscosity of the compounded system is to be controlled within a desired range, a wide range of thickening effects (from slight to great) will be displayed by adding a liquid organopolysiloxane, having the glycerin derivative group and the crosslinking portion of the present invention and where the crosslinking portion is linked to the organopolysiloxane portion and the organic portion via Si—C bonds, to the oil phase. That is, the liquid organopolysiloxane of the present invention is a viscosity adjusting agents having superior convenience from the perspective of formulation design of external use preparations or cosmetic compositions. Particularly, one cause governing the form and viscosity of the emulsion, in an emulsification system in which a water-in-oil or polyol-in-oil outer phase portion is an oil, is the viscosity of the oil phase portion. Therefore, the liquid organopolysiloxane of the present invention functions as a useful viscosity adjusting agent in such a system.

Furthermore, a liquid organopolysiloxane, having the glycerin derivative group and the crosslinking portion of the present invention and where the crosslinking portion is linked to the organopolysiloxane portion and the organic portion via Si—C bonds, can form a film with high viscosity that does not move easily. As a result, water, even if present, is repelled, and the state of the film can be excellently maintained. Furthermore, superior effects of maintaining the film can be displayed even under circumstances where squalane is present due to the structural design. As described above, the liquid organopolysiloxane of the present invention is also useful as a film agent and a protective film oil agent.

The liquid organopolysiloxane, having the glycerin derivative group and the crosslinking portion of the present invention and where the crosslinking portion is linked to the organopolysiloxane portion and the organic portion via Si—C bonds, is a polymer simultaneously comprising a glycerin derivative moiety having superior hydrophilicity and loose crosslinking bonds in the molecule. Therefore, the liquid organopolysiloxane can function as a moisturizing agent or a skin adhesive having superior durability. To give a more specific example, due to the adhesion of the liquid organopolysiloxane to the skin, enhancements in the durability of the skin moisturizing effects and/or skin care effects of the liquid organopolysiloxane itself or, alternatively, an enhancement in the durability of the effects of other medicinal components, makeup materials, or the like used in combination with the liquid organopolysiloxane are expected.

Additionally, when the liquid organopolysiloxane, having the glycerin derivative group and the crosslinking portion of the present invention and where the crosslinking portion is linked to the organopolysiloxane portion and the organic portion via Si—C bonds is used, moisture resistance and sebum resistance of a cosmetic composition comprising a powder can be enhanced beyond those obtained in cases where a conventional glycerin-modified silicone is used, and secondary deposition can be reduced. That is, the liquid organopolysiloxane of the present invention can function as a superior binding agent.

External Use Preparation and Cosmetic Composition

The liquid organopolysiloxane of the present invention or the composition comprising the same, or the raw material for use in an external use preparation and a cosmetic composition comprising the liquid organopolysiloxane or the composition comprising the same, can be advantageously compounded in an external use preparation or a cosmetic composition and can constitute the external use preparation or the cosmetic composition of the present invention. The external use preparation or the cosmetic composition of the present invention is preferably stored in a container formed from a thermoplastic material or a container formed from a non-thermoplastic material. Additionally, the container can define at least one compartment, and can constitute a cosmetic product unit or external use preparation unit consisting of the container and the cosmetic composition or the external use preparation according to the present invention. The external use preparation or the cosmetic composition of the present invention can be principally applied to and used on keratinous substances such as skin, hair, or the like as a nontherapeutic beauty technique for the purpose of doing makeup or performing care (e.g. dry skin care).

The external use preparation is a product to be applied to human skin, nails, hair, and the like and, for example, medicament active ingredients can be compounded therein and used in the treatment of various disorders. The cosmetic composition is also a product to be applied to human skin, nails, hair, and the like, and is used for beauty purposes. The external use preparation or the cosmetic composition is preferably a skin external use preparation or a skin cosmetic composition product, or a hair external use preparation or a hair cosmetic composition product.

The skin external use preparation or the skin cosmetic composition product according to the present invention comprises the liquid organopolysiloxane of the present invention or the composition comprising the same and, while the form thereof is not particularly limited, may be in a dissolved, cream-like, solid, semi-solid, paste-like, gel-like, powder-like, multi-layer, mousse-like, or spray-like form. Specific examples of the skin external use preparation or the skin cosmetic composition product according to the present invention include toilet water, emulsions, creams, sunscreen emulsions, sunscreen creams, hand creams, cleansing compositions, massage lotions, cleansing agents, anti-perspirants, deodorants, and similar basic cosmetic products; foundations, make-up bases, blushers, rouges, eye shadows, eye liners, mascaras, nail enamels, and similar make-up cosmetic products; and the like.

Likewise, the hair external use preparation or the hair cosmetic composition product according to the present invention comprises the liquid organopolysiloxane of the present invention or the composition comprising the same and, can be used in various forms. For example, the hair external use preparation or the hair cosmetic composition product according to the present invention may be dissolved or dispersed in an alcohol, a hydrocarbon, a volatile cyclic silicone, or the like and used; furthermore, these may be used in the form of an emulsion by dispersing the liquid organopolysiloxane of the present invention and a desired emulsifier in water. Additionally, the hair external use preparation or the hair cosmetic composition product according to the present invention can be used as a spray by using propane, butane, trichloromonofluoromethane, dichlorodifluoromethane, dichlorotetrafluoroethane, carbonic acid gas, nitrogen gas, or a similar propellant. Examples of other forms include milk-like, cream-like, solid, semi-solid, paste-like, gel-like, powder-like, multi-layer, mousse-like, and similar forms. These various forms can be used as shampooing agents, rinsing agents, conditioning agents, setting lotions, hair sprays, permanent wave agents, mousses, hair colorants, and the like.

The following other components generally used in external use preparations or cosmetic compositions may be added to the external use preparation or the cosmetic composition of the present invention, provided that such components do not inhibit the effectiveness of the present invention: water, powders or coloring agents, alcohols, water-soluble polymers, film-forming agents, oil agents, oil-soluble gelling agents, organo-modified clay minerals, surfactants, resins, mediums allowable in cosmetic products, adipose phases, film-forming polymers, fibers, light protection systems capable of blocking UV rays, UV absorbers, moisturizing agents, preservatives, antimicrobial agents, perfumes, salts, antioxidants, pH adjusting agents, chelating agents, refreshing agents, anti-inflammatory agents, skin beautifying components (skin-lightening agents, cell activating agents, agents for ameliorating skin roughness, circulation promoters, skin astringents, antiseborrheic agents, and the like), vitamins, amino acids, nucleic acids, hormones, clathrates, and the like; bioactive substances, medicament active ingredients, and perfumes. However, the additives are not particularly limited thereto.

Water is free of components that are harmful to the human body and needs only to be clean. Examples thereof include tap water, purified water, mineral water, deep sea water, and the like. In cases where the external use preparation or the cosmetic composition of the present invention is water-based, desired water soluble additives can be compounded, provided that such components do not inhibit the effectiveness of the present invention. Examples of components that can be compounded in the aqueous phase include water soluble active materials such as vitamin Bs (described hereinafter), vitamin C and derivatives thereof, pantothenic acid and derivatives thereof, biotins and similar vitamins; anti-perspiration active components, water soluble UV absorbers, various water soluble pigments, and the like. However, the components are not particularly limited thereto. Additionally, a known pH adjusting agent, preservative, antimicrobial agent, or antioxidant can be arbitrarily compounded for the purpose of improving the storage stability of the external use preparation or the cosmetic composition.

The powder or coloring agent can be any powder provided that it is normally used in external use preparations or cosmetic compositions, and is not limited to form (sphere, bar, needle, plate, amorphous, spindle, cocoon, concave, or the like), particle size (aerosol, micro-particle, pigment-grade particle, or the like), or particle structure (porous, nonporous, or the like) thereof. When compounding the powder and/or coloring agent as a pigment, preferably one or two or more selected from an inorganic pigment powder, an organic pigment powder, and a resin powder having an average particle size in a range from 1 nm to 20 µm is compounded. Additionally, when using a pigment, a coated pigment is more preferable. Note that recessed fine particles formed by a silicone material, and particularly recessed fine particles, which have a structure that is partially spherical and hollow, having an average diameter of less than 5 µm (having an arch shape or a shape that is a cross-section of a horse's hoof) can also be advantageously used for the purpose of thickening the oil phase, improving tactile sensation, and the like.

Examples of the powder or coloring agent include flakes, inorganic powders, organic powders, surfactant metal salt powders (metallic soaps), colored pigments, pearl pigments, organo-modified clay minerals, metal powder pigments, and the like. In addition, compound products of these pigments can also be used. Specific examples of inorganic powders include titanium oxide, zirconium oxide, zinc oxide, cerium oxide, magnesium oxide, barium sulfate, calcium sulfate, magnesium sulfate, calcium carbonate, magnesium carbonate, talc, mica, kaolin, sericite, white mica, synthetic mica, phlogopite, lepidolite, black mica, lithia mica, silicic acid, silicic acid anhydride, aluminum silicate, sodium silicate, magnesium sodium silicate, magnesium silicate, aluminum magnesium silicate, calcium silicate, barium silicate, strontium silicate, metal salts of tungstic acid, hydroxyapatite, vermiculite, higilite, bentonite, montmorillonite, hectorite, zeolite, ceramic powder, dicalcium phosphate, alumina, aluminum hydroxide, boron nitride, and the like. Examples of organic powders include polyamide powder, polyester powder, polyethylene powder, polypropylene powder, polystyrene powder, polyurethane powder, benzoguanamine powder, polymethylbenzoguanamine powder, polytetrafluoroethylene powder, poly(methyl methacrylate) powder, cellulose, silk powder, nylon powder, nylon 12, nylon 6, silicone powder, silicone rubber spherical powder, silicone rubber spherical powder that is surface-coated with polymethylsilsesquioxane, polymethylsilsesquioxane spherical powder, copolymers of styrene and acrylic acid, copolymers of divinylbenzene and styrene, vinyl resin, urea resin, phenol resin, fluorine resin, silicone resin, acrylic resin, melamine resin, epoxy resin, polycarbonate resin, macrocrystalline fiber powder, starch powder, lauroyl lysine, and the like. Examples of surfactant metal salt powders include zinc stearate, aluminum stearate, calcium stearate, magnesium stearate, zinc myristate, magnesium myristate, zinc palmitate, zinc laurate, zinc cetylphosphate, calcium cetylphosphate, sodium zinc cetylphosphate, and the like. Examples of colored pigments include inorganic red pigments such as red iron oxide, iron oxide, iron hydroxide, iron titanate, and the like; inorganic brown pigments such as gamma-iron oxide and the like; inorganic yellow pigments such as yellow iron oxide, ocher, and the like; inorganic black iron pigments such as black iron oxide, carbon black and the like; inorganic purple pigments such as manganese violet, cobalt violet, and the like; inorganic green pigments such as chromium hydroxide, chromium oxide, cobalt oxide, cobalt titanate, and the like; inorganic blue pigments such as Prussian blue, ultramarine blue, and the like; laked pigments of tar pigments such as Red No. 3, Red No. 104, Red No. 106, Red No. 201, Red No. 202, Red No. 204, Red No. 205, Red No. 220, Red No. 226, Red No. 227, Red No. 228, Red No. 230, Red No. 401, Red No. 505, Yellow No. 4, Yellow No. 5, Yellow No. 202, Yellow No. 203, Yellow No. 204, Yellow No. 401, Blue No. 1, Blue No. 2, Blue No. 201, Blue No. 404, Green No. 3, Green No. 201, Green No. 204, Green No. 205, Orange No. 201, Orange No. 203, Orange No. 204, Orange No. 206, Orange No. 207, and the like, laked pigments of natural pigments such as carminic acid, laccaic acid, carthamin, brazilin, crocin, and the like. Examples of pearl pigments include mother of pearl pigments, titanium oxide-coated mica, titanated mica, iron oxide-coated titanated mica, titanium oxide-coated mica, bismuth oxychloride, titanium oxide-coated bismuth oxychloride, titanium oxide-coated talc, fish scale foil, titanium oxide-coated colored mica, and the like. Examples of the metal powder pigment include powders of metals such as aluminum, gold, silver, copper, platinum, stainless steel, and the like.

In particular, a powder that absorbs and scatters ultraviolet light, such as fine particulate titanium oxide, fine particulate iron-containing titanium oxide, fine particulate zinc oxide, fine particulate cerium oxide, compound products thereof, and the like may be used as the inorganic powder. More specifically, an inorganic ultraviolet light blocking component may be compounded as an ultraviolet light scattering agent such as the inorganic powder pigments and metal powder pigments mentioned above. Examples thereof include metal oxides such as titanium oxide, zinc oxide, cerium oxide, titanium suboxide, iron-doped titanium oxides, and the like; metal hydroxides such as iron hydroxides and the like; metal flakes such as platy iron oxide, aluminum flake, and the like; and ceramics such as silicon carbide, and the like. Of these, at least one type of a material selected from fine particulate metal oxides and fine particulate metal hydroxides with an average particle size in a range from 1 to 100 nm is preferable.

Examples of the organo-modified clay mineral include dimethylbenzyl dodecylammonium montmorillonite clay, dimethyldioctadecylammonium montmorillonite clay, dimethylalkylammonium hectorite, benzyldimethylstearylammonium hectorite, distearyldimethylammonium chloride-treated aluminum magnesium silicate, and the like. Examples of commercially available products include Benton 27 (benzyldimethylstearylammonium chloride-treated hectorite, manufactured by Nationalred Co.), Benton 38 (distearyldimethylammonium chloride-treated hectorite, manufactured by Nationalred Co.), and the like.

The silicone rubber spherical powder (also known as a silicone elastomer spherical powder) preferably has a primary particle size in a range from 0.1 to 50 µm. Examples of commercially available products of the silicone rubber spherical powder include Trefil E-506S, Trefil E-508, 9701 Cosmetic Powder, 9702 Powder, EP-9215 Cosmetic Powder, EP-9261 TI Cosmetic Powder, EP-9293 AL Cosmetic Powder, EP-9289 LL Cosmetic Powder (all manufactured by Dow Corning Toray Co., Ltd.), and the like. In addition, the silicone rubber spherical powder can also be used in the external use preparation or the cosmetic composition of the present invention in the form of an aqueous dispersion liquid. Examples of commercially available products of the aqueous dispersions include "BY 29-129" and "PF-2001 PIF Emulsion" (manufactured by Dow Corning Toray Co., Ltd.), and the like.

Furthermore, these powders or coloring agents are preferably subjected to a water-repellent treatment. Additionally, a product can be used in which these powders and/or coloring agents are compounded together; or subjected to surface treatment using a general oil agent, a silicone compound other than the liquid organopolysiloxane according to the present invention, a fluorine compound, a surfactant, or the like. One type thereof or two or more types thereof can be used, as necessary. Alternatively, it is possible to use a powder or a coloring agent that has been surface treated by the liquid organopolysiloxane of the present invention, and this is preferable from the perspective that a powder composition can be formed that has superior dispersion stability in various oil agents.

Examples of such water-repellent treatments include various treatments in which the powder and/or coloring agent is surface treated with a water repellency agent. Specific examples thereof include organosiloxane treatments such as a methylhydrogenpolysiloxane treatment, a silicone resin treatment, a silicone gum treatment, an acryl silicone treatment, a fluorinated silicone treatment, a glycerin-modified silicone treatment, and the like; metallic soap treatments such as a zinc stearate treatment and the like; silane treatments such as a silane coupling agent treatment, an alkylsilane treatment, and the like; fluorine compound treatments such as a perfluoroalkylsilane treatment, a perfluoroalkyl phosphate treatment, a perfluoro polyether treatment, and the like; amino acid treatments such as an N-lauroyl-L-lysine treatment and the like; oil agent treatments such as a squalane treatment and the like; and acryl treatments such as an alkyl acrylate treatment and the like. One of the treatments described above can be used or a combination of two or more can be used.

Particularly preferable examples of these powders or coloring agents include at least one type of powder or coloring agent selected from among the group consisting of a silicone resin powder, a silicone rubber powder, an organic resin powder (with the exception of silicone resin powders), an organo-modified clay mineral, titanium oxide, zinc oxide, a titanated mica, a metal soap, an inorganic body pigment, an inorganic coloration pigment and a coated pigment.

Examples of the alcohols include at least one type selected from a lower alcohol, a sugar alcohol, and a higher alcohol. Specific examples of lower alcohols include ethanol, isopropanol, and the like. Specific examples of sugar alcohols include sorbitol, maltose, and the like. Specific examples of higher alcohols include lauryl alcohol, myristyl alcohol, palmityl alcohol, stearyl alcohol, behenyl alcohol, hexadecyl alcohol, oleyl alcohol, isostearyl alcohol, hexyldodecanol, octyldodecanol, cetostearyl alcohol, 2-decyltetradecinol, cholesterol, sitosterol, phytosterol, lanosterol, POE cholesterol ether, monostearyl glycerol ether (batyl alcohol), monooleyl glycerol ether (selachyl alcohol), and the like.

The water-soluble polymer can be compounded for the purpose of enhancing sensation during use of the external use preparation or the cosmetic composition or as a water soluble moisturizing agents or film-forming polymer. Any of amphoteric, cationic, anionic, and nonionic polymers, and water-swellable clay minerals can be used provided that the water-soluble polymer is one that is commonly used in external use preparations or cosmetic products, and it is possible to use one or two or more of these water-soluble polymers. The water-soluble polymers described above have an effect of thickening a hydrous component and, for this reason, are particularly useful stabilizing the system when obtaining a gel-like hydrous external use preparation or cosmetic composition, a water-in-oil emulsion external use preparation or cosmetic composition, and an oil-in-water emulsion external use preparation or cosmetic composition. However, from the perspective of increasing environmental compatibility and changing the entire formulation of the cosmetic composition or the external use preparation to a PEG-FREE formulation, a non-polyether structure water-soluble polymer is preferably selected.

Examples of amphoteric water-soluble polymers include amphoteric starches, dimethyldiallylammonium chloride derivatives (for example, acrylamide-acrylic acid-dimethyldiallylammonium chloride copolymers and acrylic acid-dimethyldiallylammonium chloride copolymers), and methacrylic acid derivatives (for example, polymethacryloylethyldimethylbetaines, N-methacryloyloxyethyl-N,N-dimethylammonium-α-methylcarboxybetaine-alkyl methacrylate copolymers, and the like).

Examples of cationic water-soluble polymers include quaternary nitrogen-modified polysaccharides (for example, cation-modified cellulose, cation-modified hydroxyethylcellulose, cation-modified guar gum, cation-modified locust bean gum, cation-modified starch, and the like); dimethyldiallylammonium chloride derivatives (for example, copolymers of dimethyldiallylammonium chloride and acrylamide, poly(dimethylmethylene piperidinium chloride), and the like); vinylpyrrolidone derivatives (for example, copolymers of vinylpyrrolidone and dimethylaminoethyl methacrylic acid, copolymers of vinylpyrrolidone and methacrylamide propyltrimethylammonium chloride, copolymers of vinylpyrrolidone and methylvinylimidazolium chloride, and the like); and methacrylic acid derivatives (for example, methacryloylethyldimethylbetaine-methacryloylethyltrimethyl ammonium chloride-2-hydroxyethyl methacrylate copolymers, methacryloylethyldimethylbetaine-methacryloylethyltrimethyl ammonium chloride-methoxy polyethylene glycol methacrylate copolymers, and the like).

Examples of anionic water-soluble polymers include poly (acrylic acid) and alkali metal salts thereof, poly(methacrylic acid) and alkali metal salts thereof, hyaluronic acid and alkali metal salts thereof, acetylated hyaluronic acid and alkali metal salts thereof, water-soluble polymers of aliphatic carboxylic acids or metal salts thereof, such as hydrolysates of methyl vinyl ether-maleic anhydride copolymers, carboxymethyl cellulose and alkali metal salts thereof, methyl vinyl ether-maleic acid half ester copolymers, alkanolamide solutions of acrylic resins, and carboxyvinyl polymers.

Examples of nonionic water-soluble polymers include poly(vinyl pyrrolidone), highly polymerized polyethylene glycols, PEG/PPG-36/41 dimethyl ethers, PEG/PPG-14/7 dimethyl ethers, vinyl pyrrolidone-vinyl acetate copolymers, vinyl pyrrolidone-dimethylaminoethyl methacrylate copolymers, vinyl caprolactam-vinyl pyrrolidone-dimethylaminoethyl methacrylate copolymers, cellulose and derivatives thereof (for example, methyl cellulose, ethyl cellulose, hydroxyethyl cellulose, hydroxypropyl cellulose, and carboxymethyl cellulose), keratin and collagen and derivatives thereof, calcium alginate, pullulan, agar, gelatin, tamarind seed polysaccharides, xanthan gum, carrageenan, high-methoxylpectin, low-methoxylpectin, guar gum, pectin, gum arabic, crystalline cellulose, arabinogalactan, karaya gum, gum tragacanth, alginic acid, albumin, casein, curdlan, gellan gum, dextran, pyrus cyclonia seed gum, gum tragacanth, chitin/chitosan derivatives, starches (rice, corn, potato, wheat and the like), keratin and collagen and derivatives thereof, and similar natural polymer compounds.

The water-swellable clay mineral is an inorganic water-soluble polymer and is a type of colloid-containing aluminum silicate having a three-layer structure. Typical examples thereof are expressed by the formula (A) below.

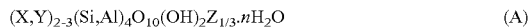

$$(X,Y)_{2-3}(Si,Al)_4O_{10}(OH)_2Z_{1/3} \cdot nH_2O \quad (A)$$

In this formula, X is Al, Fe(III), Mn(III), or Cr(III), Y is Mg, Fe(II), Ni, Zn, or Li, and Z is K, Na, or Ca.

Specific examples of such inorganic water-soluble polymers include bentonite, montmorillonite, beidellite, nontronite, saponite, hectorite, magnesium aluminum silicate, and silicic anhydride, and these may be natural or synthetic products.

An oil agent described above can be used, and one type thereof or two or more types thereof can be used, as necessary.

Examples of the oil-soluble gelling agent include aluminum stearate, magnesium stearate, zinc myristate, and similar metal soaps; N-lauroyl-L-glutamic acid, α,γ-di-n-butylamine, and similar amino acid derivatives; dextrin palmitate, dextrin stearate, dextrin 2-ethylhexanoate palmitate, and similar dextrin fatty acid esters; sucrose palmitate, sucrose stearate, and similar sucrose fatty acid esters; inulin stearate, fructooligosaccharide 2-ethylhexanoate, and similar fructooligosaccharide fatty acid esters; semi-crystalline homo- or co-polymers obtained by the polymerization of a monomer comprising a long chain alkyl acrylate having from 14 to 24 carbons or the like and/or a long chain alkyl methacrylate; monobenzylidene sorbitol, dibenzylidene sorbitol, and similar benzylidene derivatives of sorbitol; dimethylbenzyl dodecylammonium montmorillonite clay, dimethyldioctadecylammonium montmorillonite clay, and similar organo-modified clay minerals; and the like. One type thereof or two or more types thereof can be used, as necessary.

Surfactants other than the components described above can be compounded in the external use preparation or the cosmetic composition of the present invention. In particular, one or two or more surfactants selected from the group consisting of a silicone-based surfactant (other than the liquid organopolysiloxane according to the present invention), an anionic surfactant, a cationic surfactant, a nonionic surfactant, an amphoteric surfactant, and a semipolar surfactant can be used in combination as the surfactant.

The silicone-based surfactant is a silicone-based surfactant other than the liquid organopolysiloxane according to the present invention. The liquid organopolysiloxane according to the present invention has hydrophilic moieties and hydrophobic moieties and, therefore functions as a powder-in-oil dispersing agent. Therefore, when combined with a silicone-based nonionic surfactant, the liquid organopolysiloxane functions as an aid to enhance the stability of the nonionic surfactant, and may improve the overall stability of the formulation. Particularly, the liquid organopolysiloxane according to the present invention can be advantageously used in combination with a glycerin-modified silicone, a sugar-modified silicone, a sugar alcohol-modified silicone, a carboxylic acid-modified silicone, and a polyglycerin-modified silicone elastomer (otherwise known as a polyglycerated silicone elastomer). Moreover, as necessary, a silicone-based nonionic surfactant in which an alkyl branch, a straight chain silicone branch, a siloxane dendrimer branch or the like is provided along with the hydrophilic group can be advantageously used. Note that, while it is possible to combine use with a polyoxyalkylene-modified silicone (a polyether-modified silicone, a fluorine polyether-modified silicone, or the like), a polyether-modified silicone elastomer (also known as a polyoxyalkylated silicone elastomer), or an organopolyoxyalkylene group-containing surfactant, from the perspective of increasing environmental compatibility and changing the entire formulation of the cosmetic composition or the external use preparation to a PEG-FREE formulation, a non-polyether structure surfactant is preferably selected.

Examples of the anionic surfactants include those where carboxylic acid-modified silicone is neutralized using an alkaline substance, saturated or unsaturated fatty acid salts (e.g. sodium laurate, sodium stearate, sodium oleate, sodium linolenate, and the like); alkylsulfuric acid salts; alkylbenzene sulfonic acids (e.g. hexylbenzenesulfonic acid, octylbenzenesulfonic acid, dodecylbenzenesulfonic acid, and the like) and salts thereof; polyoxyalkylene alkyl ether sulfuric acid salts; polyoxyalkylene alkenyl ether sulfuric acid salts; polyoxyethylene alkylsulfuric ester salts; sulfosuccinic acid alkyl ester salts; polyoxyalkylene sulfosuccinic acid alkyl ester salts; polyoxyalkylene alkylphenyl ether sulfuric acid salts; alkanesulfonic acid salts; octyltrimethylammonium hydroxide; dodecyltrimethylammonium hydroxide; alkyl sulfonates; polyoxyethylene alkylphenyl ether sulfuric acid salts; polyoxyalkylene alkyl ether acetic acid salts; alkyl phosphoric acid salts; polyoxyalkylene alkyl ether phosphoric acid salts; acylglutamic acid salts; α-acylsulfonic acid salts; alkylsulfonic acid salts; alkylallylsulfonic acid salts; α-olefinsulfonic acid salts; alkylnaphthalene sulfonic acid salts; alkanesulfonic acid salts; alkyl- or alkenylsulfuric acid salts; alkylamide sulfuric acid salts; alkyl- or alkenyl phosphoric acid salts; alkylamide phosphoric acid salts; alkyloylalkyl taurine salts; N-acylamino acid salts; sulfosuccinic acid salts; alkyl ether carboxylic acid salts; amide ether carboxylic acid salts; α-sulfofatty acid ester salts; alanine derivatives; glycine derivatives; and arginine derivatives. Examples of salts include alkali metal salts such as sodium salts and the like, alkaline earth metal salts such as magnesium salts and the like, alkanolamine salts such as triethanolamine salts and the like, and ammonium salts.

Examples of cationic surfactants include alkyltrimethylammonium chloride, stearyltrimethylammonium chloride, lauryltrimethylammonium chloride, cetyltrimethylammonium chloride, beef tallow alkyltrimethylammonium chloride, behenyltrimethylammonium chloride, stearyltrimethylammonium bromide, behenyltrimethylammonium bromide, distearyldimethylammonium chloride, dicocoyldimethylammonium chloride, dioctyldimethylammonium chloride, di(POE)oleylmethylammonium (2 EO) chloride, benzalkonium chloride, alkyl benzalkonium chloride, alkyl dimethylbenzalkonium chloride, benzethonium chloride, stearyl dimethylbenzylammonium chloride, lanolin derivative quaternary ammonium salt, diethylaminoethylamide stearate, dimethylaminopropylamide stearate, behenic acid amide propyldimethyl hydroxypropylammonium chloride, stearoyl colaminoformyl methylpyridinium chloride, cetylpyridinium chloride, tall oil alkylbenzyl hydroxyethylimidazolinium chloride, and benzylammonium salt.

Examples of nonionic surfactants include polyglyceryl diisostearate and polyhydroxy diglyceryl stearate, isostearyl glyceryl ethers, polyoxyalkylene ethers, polyoxyalkylene alkyl ethers, polyoxyalkylene fatty acid esters, polyoxyalkylene fatty acid diesters, polyoxyalkylene resin acid esters, polyoxyalkylene (hydrogenated) castor oils, polyoxyalkylene alkyl phenols, polyoxyalkylene alkyl phenyl ethers, polyoxyalkylene phenyl phenyl ethers, polyoxyalkylene alkyl esters, polyoxyalkylene alkyl esters, sorbitan fatty acid esters, polyoxyalkylene sorbitan alkyl esters, polyoxyalkylene sorbitan fatty acid esters, polyoxyalkylene sorbitol fatty acid esters, polyoxyalkylene glycerol fatty acid esters, polyglycerol alkyl ethers, polyglycerol fatty acid esters, sucrose fatty acid esters, fatty acid alkanolamides, alkylglucosides, polyoxyalkylene fatty acid bisphenyl ethers, polypropylene glycol, diethyleneglycol, fluorine-based surfactants, and the like.

Examples of amphoteric surfactants include imidazoline-type, amidobetaine-type, alkylbetaine-type, alkylamidobetaine-type, alkylsulfobetaine-type, amidosulfobetaine-type, hydroxysulfobetaine-type, carbobetaine-type, phosphobetaine-type, aminocarboxylic acid-type, and amidoamino acid-type amphoteric surfactants. Specifically, imidazoline-type amphoteric surfactants such as 2-undecyl-N,N,N-(hydroxyethylcarboxymethyl)-2-imidazoline sodium, 2-cocoyl-2-imidazolinium hydroxide-1-carboxyethyloxy disodium salt, and the like; alkylbetaine-type amphoteric surfactants such as lauryl dimethylaminoacetic betaine, myristyl betaine, and the like; amidobetaine-type amphoteric surfactants such as coconut oil fatty acid amidopropyl dimethylamino acetic acid betaine, palm kernel oil fatty acid amidopropyl dimethylamino acetic acid betaine, beef tallow fatty acid amidopropyl dimethylamino acetic acid betaine, hardened beef tallow fatty acid amidopropyl dimethylamino acetic acid betaine, lauric acid amidopropyl dimethylamino acetic acid betaine, myristic acid amidopropyl dimethylamino acetic acid betaine, palmitic acid amidopropyl dimethylamino acetic acid betaine, stearic acid amidopropyl dimethylamino acetic acid betaine, oleic acid amidopropyl dimethylamino acetic acid betaine, and the like; alkylsulfobetaine-type amphoteric surfactants such as coconut oil fatty acid dimethyl sulfopropyl betaine and the like; alkyl hydroxy sulfobetaine-type amphoteric surfactants such as lauryl dimethylaminohydroxy sulfobetaine and the like; phosphobetaine-type amphoteric surfactants such as lauryl-hydroxy phosphobetaine and the like; and amidoamino acid-type amphoteric surfactants such as sodium N-lauroyl-N'-hydroxyethyl-N'-carboxymethyl ethylenediamine, sodium N-oleoyl-N'-hydroxyethyl-N'-carboxymethyl ethylenediamine, sodium N-cocoyl-N'-hydroxyethyl-N'-carboxymethyl ethylenediamine, potassium N-lauroyl-N'-hydroxyethyl-N'-carboxymethyl ethylenediamine, potassium N-oleoyl-N'-hydroxyethyl-N'-carboxymethyl ethylenediamine, sodium N-lauroyl-N-hydroxyethyl-N'-carboxymethyl ethylenediamine, sodium N-oleoyl-N-hydroxyethyl-N'-carboxymethyl ethylenediamine, sodium N-cocoyl-N-hydroxyethyl-N'-carboxymethyl ethylenediamine, monosodium N-lauroyl-N-hydroxyethyl-N',N'-dicarboxymethyl ethylenediamine, monosodium N-oleoyl-N-hydroxyethyl-N',N'-dicarboxymethyl ethylenediamine, monosodium N-cocoyl-N-hydroxyethyl-N',N'-dicarboxymethyl ethylenediamine, disodium N-lauroyl-N-hydroxyethyl-N,N'-dicarboxymethyl ethylenediamine, disodium N-oleoyl-N-hydroxyethyl-N',N'-dicarboxymethyl ethylenediamine, disodium N-cocoyl-N-hydroxyethyl-N',N'-dicarboxymethyl ethylenediamine, and the like.

Examples of semipolar surfactants include alkylamine oxide-type surfactants, alkylamine oxides, alkylamide amine oxides, alkylhydroxyamine oxides, and the like. Alkyldimethylamine oxides having from 10 to 18 carbons, alkoxyethyl dihydroxyethylamine oxides having from 8 to 18 carbons, and the like are preferably used. Specific examples thereof include dodecyldimethylamine oxide, dimethyloctylamine oxide, diethyldecylamine oxide, bis-(2-hydroxyethyl)dodecylamine oxide, dipropyltetradecylamine oxide, methylethylhexadecylamine oxide, dodecylamidopropyldimethylamine oxide, cetyldimethylamine oxide, stearyldimethylamine oxide, tallow dimethylamine oxide, dimethyl-2-hydroxyoctadecylamine oxide, lauryldimethylamine oxide, myristyldimethylamine oxide, stearyldimethylamine oxide, isostearyldimethylamine oxide, coconut fatty acid alkyldimethylamine oxide, caprylic amide propyldimethylamine oxide, capric amide propyldimethylamine oxide, lauric amide propyldimethylamine oxide, myristic amide propyldimethylamine oxide, palmitic amide propyldimethylamine oxide, stearic amide propyldimethylamine oxide, isostearic amide propyldimethylamine oxide, oleic amide propyldimethylamine oxide, ricinoleic amide propyldimethylamine oxide, 12-hydroxystearic amide propyldimethylamine oxide, coconut fatty acid amide propyldimethylamine oxide, palm kernel oil fatty acid amide propyldimethylamine oxide, castor oil fatty acid amide propyldimethylamine oxide, lauric amide ethyldimethylamine oxide, myristic amide ethyldimethylamine oxide, coconut fatty acid amide ethyldimethylamine oxide, lauric amide ethyldiethylamine oxide, myristic amide ethyldiethylamine oxide, coconut fatty acid amide ethyldiethylamine oxide, lauric amide ethyldihydroxyethylamine oxide, myristic amide ethyldihydroxyethylamine oxide, and coconut fatty acid amide ethyldihydroxyethylamine oxide.

The ultraviolet light blocking agent can be an inorganic ultraviolet light blocking agent or an organic ultraviolet light blocking agent. When the external use preparation or the cosmetic composition of the present invention is to be used for sunblocking, at least one type of organic ultraviolet light blocking agent is preferably comprised. In particular, using both inorganic and organic ultraviolet light blocking agents is preferable, and using a UV-A blocking agent in combination with a UV-B blocking agent is more preferable.

The inorganic ultraviolet light blocking agent may be compounded as an ultraviolet light scattering agent such as the inorganic pigment powders and metal powder pigments mentioned above. Examples thereof include metal oxides such as titanium oxide, zinc oxide, cerium oxide, titanium suboxide, iron-doped titanium oxides, and the like; metal hydroxides such as iron hydroxides and the like; metal flakes such as platy iron oxide, aluminum flake, and the like; and ceramics such as silicon carbide, and the like. Among these, at least one type of a material selected from fine particulate metal oxides and fine particulate metal hydroxides with an average particle size ranging from 1 to 100 nm in the form of granules, plates, needles, or fibers is, in particular, preferred. The powder is preferably subjected to, for example, a conventional surface treatment such as fluorine compound treatments, of which a perfluoroalkyl phosphate treatment, a perfluoroalkylsilane treatment, a perfluoropolyether treatment, a fluorosilicone treatment, or a fluorinated silicone resin treatment is preferable; silicone treatments, of which a methylhydrogenpolysiloxane treatment, a dimethylpolysiloxane treatment, a vapor-phase tetramethyltetrahydrogen cyclotetrasiloxane treatment, or a glycerin-modified silicone treatment is preferable; silicone resin treatments, of which a trimethylsiloxysilicic acid treatment is preferable; pendant treatments which are methods of adding alkyl chains after a vapor-phase silicone treatment; silane coupling agent treatments; titanium coupling agent treatments; silane treatments, of which an alkylsilane treatment, or an alkylsilazane treatment is preferable; oil agent treatments; N-acylated lysine treatments; polyacrylic acid treatments; metallic soap treatments in which a stearic acid or a myristic acid salt is preferably used; acrylic resin treatments; metal oxide treatments; and the like. Multiple treatments described above are preferably performed. For example, the surface of the fine particulate titanium oxide can be coated with a metal oxide such as silicon oxide, alumina or the like, and then, a surface treatment with an alkylsilane can be carried out. A total amount of the surface treatment agent is preferably in a range from 0.1 to 50 wt. % of the powder.

The organic ultraviolet light blocking agent is a lipophilic ultraviolet light blocking agent, and examples thereof include benzoic acid-based UV absorbers such as paraminobenzoic acid (hereinafter, referred to as "PABA"), PABA monoglycerol ester, N,N-dipropoxy-PABA ethyl ester, N,N-diethoxy-PABA ethyl ester, N,N-dimethyl-PABA ethyl ester, N,N-dimethyl-PABA butyl ester, 2-[4-(diethylamino)-2-hydroxybenzoyl]hexylester benzoate (trade designation: Uvinul A plus) and the like; anthranilic acid-based UV absorbers such as homomethyl-N-acetylanthranilate and the like; salicylic acid-based UV absorbers such as amyl salicylate, menthyl salicylate, homomethyl salicylate, octyl salicylate, phenyl salicylate, benzyl salicylate, p-isopropanolphenyl salicylate, and the like; cinnamic acid-based UV absorbers such as octyl cinnamate, ethyl-4-isopropylcinnamate, methyl-2,5-diisopropylcinnamate, ethyl-2,4-diisopropylcinnamate, methyl-2,4-diisopropylcinnamate, propyl-p-methoxycinnamate, isopropyl p-methoxycinnamate, iso-amyl-p-methoxycinnamate, octyl-p-methoxycinnamate (2-ethylhexyl-p-methoxycinnamate), 2-ethoxyethyl-p-methoxycinnamate, cyclohexyl-p-methoxy cinnamate, ethyl-α-cyano-β-phenylcinnamate, 2-ethylhexyl-α-cyano-β-phenylcinnamate, glyceryl mono-2-ethylhexanoyl-di-paramethoxycinnamate, 3-methyl-4-[methylbis(trimethylsiloxy) silyl]butyl 3,4,5-trimethoxycinnamate, dimethicodiethyl benzalmalonate (trade designation: Parsol SLX (INCI name: Polysilicone-15)), and the like; benzophenone-based UV absorbers such as 2,4-dihydroxybenzophenone, 2,2'-dihydroxy-4-methoxybenzophenone, 2,2'-dihydroxy-4,4'-dimethoxybenzophenone, 2,2',4,4'-tetrahydroxybenzophenone, 2-hydroxy-4-methoxybenzophenone, 2-hydroxy-4-methoxy-4'-methylbenzophenone, 2-hydroxy-4-methoxybenzophenone-5-sulfonate, 4-phenylbenzophenone, 2-ethylhexyl-4'-phenylbenzophenone-2-carboxylate, hydroxy-4-n-octoxybenzophenone, 4-hydroxy-3-carboxybenzophenone, and the like; benzotriazole-based UV absorbers such as 3-(4'-methylbenzylidene)-d,l-camphor, 3-benzylidene-d,l-camphor, urocanic acid, urocanic acid ethyl ester, 2-phenyl-5-methylbenzoxazole, 2,2'-hydroxy-5-methylphenyl benzotriazole, 2-(2'-hydroxy-5'-t-octylphenyl)benzotriazole, 2-(2'-hydroxy-5'-methylphenyl)benzotriazole, dibenzaladine, dianisoylmethane, 4-methoxy-4'-t-butyldibenzoylmethane, 5-(3,3-dimethyl-2-norbornylidene)-3-pentan-2-one, 2,2'-methylene bis(6-(2H-benzotriazole-2-yl)-4-(1,1,3,3-tetramethylbutyl)phenol) (trade designation: Tinosorb® M); triazine-based UV absorbers such as 2,4,6-tris[4-(2-ethylhexyloxycarbonyl)anilino]1,3,5-triazine (INCI: octyltriazone), 2,4-bis{[4-(2-ethyl-hexyloxy)-2-hydroxyl]phenyl}-6-(4-methoxyphenyl)-1,3,5-triazine (INCI: bis-ethylhexyloxyphenol methoxyphenyl triazine, trade designation: Tinosorb® S), and the like; 2-cyano-3,3-diphenylprop-2-enoate-2-ethylhexyl ester (INCI: octocrylene); and the like. Because organic-based UV absorbers generally have high polarities and do not readily dissolve, it has been difficult in the past to stably compound a desired high amount of an organic-based UV absorber in a water-in-oil (W/O) emulsion cosmetic composition. However, when using the liquid organopolysiloxane of the present invention as an emulsifier and, when a medium polarity oil such as an ester oil or the like is combined therewith as a binding agent, a stable UV absorber-containing W/O emulsion cosmetic composition can be obtained even when the oil phase includes a low polarity oil such as a silicone oil, a hydrocarbon oil, or the like. In this case, the compounded amount of the organic-based UV absorber is preferably in a range of 0.1 to 10 wt. % and the compounded amount of the binding agent is preferably in a range of 0.005 to 5 wt. %.

Additionally, it is possible to use a product in which the organo-ultraviolet light blocking agent is comprised in a hydrophobic polymer powder. The polymer powder may be hollow or not, may have an average primary particle size thereof ranging from 0.1 to 50 μm and may have a particle size distribution thereof of either broad or sharp. Types of polymer include acrylic resins, methacrylic resins, styrene resins, polyurethane resins, polyethylene, polypropylene, polyethylene terephthalate, silicone resins, nylons, acrylamide resins, and silylated polypeptide resins. A polymer powder comprising from 0.1 to 30 wt. % of an organic ultraviolet light blocking agent is preferable, and a polymer powder comprising 4-tert-butyl-4'-methoxydibenzoylmethane, which is a UV-A absorber, is particularly preferable.

An ultraviolet light blocking agent that can be preferably used is at least one selected from the group consisting of fine particulate titanium oxide, fine particle zinc oxide, paramethoxy cinnamic acid 2-ethylhexyl, 4-tert-butyl-4'-methoxydibenzoylmethane, a benzotriazole-based UV absorber, and a triazine-based UV absorber. These ultraviolet light blocking agents are generally used, are easy to acquire, and have high ultraviolet light blocking effects and, thus can be beneficially used.

Examples of salts include inorganic salts, organic salts, amine salts, and amino acid salts. Examples of inorganic salts include sodium salts, potassium salts, magnesium salts, calcium salts, aluminum salts, zirconium salts, zinc salts, and the like of hydrochloric acid, sulfuric acid, carbonic acid, nitric acid, and similar inorganic acids. Examples of organic acid salts include salts of acetic acid, dehydroacetic acid, citric acid, malic acid, succinic acid, ascorbic acid, stearic acid, and similar organic acids. Examples of amine salts and amino acid salts include triethanolamine and similar salts of amines, glutamic acid and similar salts of amino acids, and the like. Additionally, salts of hyaluronic acid, chondroitin sulfuric acid, and the like, aluminum zirconium glycine complexes and the like, and acid-alkali neutralization salts and the like used in cosmetic product formulations can be used.

Examples of moisturizing agents include glycerin, sorbitol, propylene glycol, dipropylene glycol, 1,3-butylene glycol, glucose, xylitol, maltitol, polyethyleneglycol, and similar polyhydric alcohols; hyaluronic acid, chondroitin sulfuric acid, pyrrolidone carboxylic acid salt, polyoxyethylene methylglucoside, polyoxypropylene methylglucoside, PEG/PPG dimethylether, polyols, glycols, glycol esters, and the like. However, from the perspective of increasing environmental compatibility and changing the entire formulation of the cosmetic composition or the external use preparation to a PEG-FREE formulation, a non-polyether water-soluble polymer is preferably selected.

Examples of preservatives include alkyl paraoxybenzoates, benzoic acid, sodium benzoate, sorbic acid, potassium sorbate, phenoxyethanol, and the like. Examples of antimicrobial agents include benzoic acid, salicylic acid, carbolic acid, sorbic acid, alkyl paraoxybenzoates, parachlorometha-cresol, hexachlorophene, benzalkonium chloride, chlorhexidine chloride, trichlorocarbanilide, triclosan, photosensitizers, phenoxyethanol, and the like. However, in cases where the cosmetic composition is a rouge, it is preferable that these are not included.

Examples of the antioxidants include tocopherol, butylhydroxyanisole, dibutylhydroxytoluene, phytic acid, and the like.

Examples of pH adjusting agents include lactic acid, citric acid, glycolic acid, succinic acid, tartaric acid, dl-malic acid, potassium carbonate, sodium hydrogen carbonate, ammonium hydrogen carbonate, and the like.

Examples of the chelating agent include alanine, sodium salt of edetic acid, sodium polyphosphate, sodium metaphosphate, phosphoric acid, and the like.

Examples of the refreshing agents include L-menthol, camphor, and the like. Examples of the anti-inflammatory agents include allantoin, glycyrrhetic acid, glycyrrhizinic acid, tranexamic acid, azulene, and the like.

Examples of skin beautifying components include skin-lightening agents such as placenta extracts, arbutin, glutathione, saxifrageous extracts, and the like; cell activating agents such as royal jelly and the like; agents for ameliorating skin roughness; circulation promoters such as nonylic acid vanillylamide, benzyl nicotinate, beta-butoxyethyl nicotinate, capsaicin, zingerone, cantharide tincture, ichthammol, caffeine, tannic acid, α-borneol, tocopherol nicotinate, inositol hexanicotinate, cyclandelate, cinnarizine, tolazoline, acetylcholine, verapamil, cepharanthine, γ-oryzanol, and the like; astringents such as zinc oxide, tannic acid, and the like; antiseborrheic agents such as sulfur, thianthol, and the like; and the like. Examples of vitamins include vitamin As such as vitamin A oil, retinol, retinol acetate, retinol palmitate, and the like; vitamin Bs such as vitamin B2s such as riboflavin, riboflavin butyrate, flavin adenine dinucleotide, and the like; vitamin B6s such as pyridoxine hydrochloride, pyridoxine dioctanoate, pyridoxine tripalmitate, and the like; vitamin B12 and derivatives thereof; vitamin B15 and derivatives thereof, and the like; vitamin Cs such as L-ascorbic acid, L-ascorbyl dipalmitic acid esters, sodium L-ascorbyl 2-sulfate, dipotassium L-ascorbyl phosphoric acid diester, and the like; vitamin Ds such as ergocalciferol, cholecalciferol, and the like; vitamin Es such as α-tocopherol, β-tocopherol, γ-tocopherol, dl-α-tocopherol acetate, dl-α-tocopherol nicotinate, dl-α-tocopherol succinate, and the like; vitamin H; vitamin P; nicotinic acids such as nicotinic acid, benzyl nicotinate, and the like; pantothenic acids such as calcium pantothenate, D-pantothenyl alcohol, pantothenyl ethyl ether, acetyl pantothenyl ethyl ether, and the like; and the like.

Examples of amino acids include amino acids such as glycine, valine, leucine, isoleucine, serine, threonine, phenylalanine, arginine, lysine, aspartic acid, glutamic acid, cystine, cysteine, methionine, tryptophan, pyrrolidone carboxylic acid, and the like, and/or salts thereof.

Examples of nucleic acids include deoxyribonucleic acid and the like. Examples of hormones include estradiol, ethenyl estradiol, and the like.

The bioactive component is a substance that imparts some sort of bioactivity to the skin or the hair when applied on the skin or to the hair, and examples thereof include lipophilic substances. Examples thereof include anti-inflammatory agents, anti-aging agents, tightening agents, hair regrowth agents, hair growth promoters, moisturizing agents, circulation promoters, drying agents, warming agents, vitamins, wound healing accelerators, irritation mitigation agents, analgesics, cell activating agents, enzyme components, and the like. Likewise, natural vegetable extract components, seaweed extract components and herbal medicine components can be preferably blended.

The medicament active component include substances that have disorder treatment benefits, and examples thereof include proteins, peptides, and low molecular weight compounds.

The perfume is not particularly limited provided that it is a lipophilic perfume, and examples thereof include perfumes that contain a variety of extracts and are extracted from a variety of plant flowers, seeds, leaves, roots, and the like, perfumes extracted from seaweed, perfumes extracted from a variety of animal parts and secretions (for example, musk or sperm oil), and artificially synthesized perfumes (for example, menthol, musk, acetic acid esters, and vanilla). The perfume is compounded for the purpose of imparting a fragrance or scent to the external use preparation or the cosmetic composition. Examples of the pigment include oil soluble dyes, water soluble dyes, extender pigments, inorganic pigments, organic pigments, lipophilic optical brighteners, and the like.

Combinations with Other Silicone-Based Cosmetic Raw Materials

Depending on the dosage form and formulation thereof, the external use preparation or the cosmetic composition according to the present invention may further comprise a solid silicone resin or crosslinking organopolysiloxane, an acryl silicone dendrimer copolymer, a silicone raw rubber (silicone gum), a polyamide-modified silicone, an alkyl-modified silicone wax, or an alkyl-modified silicone resin wax. The liquid organopolysiloxane of the present invention is configured so as to have a polysiloxane chain or the like constituting the main chain and a hydrophilic glycerin derivative group as a modifying group, and, optionally, may have a long chain alkyl group or the like. This is advantageous because a cosmetic composition can be designed that has superior compounding stability with these silicone-based compounds, and that takes advantage of the tactile sensation that is characteristic of these silicone-based cosmetic raw materials.

Solid Silicone Resin or Crosslinking Organopolysiloxane

The external use preparation or the cosmetic composition of the present invention can further comprise a solid silicone resin or crosslinking organopolysiloxane. The solid silicone resin or crosslinking organopolysiloxane is preferably hydrophobic so that it is completely insoluble in water at room temperature or the solubility thereof with respect to 100 g of water is below 1 wt. % (mass %). The solid silicone resin is commonly used as a film-forming polymer that is compoundable in oil systems.

The solid silicone resin is an organopolysiloxane having a highly branched structure, a reticulated structure, or a cage structure, and is solid at room temperature. Any type of product may be used, provided that it is a silicone resin that is commonly used in cosmetic compositions and does not oppose the object of the present invention. In the case of a solid silicone resin, the silicone resin may be in the form of particles such as spherical powders, scale powders, needle powders platy flake powders (including platy powders having an aspect ratio of particles and the outer appearance which are generally understood as a plate form) or the like. In particular, silicone resin powders containing a monoorganosiloxy unit (T unit) and/or a siloxy unit (Q unit) described below are preferably used. From the perspective of ease of compounding, the solid silicone resin is preferably used in a form where the solid silicone resin is dissolved in a cyclic silicone or low viscosity chain silicone or the like.

Compounding the liquid organopolysiloxane of the present invention along with the solid silicone resin (or the resin solution) is useful because compatibility with the oil agent and uniform dispersibility are improved, improvement effects in sensation during use can be obtained, namely uniform adhesion to the applied area due to the compounding of the solid silicone resin, and improvement effects in cosmetic retainability can be obtained such as moisture resistance, sebum resistance, and the like.

Examples of the solid silicone resin include MQ resins, MDQ resins, MTQ resins, MDTQ resins, TD resins, TQ resins, and TDQ resins formed from arbitrary combinations of triorganosiloxy units (M units) (where the organo groups are only methyl groups, or are methyl groups and vinyl groups or phenyl groups), diorganosiloxy units (D units) (where the organo groups are only methyl groups, or are methyl groups and vinyl groups or phenyl groups), monoorganosiloxy units (T units) (where the organo groups are methyl groups, vinyl groups, or phenyl groups), and siloxy units (Q units). In addition, as other examples thereof, mention may be made of trimethylsiloxysilicic acid, polyalkylsiloxysilicic acid, trimethylsiloxysilicic acid containing dimethylsiloxy units and alkyl(perfluoroalkyl) siloxysilicic acid. These silicone resins are preferably oil soluble and can be dissolved in volatile silicone.

Particularly, a phenyl silicone resin having a high refractive index and a high content of phenyl groups (e.g. 217 Flake resin and the like, manufactured by Dow Corning Toray Co., Ltd.) can be easily used as a flaky silicone resin powder and, when compounded in a cosmetic composition, can impart a radiant feeling of sheerness to the skin or the hair.

The organopolysiloxane chain of the crosslinking organopolysiloxane preferably has a three-dimensionally crosslinked structure, obtained by reacting a polyether unit, a glycerin unit, a crosslinking component or the like formed from an alkylene unit having from 4 to 20 carbons or an organopolysiloxane unit, and other optional modifying agents and the like. However, from the perspective of increasing environmental compatibility and changing the entire formulation of the cosmetic composition or the external use preparation to a PEG-FREE formulation, a non-PEG crosslinking organopolysiloxane is preferably selected. Note that hydrophilic group free crosslinking organopolysiloxanes are also called non-emulsifying silicone elastomers.

Specifically, the crosslinking organopolysiloxane can be obtained via an addition reaction of an organohydrogenpolysiloxane having a silicon-bonded hydrogen atom, a polyether compound or glycerin derivative having reactive unsaturated groups at both terminals of the molecular chain, an unsaturated hydrocarbon having more than one double bond in the molecule, and an organopolysiloxane having more than one double bond in the molecule.

Here, the crosslinking organopolysiloxane may have or may be free of unreacted silicon-bonded hydrogen atoms, phenyl groups, and similar aromatic hydrocarbon groups; octyl groups and similar long chain alkyl groups having from 6 to 30 carbons; polyether groups, carboxyl groups, and similar modifying functional groups. In other words, any crosslinking organopolysiloxane can be used without limitations to physical modes or preparation methods such as dilution, properties, and the like.

As one example, the aforementioned crosslinking organopolysiloxane can be obtained by addition-reacting an organohydrogenpolysiloxane which is formed from a structure unit selected from the group consisting of a $SiO_2$ unit, a $HSiO_{1.5}$ unit, a $R^b SiO_{1.5}$ unit, a $R^b HSiO$ unit, a $R^b{}_2 SiO$ unit, a $R^b{}_3 SiO_{0.5}$ unit and a $R^b{}_2 HSiO_{0.5}$ unit, wherein $R^b$ is a substituted or non-substituted monovalent hydrocarbon group having 1 to 30 carbon atoms, excluding an aliphatic unsaturated group, and a part of Rb is a monovalent hydrocarbon group having 8 to 30 carbon atoms, and at the same time, includes 1.5 or more, on average, of hydrogen atoms binding to the silicon atom in the molecule, with a crosslinking component selected from the group consisting of a polyoxyalkylene compound having unsaturated hydrocarbon groups at both terminals of the molecular chain, a polyether compound such as a polyglycerol compound, a polyglycidyl ether compound or the like, an unsaturated hydrocarbon which is an α,ω-diene represented by the following general formula: $CH_2=CH-C_rH_{2r}-CH=CH_2$, wherein r is an integer ranging from 0 to 26, and an organopolysiloxane which is formed from a $SiO_2$ unit, a $(CH_2=CH)SiO_{1.5}$ unit, a $R^c SiO_{1.5}$ unit, a $R^c(CH_2=CH)SiO$ unit, a $R^c{}_2 SiO$ unit, a $R^c{}_3 SiO_{0.5}$, and a $R^c{}_2(CH_2=CH)SiO_{0.5}$, wherein $R^c$ is a substituted or non-substituted monovalent hydrocarbon group having 1 to 30 carbon atoms, excluding an aliphatic unsaturated group, and includes 1.5 or more, on average, of vinyl groups binding to the silicon atom. Note that by addition reacting the unreacted silicon-bonded hydrogen atoms, the modifying functional groups described above can be introduced. For example, by reacting 1-hexene with a crosslinking organopolysiloxane having unreacted silicon-bonded hydrogen atoms, hexyl groups (C6 alkyl groups) are introduced.

Any crosslinking organopolysiloxane can be used without limitations to physical modes or preparation methods such as dilution, properties, and the like, provided that it is a crosslinking organopolysiloxane such as that described above. Particularly preferable examples thereof include α,ω-diene crosslinking silicone elastomers (commercially available products include DC 9040 Silicone Elastomer Blend, DC 9041 Silicone Elastomer Blend, DC 9045 Silicone Elastomer Blend, DC 9046 Silicone Elastomer Blend, EL-9140 DM Silicone Elastomer Blend, 9546 Silicone Elastomer Blend, 9027 Silicone Elastomer Blend, FB-9586 Silicone Elastomer Blend, and EL-8040 ID Silicone Organic Blend, manufactured by Dow Corning Corporation, in the USA) described in U.S. Pat. No. 5,654,362. Additionally, examples of partial crosslinking organopolysiloxane polymers include by International Nomenclature Cosmetic Ingredient (INCI) labeling names, (dimethicone/vinyldimethicone) crosspolymers, (dimethicone/phenylvinyldimethicone) crosspolymers, (PEG-8 to 30/C6 to C30 alkyldimethicone) crosspolymers, (vinyldimethicone/C6 to C30 alkyldimethicone) crosspolymers, (dimethicone/polyglycerin) crosspolymers, and the like.

Examples of other preferable crosslinking organopolysiloxanes include silicone polyether elastomer gel that display increased compatibility with various organic components and stable thickening effects due to the introduction of polyoxypropylene groups (commercially available products include Dow Corning EL-8050 ID SILICONE ORGANIC ELASTOMER BLEND, Dow Corning EL-8051 IN SILICONE ORGANIC ELASTOMER BLEND, and Dow Corning EL-7040 HYDRO ELASTOMER BLEND) described in WO2007/109240 and WO2009/006091; and the pituitous silicone fluids described in WO2011/028765 and WO2011/028770. Furthermore, the liquid and slightly crosslinkable organopolysiloxane filed in Japan (as patent application 2010-289722) by the present applicant, and for which priority rights are claimed based on said application can be used in the present invention.

In the case of a non-emulsifiable crosslinking organopolysiloxane (also called a non-emulsifying silicone elastomer), formed by crosslinking by means of an unsaturated hydrocarbon such as an unsaturated group-containing organopolysiloxane, a diene, and the like, or a polyoxypropylene having reactive unsaturated groups at both molecular terminals being compounded as a component in the external use preparation or the cosmetic composition, a thick, smooth tactile sensation can be imparted to the skin or the hair and a matte finish and effects of concealing wrinkles, pigmented spots, and the like can be obtained. Furthermore, such a configuration is advantageous because the feel of adhesion to the skin of the cosmetic composition is improved and cosmetic retainability is enhanced because the effects of retaining various oil agents and increasing the viscosity is high.

The non-emulsifying crosslinking organopolysiloxane has the superior characteristics unique thereto of sensation during use, concealing, and the like as described above but, because it does not comprise a hydrophilic group, there have been cases where stable compounding in water-containing cosmetic compositions and external use preparations has been difficult. However, if the liquid organopolysiloxane of the present invention is used as an emulsifier for a water-in-oil or polar solvent-in-oil emulsion, even in cases where the crosslinking organopolysiloxane is comprised in the oil phase, it will be possible to obtain an emulsion-type cosmetic composition or external use preparation with stability that is superior to that of conventional emulsifiers.

On the other hand, emulsifying crosslinking organopolysiloxanes (also called emulsifying silicone elastomers) have the unique properties of the crosslinking organopolysiloxanes described above and, at the same time, function to a certain degree as an emulsifier for a water-in-oil or polar solvent-in-oil emulsion. Conventional crosslinking organopolysiloxanes having a PEG portion can provide a stable W/O emulsion, but the oiliness and stickiness upon drying that are particular to PEG are problems. Additionally, conventional crosslinking organopolysiloxanes do not comply with the global trend for changing the entire formulation of end consumer products such as cosmetic products and the like to PEG-FREE formulations.

In contrast, while the problem with the tactile sensation, namely the oiliness, of conventional crosslinking organopolysiloxanes comprising a glycerin derivative is reduced compared to the PEG types, stability of a W/O emulsion is extremely poor, particularly with respect to oil phases that comprise organic oils and said conventional crosslinking organopolysiloxanes comprising a glycerin derivative cannot function alone as an emulsifier. Therefore, it has been necessary to combine use with a polyether-modified silicone or similar PEG emulsifier. That is, conventional crosslinking organopolysiloxanes comprising a glycerin derivative, when it comes down to it, are not able to comply with the global trend for changing the entire formulation of end consumer products such as cosmetic products and the like to PEG-FREE formulations.

However, if a technique is used in which the liquid organopolysiloxane of the present invention is used as the base compound of an emulsifier for a water-in-oil or a polar solvent-in-oil emulsion, and a conventional crosslinking organopolysiloxane comprising a glycerin derivative is used as an emulsification aid or as a tactile sensation adjusting agent, stability and high-level sensation during use of the emulsion and lasting moisturizing effects can both be obtained. Therefore, design of a product that complies with the global trend for changing the entire formulation of end consumer products such as cosmetic products and the like to PEG-FREE formulations is possible.

One or two or more types of the solid silicone resin or crosslinking organopolysiloxane can be compounded depending on the purpose thereof. A compounded amount thereof is preferably in a range from 0.05 to 25 wt. % (mass %) and more preferably in a range from 0.1 to 15 wt. % (mass %) of the entire external use preparation or the cosmetic composition, depending on purpose and compounding intention.

Acryl Silicone Dendrimer Copolymer

The external use preparation or the cosmetic composition of the present invention can further comprise an acryl silicone dendrimer copolymer. The acryl silicone dendrimer copolymer is a vinyl polymer having a carbosiloxane dendrimer structure on the sidechain, and preferable examples thereof include the vinyl polymer described in Japanese Patent No. 4009382 (Japanese Unexamined Patent Application Publication No. 2000-063225). Examples of commercially available products include FA 4001CM Silicone Acrylate and FA 4002 ID Silicone Acrylate (manufactured by Dow Corning Toray Co., Ltd.), and the like, and also acryl silicone dendrimer copolymers having a long chain alkyl group on the sidechain or the like having from 8 to 30 carbons and preferably from 14 to 22 carbons. When compounding the acryl silicone dendrimer copolymer alone, superior film formability can be obtained. Therefore, by compounding the acryl silicone dendrimer copolymer in the external use preparation or the cosmetic composition according to the present invention, a strong coating film can be formed on the applied part, and cosmetic durability such as sebum resistance, rubbing resistance, and the like can be significantly improved. The diluent may be a silicone-based oil agent, or an isododecane or a similar organic oil agent.

By using the liquid organopolysiloxane of the present invention together with the aforementioned acryl silicone dendrimer copolymer, there are advantages in that a surface protective property such as sebum resistance can be improved due to strong water repellency provided by the carbosiloxane dendrimer structure, and at the same time, irregularities such as pores can be effectively concealed. Additionally, the liquid organopolysiloxane of the present invention causes the acryl silicone dendrimer copolymer to blend excellently with the other oil agents and has excellent compatibility with the skin and surface of the hair. Therefore, hardness of the acryl silicone dendrimer copolymer can be lessened, and a film with superior adhesive sensation and a lasting feel of moisture can be achieved. Additionally, cosmetic retainability is maintained and moisturizing effects are imparted and, therefore there is an advantage in that degradation of the skin surface or the hair can be suppressed for an extended period of time.

A compounded amount of the acryl silicone dendrimer copolymer can be suitably selected based on the purpose and compounding intent thereof, but is preferably in a range from 1 to 99 wt. % (mass %) and more preferably in a range from 30 to 70 wt. % (mass %) of the entire external use preparation or cosmetic composition.

Silicone Raw Rubber (Silicone Gum)

In the external use preparation or the cosmetic composition of the present invention, an ultra-high viscous yet fluid component having a viscosity at room temperature of 1,000,000 mm$^2$/s or higher, referred to as a silicone raw rubber (silicone gum), can be suitably used as the silicone oil. The silicone gum is a linear diorganopolysiloxane having an ultra-high degree of polymerization, and is also referred to as a silicone raw rubber or an organopolysiloxane gum. The silicone gum possesses a high degree of polymerization, and for this reason, it has a measurable degree of plasticity. In view of this, the silicone gum is different from the aforementioned oil silicones. This silicone gum can be compounded as-is in the external use preparation or the cosmetic composition of the present invention, particularly in a hair cosmetic composition for the purpose of imparting a desired tactile sensation, or alternately can be compounded as a liquid gum dispersion in which an oil-like silicone is dispersed (oil dispersion of the silicone gum).

Examples of such a silicone raw rubber include substituted or unsubstituted organopolysiloxanes having a dialkylsiloxy unit (D unit) such as a dimethylpolysiloxane, a methylphenylpolysiloxane, an aminopolysiloxane, a methylfluoroalkylpolysiloxane, or the like, or products having micro crosslinked structures thereof. Typical examples thereof include products expressed by the general formula: R10(CH3)2SiO{(CH3)2SiO}s{(CH$_3$)R12SiO}tSi(CH3)2R10. In this formula, R12 is a group selected from a vinyl group, a phenyl group, an alkyl group having from 6 to 20 carbons, an aminoalkyl group having from 3 to 15 carbons, a perfluoroalkyl group having from 3 to 15 carbons, and a quaternary ammonium salt group-containing alkyl group having from 3 to 15 carbons; and the terminal group R10 is a group selected from an alkyl group having from 1 to 8 carbons, a phenyl group, a vinyl group, an aminoalkyl group having from 3 to 15 carbons, a hydroxyl group, and an alkoxy group having from 1 to 8 carbons. s=2,000 to 6,000; t=0 to 1,000; and s+t=2,000 to 6,000. Among these, a dimethylpolysiloxane raw rubber having a degree of polymerization ranging from 3,000 to 20,000 is preferred. In addition, an amino-modified methylpolysiloxane raw rubber having a 3-aminopropyl group, an N-(2-aminoethyl)-3-aminopropyl group or the like on the side chain or the terminal of the molecule is preferred. In addition, in the present invention, the silicone gum can be used alone or in combination with two or more types thereof, as necessary.

The silicone gum has an ultra-high degree of polymerization. For this reason, the silicone gum can exhibit a superior retention property on hair or skin, and can form a protective film with a superior aeration property. For this reason, the silicone gum is a component which can particularly provide glossiness and luster on hair and can impart a texture with tension on the entire hair during use and after use. The silicone gum with a high degree of polymerization can be compounded in the external use preparation or the cosmetic composition in a reduced viscosity form obtained by dilution using a silicone oil. Furthermore, as a result of using the liquid organopolysiloxane of the present invention, wet hair such as that when rinsing can be provided with a smooth, sliding feeling; lasting moisturizing effects, protection of the hair surface, and repairing effects can be imparted to the hair due to the external use preparation or the cosmetic composition being effectively adsorbed onto the surface of the hair; and flyaway can be suppressed.

A compounded amount of the silicone gum is, for example, from 0.05 to 30 wt. % (mass %) and preferably from 1 to 15 wt. % (mass %) of the entire external use preparation or cosmetic composition. When the silicone gum is used as an emulsion composition prepared via a step of preliminarily emulsifying (including emulsion polymerization), the silicone gum can be easily blended, and can stably be blended in the hair cosmetic composition of the present invention.

An effect of imparting a specific tactile sensation or glossiness of the hair may be insufficient if the compounded amount of the silicone gum is less than the lower limit described above.

Polyamide-Modified Silicone

Examples of polyamide-modified silicones that can be preferably compounded in the external use preparation or the cosmetic composition of the present invention include siloxane-based polyamide compounds described in U.S. Pat. No. 5,981,680 (Japanese Unexamined Patent Application Publication No. 2000-038450) and Japanese Unexamined Patent Application Publication (Translation of PCT Application) No. 2001-512164. Examples of commercially available products include 2-8178 Gellant, 2-8179 Gellant and the like (manufactured by Dow Corning Corporation, in the USA). This polyamide-modified silicone also functions as an oil-based raw material, specifically as a thickening/gelling agent of a silicone oil.

When the polyamide-modified silicone is used in combination with the liquid organopolysiloxane of the present invention, the external use preparation or the cosmetic composition of the present invention delivers an excellent sense of stability and adhesion, and excellent spreading and setting when applied to the skin, the hair, or the like. Additionally, there are advantages from a quality standpoint such that a glossy feeling of sheerness and superior luster can be provided, the viscosity or hardness (softness) of the entire cosmetic composition containing the oil-based raw material can be appropriately adjusted, and an oily sensation (oily and sticky tactile sensation) can be totally controlled. Furthermore by using the liquid organopolysiloxane of the present invention, dispersion stability of perfumes, powders, and the like is improved and benefits of lasting moisturizing effects and an excellent tactile sensation can be imparted. Therefore, the obtained external use preparation or cosmetic composition will be characterized by being able to maintain a uniform and fine cosmetic sensation and usage satisfaction for an extended period of time.

Silicone Wax

Silicone waxes that can be preferably compounded in the external use preparation or the cosmetic composition of the present invention are higher alkyl-modified silicones and alkyl-modified silicone resins. The higher alkyl-modified silicone is a wax at room temperature, and is a component that is useful as a portion of the base material or a moisturizing agent of a solid cosmetic composition (e.g. an oil-based solid skin cosmetic composition product or a solid hair cosmetic composition product) or, alternatively, in hair applications, for imparting luster. Thus, the higher alkyl-modified silicone can be preferably used in the external use preparation or the cosmetic composition of the present invention. Examples of the higher alkyl-modified silicone wax include methyl (long chain alkyl) polysiloxanes having both molecular terminals capped with trimethylsiloxy groups, copolymers of a dimethylpolysiloxane having both molecular terminals capped with trimethylsiloxy groups and a methyl (long chain alkyl) siloxane, dimethylpolysiloxane modified with long chain alkyls at both terminals, and the like. Examples of commercially available products include AMS-C30 Cosmetic Wax, 2503 Cosmetic Wax, and the like (manufactured by Dow Corning Corporation, in the USA).

The liquid organopolysiloxane of the present invention has excellent affinity with the higher alkyl-modified silicone wax and has superior dispersibility properties in wax and, therefore, an external use preparation or a cosmetic composition having superior storage stability over time can be obtained. Additionally, formability of the external use preparation or the cosmetic composition, and particularly of a solid cosmetic composition will be superior. Particularly, in a system comprising a powder, effects of uniformly and stably dispersing the powder in the base material comprising the higher alkyl-modified silicone wax are obtained and hardness of the base material after forming can be appropriately mitigated. Therefore, an external use preparation or a cosmetic composition that spreads smoothly and uniformly when applied can be provided.

Furthermore, other surfactants can be stably emulsified along with a water phase in the oil phase comprising the higher alkyl-modified silicone wax of the liquid organopolysiloxane of the present invention. Therefore, due to synergy between the two phases, lasting luxuriousness and moisturizing effects and, furthermore, effects of improving cosmetic retainability exemplified by moisture resistance and sebum resistance can be imparted to the skin or the hair.

In the external use preparation or the cosmetic composition of the present invention, the higher alkyl-modified silicone wax preferably has a melting point of not lower than 60° C. because such will lead to cosmetic retainability effects and stability at high temperatures.

The alkyl-modified silicone resin is a type of film forming polymer that is compoundable in an oil phase, and is a component that imparts sebum durability, moisturizing properties, and a fine tactile sensation of the skin to the external use preparation or the cosmetic composition; and an alkyl-modified silicone resin that is in the form of a wax at room temperature can be suitably used. For example, a silsesquioxane resin wax described in Published Japanese Translation No. 2007-532754 of the PCT International Application may be mentioned. Examples of commercially available products include SW-8005 C30 RESIN WAX (manufactured by Dow Corning Corporation, in the USA), and the like.

The liquid organopolysiloxane of the present invention has excellent affinity with the higher alkyl-modified silicone wax and the alkyl-modified silicone resin wax, and has superior dispersibility properties in wax and, therefore, an external use preparation or a cosmetic composition having superior storage stability over time can be obtained. Furthermore, other surfactants can be stably emulsified along with a water phase in the oil phase comprising the alkyl-modified silicone resin wax. Therefore, a luxurious tactile sensation and moisturizing effects and, furthermore, effects of improving cosmetic retainability exemplified by moisture resistance and sebum resistance can be imparted to the skin or the hair.

Anti-Perspiration Active Component and Deodorant Agent

Additionally, in cases where the external use preparation or the cosmetic composition according to the present invention is an anti-perspirant, or depending on the purpose thereof, the external use preparation or the cosmetic composition can contain an anti-perspiration active component and/or a deodorant agent.

Examples of the anti-perspiration active component include astringent salts such as aluminum chlorohydrate, aluminum-zirconium tetrachlorohydrex glycine (ZAG), and the like; but aluminum, hafnium, zinc, and zirconium salts (e.g. aluminum halide, aluminum hydroxy halide, zirconium halide, zirconium oxyhalide, zirconium hydroxy halide, zirconyl hydroxide halide, aluminum chloride zirconium, zirconium lactate-aluminum, and basic aluminum halide) can be used. Examples thereof include $Al_2(OH)_5Cl$, aluminum bromide, buffer aluminum sulfate, alum, dried alum, various aqueous, alcohol, or glycine complexes thereof (e.g. a complex of an aluminum-zirconium chlorohydrate and glycine comprising aluminum, zirconium, and glycine (a ZAG complex), and the like. A single anti-perspiration active component may be used or a combination of two or more may be used. In cases where the anti-perspirant composition according to the present invention is a water-in-oil emulsion-type anti-perspirant composition, these anti-perspiration active components are an aqueous phase component. On the other hand, soybean extracts and isoflavones are known for their anti-perspirant effects; and, because they have low water solubility, are preferably used by dissolving them in the oil phase.

In the present invention, a compounded amount of the anti-perspiration active component is an amount sufficient to reduce perspiration, and restricting the compounded amount to a small amount can be beneficial in personal care compositions. Specifically, from the standpoints of anti-perspirant effects and tactile sensation, the compounded amount of the anti-perspiration active component in an anti-perspirant composition is preferably from 5 to 25 wt. % of the entire cosmetic composition. When using a water soluble anti-perspiration active component, from the standpoint of cost effectiveness, it is preferable to increase the proportion of water in the composition to a maximum limit, while maintaining anti-perspirant effects, but the anti-perspiration active component can also be added to the aqueous phase at amount near the saturation amount.

The external use preparation or the cosmetic composition of the present invention, particularly the anti-perspirant composition, can include a deodorant agent in conjunction with or in place of the anti-perspirant active component. Examples of the deodorant agent include deodorizers, perfumes, and substances that prevent or remove odors caused by perspiration. Such deodorant agents are antimicrobial agents (germicides or fungicides), bacteriostatic agents, odor absorbing substances, deodorizers, perfumes, or the like, and are compounded for the purpose of preventing underarm odor, odor from perspiration, foot odor, and other bodily odors. Note that these deodorant agents are useful in external use preparations or cosmetic compositions other than anti-perspirants and it goes without saying that they can be beneficially compounded in the external use preparation or the cosmetic composition of the present invention.

Examples of antimicrobial agents include alkyltrimethylammonium bromide, cetylpyridinium chloride, benzethonium chloride, benzalkonium chloride, chlorhexidine hydrochloride, chlorhexidine gluconate, [[(diisobutylphenoxy)ethoxy]ethyl]dimethylbenzylammonium chloride, N-lauroyl sarcosine sodium, N-palmitoyl sarcosine sodium, N-myristoyl glycine, N-lauroyl sarcosine potassium, trimethyl ammonium chloride, aluminum chlorohydroxy sodium lactate, triethyl citrate, tricetyl methyl ammonium chloride, 1,5-pentanediol, 1,6-hexanediol, 2,4,4'-trichloro-2'-hydroxy diphenylether (triclosan), and 3,4,4'-trichlorocarbanilide(triclocarban); L-lysine hexadecylamide and similar diaminoalkylamidos; citric acid, salicylic acid, piroctose, and other heavy metal salts, preferably zinc salts and acids thereof; pyrithione heavy metal salts, preferably pyrithione zinc, phenol zinc sulfate, ethylparaben, butylparaben, hinokitiol, farnesol, phenoxyethanol, isopropyl methylphenol, propolis, lysozyme, lysozyme chloride, combinations of lysozyme and vitamin E or derivatives thereof, combinations of organic acids such as lysozyme and α-hydroxyacid and the like; and the like.

Examples of bacteriostatic agents include 1-heptyl glyceryl ether, 1-(2-ethylhexyl)glyceryl ether, 1-octyl glyceryl ether, 1-decyl glyceryl ether, 1-dodecyl glyceryl ether, and similar glyceryl monoalkyl ethers.

The odor absorbing substance is not particularly limited, provided that it absorbs odor causing substances and reduces odor, is constituted by a portion of the inorganic powders and organic polymers described above, and displays the same characteristics.

Examples of the odor absorbing substance include zinc oxide, magnesium oxide, zeolite, aluminometasilicate, silicic anhydride, colloidal silica, talc, mica, hydroxyapatite, cellulose, corn starch, silk, nylon powder, crosslinking organopolysiloxane powder, organopolysiloxane elastomer spherical powder, and the like. Likewise, carbonates such as alkali metal carbonates, alkali metal bicarbonate salts, and the like and hydrogen carbonates, ammonium salts, tetraalkylammonium salts, and the like can be used. Of these odor absorbing substances, sodium salts and potassium salts are more preferable. Additionally, organic or inorganic porous particles carrying silver, copper, zinc, cerium, or similar metal ions (e.g. silver ion-carrying zeolite, silver ion/zinc ion/ammonium ion-carrying zeolite), or aggregates of needle-like crystals including silver cancrinite can be used. Because these function as antimicrobial agents and odor absorbing substances, they can be used beneficially as the deodorant agent.

Furthermore, hydroxyalkylated cyclodextrin, sake cake extract containing rice fermenting liquid, and various extracts derived from animals, vegetables, microorganisms, fungi, and the like such as brown seaweed extract, cinnamon bark, clove, fennel, ginger, mentha, citron, gentiana lutea, apricot, eucalyptus, Sophora flavescens, mulberry, althea, sage, Anthemis nobilis, Scutellaria root, nutgall, gardenia, hamamelis, herbs, and the like can be used as the deodorant agent. A part of these components overlaps with a bioactive component described above, but selecting these extracts as the deodorant agent for the purpose of the functional effects thereof is both beneficial and preferable from the standpoint of the composition design of the cosmetic composition.

Preferably from 0.001 to 60 wt. %, more preferably from 0.01 to 30 wt. %, and yet more preferably from 0.01 to 3 wt. % of the odor absorbing substance is included in the entire composition. Provided that the compounded amount of the odor absorbing substance is within this range, there is an advantage that deodorizing performance can be improved while not negatively affecting the strength and tactile sensation of the formulation.

Suitable perfumes include known topical use substances, topical use substances that are effective in masking malodor accompanied by perspiration, and various topical use substances that provide a composition having a desired aroma. Examples thereof include the whole of perfumes and perfume chemicals such as perfume precursors, deodorizing fragrances, and the like that are suitable for topical application to the skin and, as necessary, may be a blended perfume component.

EXAMPLES

Hereinafter, the present invention is described in detail with reference to examples. It should be understood that the present invention is not restricted to the examples. In the following compositional formulae, "M" represents an $Me_3SiO$ group (or an $Me_3Si$ group), "D" represents an $Me_2SiO$ group, "$M^H$" represents an $Me_2HSiO$ group (or an $Me_2HSi$ group), "$D^H$" represents an MeHSiO group, and "$M^R$" and "$D^R$" respectively represent units wherein the methyl group in M or D is modified by a substituent.

Note that in the following Practical Examples and Comparative Examples, "Production of Silicone compound No. X" and the like is written for convenience-sake, and the obtained products are in the form of mixtures that comprise a small amount of unreacted raw material and the like in addition to the main components.

Practical Example 1

<Production of Silicone Compound No. 1>

137.7 g of a methylhydrogenpolysiloxane expressed by the average composition formula: $MD_{42.9}D^H{}_{6.7}M$ and 14.9 g of a 3-methacryloxypropyl(tris(trimethylsiloxy)silyl ethyl dimethylsiloxy)silane expressed by the following average composition formula:

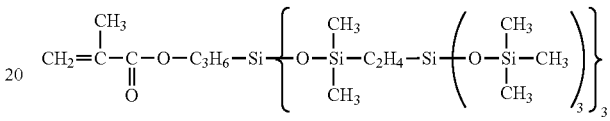

were placed in a reaction vessel, and heated to 80° C. while agitating under a nitrogen stream. 0.12 mL of an isopropyl alcohol solution of a platinum-1,3-divinyl-1,1,3,3-tetramethyldisiloxane complex (Pt concentration: 0.45 wt. %) was added and the mixture was reacted for 3 hours at 80 to 90° C. Then, a small amount of the reaction liquid was sampled and it was confirmed that the target reaction rate was reached through an alkali decomposition gas generation method (the remaining Si—H groups were decomposed using a KOH ethanol/aqueous solution, and the reaction rate was calculated from the volume of the generated hydrogen gas). Next, 38.4 g of hexadecene (α olefin purity: 91.7%) was added to the reaction mixture and the mixture was reacted for one hour at 85 to 105° C. Then, it was confirmed via the same method that the target reaction rate was reached. Thereafter, 9.3 g of diglycerin monoallyl ether and 120 g of isopropyl alcohol (IPA) were added to the reaction mixture, and 0.20 mL of the platinum catalyst described above was added. After reacting for one hour at 70 to 85° C., the mixture was sampled. As a result of calculation of the reaction rate, it was found that a modified silicone intermediate expressed by the average composition formula: $MD_{42.9}D^{R*31}{}_{0.3}D^{R*22}{}_{0.8}D^{R*11}{}_{4.4}D^H{}_{1.2}M$ had been produced. Here, $R^{*11}$, $R^{*21}$, and $R^{*31}$ are as described below.

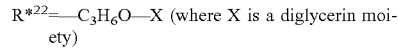

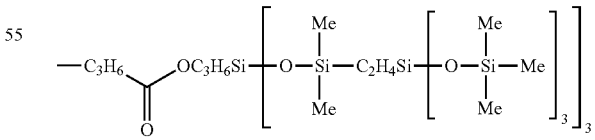

The reaction liquid was cooled to 50° C., and then 2.1 g of 1,5-hexadiene was added and the mixture was reacted for 4 hours at 50 to 75° C. In this case, the Vi/H molar ratio when crosslinking was 1.17. The mixture was sampled and the reaction rate was measured. As a result, it was found that the reaction was substantially complete. Thereafter, low-boiling components were removed by distillation under reduced pressure at 80 to 90° C. As a result, 190 g of a liquid organomodified organopolysiloxane having a glycerin derivative group and a crosslinking portion, in which the crosslinking portion links the organopolysiloxane portion and the organic portion via a Si—C bond. This product was a tan to ash-white colored transparent viscous liquid at 25° C.

An average structural formula (schematic illustration) of the liquid organopolysiloxane obtained in Practical Example 1 is shown below.

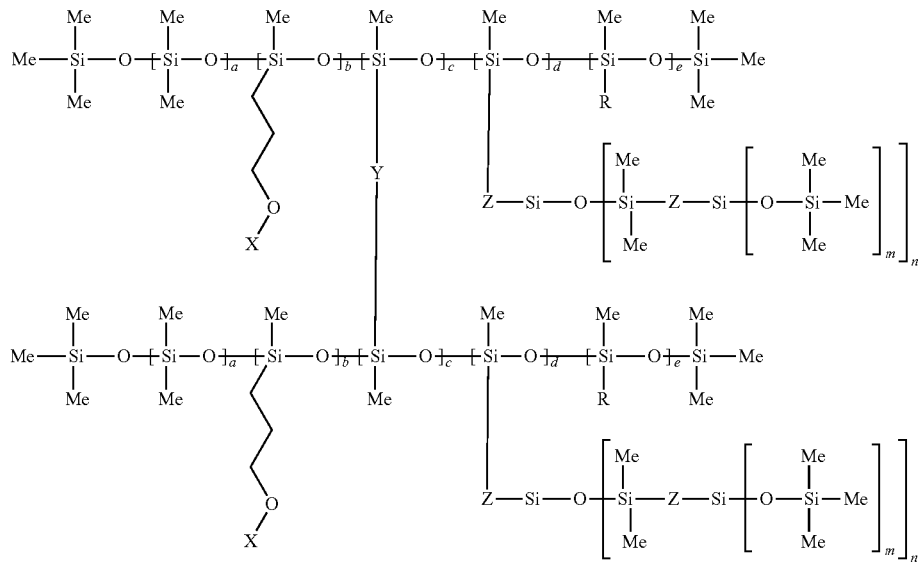

In this formula, "Me" is a methyl group, "Z" in "[ ]n" is —$CH_2CH_2$—, "Z" outside of "[ ]n" is —$C_3H_6$—COO—$C_3H_6$—, "R" is —$C_{16}H_{33}$, "Y" is —$(CH_2)_6$—, "a" is 42.9, "b" is 0.8, "c" is 1.2, "d" is 0.3, "e" is 4.4, "m" is 3, "n" is 3, and "X" is $(C_3H_6O_2)_2H$.

Comparative Example 1

<Synthesis of Comparative Silicone Compound RE-1>

155.9 g of a methylhydrogenpolysiloxane expressed by the average composition formula $MD_{72}D^H{}_{12}M$, 13.0 g of a glycerin monoallyl ether represented by the structural formula $CH_2$=CH—$CH_2$—$OCH_2CH(OH)CH_2OH$, 41.1 g of 1-decene, and 63 g of IPA were placed in a reaction vessel, and heated to 45° C. while agitating under a nitrogen stream. 0.055 g of an IPA solution of a platinum-1,3-divinyl-1,1,3,3-tetramethyldisiloxane complex (Pt concentration=4.5 wt. %) was added thereto, and the mixture was reacted for one hour at 80° C. Then, 2 g of the reaction liquid was sampled, and it was confirmed that the reaction was complete through an alkali decomposition gas generation method. The reaction liquid was heated under reduced pressure so as to distill off low-boiling components. Thus, 195 g of a tan colored semi-transparent liquid composition comprising a mono-glycerin derivative-modified silicone expressed by the average composition formula: $MD_{72}D^{R*12}{}_9D^{R*21}{}_3M$ was obtained.

In this formula, $R^{*12}$=—$C_{10}H_{21}$.

Comparative Example 2

<Synthesis of Comparative Silicone Compound RE-2>

111.6 g of a methylhydrogenpolysiloxane expressed by the average composition formula $MD_{61}D^H{}_{15}M$ was placed in a reaction vessel. Then a mixture comprising 30.9 g of a single-terminal vinyl-modified dimethylpolysiloxane represented by the structural formula $CH_2$=$CHSiMe_2(OSiMe_2)_6OSiMe_3$ and 0.10 g of a toluene solution of a platinum-1,3-divinyl-1,1,3,3-tetramethyldisiloxane complex (Pt concentration: 0.5 wt. %) was added dropwise, and the mixture was agitated at room temperature, thereby obtaining a linear siloxane branched-type polysiloxane intermediate.

Additionally, 7.0 g of triglycerin monoallyl ether, 50.4 g of 1-dodecene, 100 g of IPA, and 0.40 g of an IPA solution of a platinum-1,3-divinyl-1,1,3,3-tetramethyldisiloxane complex (Pt concentration: 0.5 wt. %) were placed in another reaction vessel, and while agitating under a nitrogen stream, the mixture was added dropwise to the previously synthesized linear siloxane branched-type polysiloxane in refluxing solvent. After the adding was completed, heating and agitating was continued for 3 hours. Then, 2 g of the reaction liquid was sampled and it was confirmed that the reaction was complete through an alkali decomposition gas generation method.

Next, the reaction liquid was moved to an autoclave and 4.0 g of a sponge nickel catalyst, 2.0 g of water, and 2.0 g of IPA was added. Then, hydrogen gas was introduced and hydrogenation treatment was carried out for 6 hours under the following conditions: 110° C., 0.9 MPa. The reaction mixture was cooled to 60° C. after the treatment and blown with hydrogen gas. Then, purging with nitrogen gas was performed three times. Next, the sponge nickel catalyst was removed via precision filtration. Thus, 204 g of a colorless, transparent filtrate was obtained.

This filtrate was placed in a separate reaction vessel and maintained for one hour at 100° C. and 20 Torr under a nitrogen stream so as to distill off low-boiling components. Thus, 138 g of a substantially colorless, semi-transparent and uniform liquid composition comprising a triglycerin derivative-modified silicone expressed by the average composition formula: $MD_{61}D^{R*13}{}_{12}D^{R*32}{}_2D^{R*23}{}_1M$ was obtained.

In this formula, $R^{*13}=-C_{12}H_{25}$

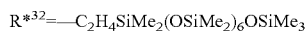

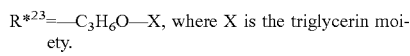

$R^{*23}=-C_3H_6O-X$, where X is the triglycerin moiety.

Practical Examples 2 to 4 and Comparative Examples 3 to 8

Using the silicone compounds obtained in Practical Example 1 and Comparative Examples 1 and 2, water-in-oil emulsion compositions having the formulations shown in Table 2 were prepared as described below. These compositions were evaluated for composition functionality (tactile sensation, sensation during use), viscosity stability, and emulsified particle size stability according to the evaluation standards below. The results are shown in Table 2. In the table, "parts" indicates "parts by weight (mass)".

Preparation Method for Water-in-Oil Emulsion Composition
1. A silicone compound comprising an oil agent and a surfactant was placed in a 200 mL container.
2. The compound was agitated and the surfactant was uniformly dispersed or dissolved in the oil agent (oil phase A).
3. Table salt and ion exchanged water were placed in a separate container. The salt was dissolved by mixing using a spatula. Furthermore, 1,3-butylene glycol was mixed and dissolved therein (aqueous phase B).
4. The saw teeth of the homo-disper were immersed in the oil phase A and, after securing the container, the aqueous phase B was poured into the oil phase A at a constant rate over a period of about 40 seconds, while agitating at 1,000 rpm.
5. The speed of the homo-disper was increased to 3,000 rpm, and the mixture was further agitated for two minutes.
6. Agitation was stopped. Then, the oily component adhered to the inner wall of the container was scraped off using a spatula and mixed with the produced emulsion.
7. The mixture was agitated for three minutes at a speed of 3,000 rpm using the homo-disper.

Functionality Evaluation (Tactile Sensation and Sensation During Use)

Sensation during use when applying, during application, and after application when using each water-in-oil emulsion composition as a cosmetic composition was evaluated according to the following standards. Note that relative comparisons were carried out within groups that used a common oil agent. Specifically:
1. 0.20 g of the water-in-oil emulsion composition was placed on a finger and spread on the back of the hand.
2. In this case, 1) spreadability and smoothness when applying to during application, 2) lack of oiliness during application to after application, 3) lack of film sensation (stickiness when dry) after application, and 4) durability of moisturizing feel were evaluated according to the following standards.

Spreadability and Smoothness: Applying to During Application
●: Smooth tactile sensation and spread easily without effort
○: Smooth tactile sensation and spread easily
Δ: Initial smoothness was experienced, but spreadability was lacking. Resistance (stickiness and adhesion when dry) with progressive spreading was experienced.
x: Heavy, poor spreadability or noticeable stickiness when initially applied.

Lack of Oiliness: During Application to after Application
●: A pleasant, water-like tactile sensation that lasted until the latter part of application. Because oiliness is controlled in order to obtain an excellent moisturizing feel, an extremely natural sensation during use with no discomfort in terms of appearance or sensation can be obtained.
○: While fading out from during application to after application, a wet (water-like) tactile sensation remained in trace amounts. Thus, a tactile sensation in which oiliness is balanced was obtained.
Δ: While a wet tactile sensation was experienced during initial application, this sensation disappears quickly and oiliness became predominant.
x: Tactile sensation was oily from initial application and the surface of the skin appeared very oily.

Lack of Film Sensation: After Application
●: Nearly no sensation of stickiness (film sensation) when dry
○: Slight sensation of stickiness (film sensation) when dry
Δ: Stickiness (film sensation) when dry experienced
x: Strong, unpleasant sensation of stickiness at latter part of application Durability of Moisturizing Feel: 10 Minutes after Application
●: Luxurious moisturizing feel lasted and there was a natural feeling with no discomfort
○: Moisturizing feel remained, but skin feels slightly drier than immediately after application. Some oiliness is visible.
Δ: No moisturizing feel and oily shine was noticeable.
x: Discomfort and irritation of the skin due to drying was felt Evaluation of Viscosity Stability 28 g of each water-in-oil emulsion composition was measured into a 35 mL glass bottle. The bottles were capped and allowed to sit at rest in a 50° C. constant temperature bath for three weeks. The viscosity stability of the emulsions before and after sitting was evaluated according to the following standards.
●: Viscosity variation=<±10% and appearance was uniform without change
○: ±10%<viscosity variation=<±20% and appearance was uniform
Δ: ±20%<viscosity variation=<±30%, or slight decrease in uniformity of the surface of the emulsion.
x: ±30%<viscosity variation, or separation of water drops, aqueous phase, oil phase, or the like. (Cases where the emulsifying itself was not possible are also indicated as "x")

Measurement of Emulsified Particle Size and Evaluation of Stability

One day after preparing the water-in-oil emulsion compositions, and after allowing the emulsion compositions (the capped 35 mL glass bottles containing 28 g of each water-in-oil emulsion composition, as described above) to sit at rest at 50° C. and −5° C. for three weeks, observation (1,000×) using an optical microscope and photographing was conducted, and the distribution range of the particle sizes was visually determined. Thereby, stability was evaluated by examining the initial emulsified particle size and the emulsified particle size over time. Note that notes were made in the Tables when particle coalescence was observed.
●: Change in emulsified particle size was small, and signs of coalescence were absent.
○: The emulsified particle size potentially increased slightly but definite coalescence was not observed. Alternatively, the emulsified particle size increased, but the overall particle size was small and the emulsion system was maintained.

Δ: It is thought that partial coalescence of the particles occurred. Definite increase in the maximum emulsified particle size.

x: Many particles were coalesced and emulsion was in the state of breaking down. (Cases where the emulsifying itself was not possible are also indicated as "x")

complex (Pt concentration: 0.45 wt. %) was added and the mixture was reacted for 2 hours at 70 to 80° C. Thereafter, 4.5 g of diglycerin monoallyl ether and 60 g of isopropyl alcohol (IPA) were added to the reaction mixture, and 0.10 mL of the platinum catalyst described above was added. After reacting for 3 hours at 70 to 80° C., the mixture was

TABLE 2

Formulations and evaluation results of the water-in-oil emulsion compositions
(Practical Examples 2 to 4 and Comparative Examples 3 to 8)

| Name of raw material | Practical Examples | | |
|---|---|---|---|
| | 2 | 3 | 4 |
| Silicone Compound No. 1 | 2 | 2 | 2 |
| Silicone compound No. RE-1 | — | — | — |
| Silicone compound No. RE-2 | — | — | — |
| Dimethylpolysiloxane (6 cSt) | 23 | 11.5 | — |
| Mineral oil 50SUS (37.8° C.) | — | 11.5 | 23 |
| Sodium chloride | 0.5 | 0.5 | 0.5 |
| Purified water | 68.5 | 68.5 | 68.5 |
| 1,3-butylene glycol | 6 | 6 | 6 |
| Spreadability and smoothness | ● | ● | ○ |
| Lack of oiliness | ● | ● | ○ |
| Lack of film sensation | ● | ● | ● |
| Moisturizing feel durability | ● | ● | ● |
| Viscosity stability of emulsion | ● | ● | ● |
| Initial particle size distribution (μm) | 2-7 | 2-7 | 2-7 |
| Coalesced | 2-10 | | |
| 50 C., 3W particle size (μm) | 2-7 | 2-7 | 2-6 |
| Coalesced | 2-15 | | |
| Coalesced | Separated | | |
| −5 C., 3W particle size (μm) | 1-5 | 2-6 | 2-6 |
| Stability of emulsified particles | ● | ● | ● |

| Name of raw material | Comparative Examples | | | | | |
|---|---|---|---|---|---|---|
| | 3 | 4 | 5 | 6 | 7 | 8 |
| Silicone Compound No. 1 | — | — | — | — | — | — |
| Silicone compound No. RE-1 | 2 | 2 | 2 | — | — | — |
| Silicone compound No. RE-2 | — | — | — | 2 | 2 | 2 |
| Dimethylpolysiloxane (6 cSt) | 23 | 11.5 | — | 23 | 11.5 | — |
| Mineral oil 50SUS (37.8° C.) | — | 11.5 | 23 | — | 11.5 | 23 |
| Sodium chloride | 0.5 | 0.5 | 0.5 | 0.5 | 0.5 | 0.5 |
| Purified water | 68.5 | 68.5 | 68.5 | 68.5 | 68.5 | 68.5 |
| 1,3-butylene glycol | 6 | 6 | 6 | 6 | 6 | 6 |
| Spreadability and smoothness | NA | NA | NA | ● | ● | ○ |
| Lack of oiliness | NA | NA | NA | ● | ○ | ○ |
| Lack of film sensation | NA | NA | NA | ● | ○ | ○ |
| Moisturizing feel durability | NA | NA | NA | ● | ● | ● |
| Viscosity stability of emulsion | X | X | X | ● | Δ | X |
| Initial particle size distribution (μm) | Separated | Separated | Separated | 2-9 | 2-13 Coalesced | 2-10 |
| 50 C., 3W particle size (μm) | Separated | Separated | Separated | 2-12 Coalesced | 2-15 Coalesced | Separated |
| −5 C., 3W particle size (μm) | Separated | Separated | Separated | 2-8 | 2-10 Coalesced | 2-9 |
| Stability of emulsified particles | X | X | X | ○ | Δ | X |

Note:
In Comparative Examples 3 to 5, the emulsion separated a short time after preparation. Therefore, tactile sensation testing was not performed. Thus, "NA" is recorded in Table 2.

Practical Example 5: Production of Silicone Compound No. 2

44.1 g of a methylhydrogenpolysiloxane expressed by the average composition formula MD42.9DH6.7M and 12.1 g of hexadecene (a olefin purity: 91.7%) were added to a reaction vessel, and heated to 75° C. while agitating under a nitrogen stream. 0.11 mL of an isopropyl alcohol solution of a platinum-1,3-divinyl-1,1,3,3-tetramethyldisiloxane complex (Pt concentration: 0.45 wt. %) was added and the mixture was reacted for 2 hours at 70 to 80° C. Thereafter, 4.5 g of diglycerin monoallyl ether and 60 g of isopropyl alcohol (IPA) were added to the reaction mixture, and 0.10 mL of the platinum catalyst described above was added. After reacting for 3 hours at 70 to 80° C., the mixture was sampled. As a result of calculation of the reaction rate, it was found that a modified silicone intermediate expressed by the average composition formula: MD42.9DR*221.75DR*114.2DH0.75M had been produced. Here, R*11 and R*21 are as described below.

R*11=—C16H33

R*22=—C3H6O—X (where X is a diglycerin moiety)

Then, 39.1 g of a methylvinyl polysiloxane expressed by the average composition formula: ViMD130.3DVi2MVi was added, and the IPA was removed by distillation. Then, 60 g of toluene and 0.23 ml of the platinum catalyst described above was added. In this case, the Vi/H molar ratio when crosslinking was 1.33. After reacting for 3 hours at 85 to 110° C., the mixture was sampled and the reaction rate was calculated. As a result, it was found that the reaction was substantially complete. Thereafter, the toluene and other low-boiling components were removed by distillation under reduced pressure at 80 to 110° C. As a result, 94.6 g of a liquid organomodified organopolysiloxane having a glycerin derivative group and a crosslinking portion, and where the crosslinking portion is linked to the organopolysiloxane portion and the organic portion via Si—C bonds, was obtained. This product was a tan to ash-white colored transparent viscous liquid at 25° C.

Practical Examples 6 to 8

Using the silicone compound obtained in Practical Example 5, a water-in-oil emulsion composition having the formulation shown in Table 3 was prepared. This composition was evaluated for composition functionality (tactile sensation, sensation during use), viscosity stability, and emulsified particle size stability. The preparation method and evaluation standards for the water-in-oil emulsion composition followed the methods used for the silicone compound of Practical Example 1, described above. The results are shown in Table 3. In the table, "parts" indicates "parts by weight (mass)".

TABLE 3 water-in-oil emulsion composition formulations and evaluation results (Practical Examples 6 to 8)

| Name of raw material | Practical Examples | | |
|---|---|---|---|
| | 6 | 7 | 8 |
| Silicone compound No. 2 | 2 | 2 | 2 |
| Dimethylpolysiloxane (6 cSt) | 23 | 11.5 | — |
| Mineral oil 50SUS (37.8° C.) | — | 11.5 | 23 |
| Sodium chloride | 0.5 | 0.5 | 0.5 |
| Purified water | 68.5 | 68.5 | 68.5 |
| 1,3-butylene glycol | 6 | 6 | 6 |
| Spreadability and smoothness | ○ | ○ | ○ |
| Lack of oiliness | ○ | ○ | ○ |
| Lack of film sensation | ● | ● | ● |
| Moisturizing feel durability | ● | ● | ● |
| Viscosity stability of emulsion | ○ | ● | ○ |
| Initial particle size distribution (μm) | 1-5 | 2-6 | 2-6 |
| 50 C., 1M particle size (μm) | 1-4 | 1-4 | 1-5 |
| −5 C., 1M particle size (μm) | 1-4 | 2-6 | 2-6 |
| Stability of emulsified particles | ● | ● | ● |

As described above, when the organomodified organopolysiloxane, having the glycerin derivative group and the crosslinking portion of the present invention and where the crosslinking portion is linked to the organopolysiloxane portion and the organic portion via Si—C bonds, is used as an emulsifier in a water-in-oil emulsifying composition, it was shown that an aqueous phase can be stably emulsified/dispersed in not only a silicone oil, but also in a nonpolar oil such as mineral oil in which it has been difficult to stably emulsify conventional glycerin-modified silicone. In other words, it was evidenced that the product of the present invention can be used much more diversely than the conventional glycerin-modified silicone used in the Comparative Examples.

Additionally, compared with conventional glycerin-modified silicone, it was shown that the emulsified particle size can be reduced to about 2 to 7 μm or smaller, stability of the emulsified particles with respect to temperature and the passing of time is excellent, and the viscosity stability of the emulsion is excellent. Moreover, with regards to tactile sensation, it was shown that the benefits of water are taken advantage of and work to suppress oiliness, and a smooth feeling when applying, a well-conforming, natural feeling to the skin, lasting moisturizing effects, a lack of stickiness, and similar superior sensations during use are provided.

In other words, it was found that if the water-in-oil emulsion composition of the present invention is used as an external use preparation or a cosmetic composition, transepithelial water loss can be effectively suppressed and, as a result, effects of moisturization, skin protection, and nutrition delivery to the skin can be expected.

Hereinafter, formulation examples of the cosmetic composition and the external use preparation according to the present invention are described, but it is understood that the cosmetic composition and the external use preparation according to the present invention are not limited to the types and compositions recited in these formulation examples. Note that, in the formulation examples, all raw materials that are described with a product number are products that are commercially available from Dow Corning Toray Co., Ltd. Additionally, in the following Formulation Examples, in compositions using a compound having an oxyalkylene structure wherein an average value of the number of repetitions of the oxyalkylene unit is two or more, a PEG-FREE formulation can be designed and put into practical use by replacing said compound with a PEG-FREE compound such as a diglycerin-modified silicone, a sugar alcohol-modified silicone, or the like. Note that the polyether-modified silicones and other similar raw materials in the Formulation Examples below can be arbitrarily replaced with a diglycerin-modified silicone having a siloxane dendron structure, a xylitol-modified silicone having a siloxane dendron structure, a diglycerin-modified silicone having a siloxane dendron structure and a long chain alkyl, a xylitol-modified silicone having a siloxane dendron structure and a long chain alkyl, or the like. Such a replacement will result in the sensation during use and moisturizing effects of the cosmetic composition or the external use preparation being enhanced and further contributions to the enhancement of cosmetic effects.

Formulation Example 1: Emulsion Foundation

| (Component) | (wt. %) |
|---|---|
| 1. Decamethyl cyclopentasiloxane | 27.0 |
| 2. Dimethylpolysiloxane (6 cSt) | 2.0 |
| 3. Methyl trimethicone (M3T) | 2.0 |
| 4. Silicone Compound No. 1 | 2.0 |
| 5. Propylene glycol | 10.0 |
| 6. Ion exchanged water | 30.0 |
| 7. Sodium L-aspartate | 2.0 |
| 8. Dextrin palmitate treated titanium dioxide | 10.0 |
| 9. Dextrin palmitate treated mica | 12.0 |
| 10. Dextrin palmitate treated talc | 2.0 |
| 11. Dextrin palmitate treated Iron oxide | 1.0 |
| 12. Paraben | q.s. |
| 13. Antioxidant | q.s. |
| 14. Perfume | q.s. |

Production Method
A: Heat and dissolve components 1 to 4 and components 12 and 13 at 50° C. Then, add and disperse components 8 to 11 by agitation.
B: Mix and dissolve components 5 to 7 and component 14 at 70° C. by agitation.
C: Return A and B to room temperature. Add B to A, which was prepared first, while agitating using a homo-mixer, and thoroughly agitate the mixture. Thereafter, degassed the mixture and charged it into a container. Thus, an emulsion foundation is obtained.

Effects

A unique sensation during use is obtained in which the emulsion foundation is extremely refreshing and spreads easily when applying; and has a superior lasting moisturizing feel without stickiness after application. Stability over time of the product is also excellent.

Formulation Example 2: Liquid Foundation

| (Component) | (wt. %) |
| --- | --- |
| 1. Decamethyl cyclopentasiloxane | 25.0 |
| 2. Dimethylpolysiloxane (2 cSt) | 18.0 |
| 3. Dimethylpolysiloxane (6 cSt) | 2.0 |
| 4. Cetyl 2-ethylhexanoate | 5.0 |
| 5. Silicone Compound No. 1 | 7.0 |
| 6. Ethanol | 8.0 |
| 7. Ion exchanged water | 2.0 |
| 8. Polymethyl silsesquioxane powder | 13.0 |
| 9. Titanium dioxide | 13.0 |
| 10. Mica | 2.0 |
| 11. Iron oxide | 1.0 |
| 12. Polyethylene powder | 1.0 |
| 13. Polystyrene powder | 1.0 |
| 14. Cellulose powder | 1.0 |
| 15. Polyamide resin powder | 1.0 |
| 16. Paraben | q.s. |
| 17. Antioxidant | q.s. |
| 18. Perfume | q.s. |

Production Method
A: Mix and dissolve components 1 to 5 and components 16 to 18 at room temperature. Then, add component 6 and completely blend while agitating with a homo-mixer.
B: Thereafter, add component 7 while blending with the homo-mixer.
C: Add components 8 to 15 to the mixture and blend/disperse using the homo-mixer. Then, degas the mixture and charge it into a container. Thus, a liquid foundation is obtained.

Effects

Stickiness is absent when applying and the foundation spreads easily; and sliding feel is extremely superior. A superior moisturizing feel and a natural sensation during use lasts after application. The product has superior stability over time and excellent cosmetic retainability.

Formulation Example 3: Foundation

| (Component) | (wt. %) |
| --- | --- |
| 1. Decamethyl cyclopentasiloxane | 24.5 |
| 2. SS-3408[*1] | 5.0 |
| 3. Light liquid isoparaffin | 15.0 |
| 4. Neopentylglycol dicaprate | 3.0 |
| 5. Silicone Compound No. 1 | 1.0 |
| 6. ES-5612 Formulation Aid[*2] | 0.5 |
| 7. Octadecyl dimethyl benzyl ammonium salt-modified montmorillonite | 4.0 |
| 8. Hydrophobization-treated titanium oxide[*3] | 10.0 |
| 9. Hydrophobization-treated talc[*3] | 6.0 |
| 10. Hydrophobization-treated mica[*3] | 6.0 |
| 11. Hydrophobization-treated red iron oxide[*3] | 1.6 |
| 12. Hydrophobization-treated yellow iron oxide[*3] | 0.7 |
| 13. Hydrophobization-treated black iron oxide[*3] | 0.2 |
| 14. Dipropylene glycol | 5.0 |
| 15. Paraoxy benzoic acid methyl ester | 0.3 |
| 16. Perfume | q.s. |
| 17. Purified water | 17.2 |

Note
[*1]caprylyl methicone
Note
[*2]Polyether-modified silicone
Note
[*3]Hydrophobization treatment: 2% methylhydrogenpolysiloxane was added to the powder and then heated.

Production Method
A: Heat and mix components 1 to 7. Then, add and uniformly disperse components 8 to 13.
B: Heat and dissolve components 14, 15, and 17.
C: While agitating, add B to A in small amounts and emulsify. Cool the emulsion and add component 16. Thus, a foundation is obtained.

Effects

The foundation is very fine and spreads easily. A moist, clean natural sensation during use without discomfort lasts in which there is no stickiness or oiliness after application. Bonding and cosmetic retainability are excellent and the foundation also has superior stability and does not vary with temperature or time.

Formulation Example 4: Pressed Powder Cosmetic

| (Component) | (wt. %) |
| --- | --- |
| 1. Silicone treated titanium oxide | 10.0 |
| 2. Silicone treated mica | 50.8 |
| 3. Silicone treated talc | 10.0 |
| 4. Silicone treated yellow iron oxide | 1.5 |
| 5. Silicone treated red iron oxide | 0.5 |
| 6. Silicone treated black iron oxide | 0.2 |
| 7. Paraffin wax | 2.0 |
| 8. Squalane | 1.4 |
| 9. 2-ethylhexyl palmitate | 2.0 |
| 10. Silicone Compound No. 1 | 15.0 |
| 11. SS-3408[*1] | 2.6 |
| 12. Methyl trimethicone (M3T) | 1.0 |
| 13. Dimethylpolysiloxane | 3.0 |
| 14. Perfume | q.s. |

Note
[*1]Caprylyl methicone

Production Method
A: Mix components 1 to 6.
B: Mix components 7 to 13 and add the mixture to A.
C: Add component 14 to B and press the mixture into a cosmetic receptacle.

Effects

The feeling to touch of the powder is dry and sensation during use is excellent. A natural feeling of application is obtained and compatibility with the skin is good. Moisture resistance, water repellency, and anti-perspirant properties are also excellent.

Formulation Example 5: Powder Foundation

| (Component) | (wt. %) |
| --- | --- |
| 1. Treated sericite*[4] | 42.0 |
| 2. Treated titanium oxide*[4] | 12.0 |
| 3. Treated talc*[4] | 24.0 |
| 4. Treated yellow iron oxide*[4] | 2.4 |
| 5. Treated red iron oxide*[4] | 0.8 |
| 6. Treated black iron oxide*[4] | 0.3 |
| 7. Dimethylpolysiloxane | 1.8 |
| 8. Methyl trimethicone (M3T) | 0.5 |
| 9. Liquid paraffin | 6.2 |
| 10. Octyldodecanol | 2.0 |
| 11. 9702 Powder*[5] | 8.0 |
| 12. Perfume | q.s. |
| 13. Preservative | q.s. |

Note
*[4] A modified powder obtained by: Mixing (in advance) sericite, titanium oxide, talc, yellow iron oxide, red iron oxide, and black iron oxide, all treated with 3% methylhydrogenpolysiloxane at the compounding ratio shown in Formulation Example 5; dispersing the unmodified powder obtained as described above in chloroform, adding the silicone compound No. 1 at an amount of 8% with respect to the powder, and agitating; and removing the chloroform under reduced pressure by distillation and crushing the product.

Note
*[5] Organopolysiloxane elastomer spherical powder (composite powder with mica)

Production Method
A: Mix components 1 to 6 using a Henschel mixer.
B: Mix components 7 to 13 and add the mixture to A. Then, further agitate the mixture.
C: Crush B using an atomizer. Then, pour the product into a mold. Thus, a foundation is obtained.

Effects
With the foundation, while feeling to touch of, the powder is extremely light and dry, a smooth and substantial sense of application can be obtained. The sense of coarseness particular to powders is reduced. Additionally, because the foundation has superior moisture resistance, water repellency, and anti-perspirant properties, cosmetic retainability is good.

Formulation Example 6: Pressed Foundation

| (Component) | (wt. %) |
| --- | --- |
| 1. Perfluoropolyether treated titanium oxide | 9.0 |
| 2. Perfluoropolyether treated zinc oxide | 3.0 |
| 3. Perfluoropolyether treated red iron oxide | 0.4 |
| 4. Perfluoropolyether treated yellow iron oxide | 4.0 |
| 5. Perfluoropolyether treated black iron oxide | 0.2 |
| 6. Perfluoropolyether treated talc | 15.0 |
| 7. Perfluoropolyether treated mica | 48.2 |
| 8. Perfluoropolyether treated titanated mica | 2.0 |
| 9. 9701 Cosmetic Powder*[6] | 2.0 |
| 10. Squalane | 4.0 |
| 11. Dimethylpolysiloxane | 6.0 |
| 12. Vaseline | 2.0 |
| 13. Glyceryl triisooctanoate | 2.0 |
| 14. Perfluoropolyether-modified silicone | 1.0 |
| 15. Silicone Compound No. 1 | 1.0 |
| 16. Preservative | 0.1 |
| 17. Perfume | 0.1 |

Note
*[6] Organopolysiloxane elastomer spherical powder (silica-covered type)

Production Method
A: Disperse/mix components 1 to 9.
B: Heat and uniformly mix components 10 to 17.
C: Add B to A and mix and, thereafter, crush the mixture. Compress the product into a cosmetic receptacle. Thus, a pressed foundation is obtained.

Effects
The foundation is durable against impact and does not crack easily. Bonding to the skin is excellent, and moisture resistance, water repellency, anti-perspirant properties, and also sebum resistance are superior. Therefore, cosmetic retainability is extremely good.

Formulation Example 7: Foundation

| (Component) | (wt. %) |
| --- | --- |
| 1. Hydrogenated soy phospholipid | 0.5 |
| 2. Phytosterol | 0.1 |
| 3. Squalane | 1.0 |
| 4. Glycerin | 2.0 |
| 5. 1,3-butylene glycol | 2.0 |
| 6. Purified water | remainder |
| 7. Sodium chloride | 1.0 |
| 8. Paraoxy benzoic acid methyl | 0.3 |
| 9. Ethanol | 3.0 |
| 10. Silicone Compound No. 1 | 2.0 |
| 11. Alkyl·polyether co-modified silicone having a siloxane dendron structure | 1.0 |
| 12. Diglyceryl diisostearate | 1.0 |
| 13. 2-ethylhexyl paramethoxycinnamate | 3.0 |
| 14. Glyceryl tri(2-ethylhexanoate) | 5.0 |
| 15. Pentaerythritol rosinate | 0.1 |
| 16. Dextrin palmitate | 0.5 |
| 17. Inulin stearate | 0.5 |
| 18. Dimethyldistearyl ammonium hectorite | 1.0 |
| 19. Silicone treated titanium oxide | 10.0 |
| 20. Silicone treated red iron oxide | 0.3 |
| 21. Silicone treated yellow iron oxide | 1.5 |
| 22. Silicone treated black iron oxide | 0.05 |
| 23. Silicone treated fine participate titanium oxide | 2.0 |
| 24. Nylon powder | 2.0 |
| 25. Decamethyl cyclopentasiloxane | 18.0 |

Production Method
A: Heat components 1 to 5 to 75° C.
B: Heat component 6 to 75° C.
C: Add B to A and mix. Then, cool the mixture to room temperature.
D: Add and mix components 7 to 9 with C.
E: Mix components 10 to 25 using a roll mill.
F: Add/mix E with D while agitating. Thus, a foundation is obtained.

Effects
Based on the properties inherent in soy phospholipids, it is anticipated that a liposome having a lipid bilayer structure will be formed in the emulsion foundation. Adhesion to the skin is excellent and cosmetic retainability is superior. The foundation is free of stickiness during use and a natural feeling on the skin and superior moisturizing feel last. Stability over time of the product is also excellent.

Formulation Example 8: Foundation

| (Component) | (wt. %) |
| --- | --- |
| 1. Dimethylpolysiloxane (2 cSt) | 10.0 |
| 2. Isohexadecane | 21.6 |
| 3. Isostearyl diglyceryl succinate | 0.6 |
| 4. ES-5612 Formulation Aid*[2] | 1.2 |
| 5. Silicone Compound No. 1 | 0.6 |
| 6. BY 25-320*[7] | 1.5 |
| 7. FZ-2250*[8] | 1.5 |
| 8. FA 4002 ID*[9] | 2.0 |
| 9. DC 593*[10] | 2.0 |

-continued

| (Component) | (wt. %) |
|---|---|
| 10. Coated Iron oxide | 3.5 |
| 11. Coated titanium dioxide | 6.8 |
| 12. Nylon 12 | 8.0 |
| 13. Ion exchanged water | 40.0 |
| 14. Magnesium sulfate | 0.7 |
| 15. Preservative | q.s. |

Note
*[2] Polyether-modified silicone

Note
*[7] Isoparaffin solution (20 wt. %) of dimethylpolysiloxane gum

Note
*[8] Isoparaffin solution (35 wt. %) of polyether-silicone block copolymer

Note
*[9] Isododecane solution of (acrylates/polytrimethylsiloxy methacrylate) copolymer (active component: 40 wt. %)

Note
*[10] Dimethylpolysiloxane (100 cSt) solution of trimethylsiloxysilicate (active component: 33%)

Production Method

A: Mix components 1 to 9 and then uniformly disperse components 10 to 12 therein.

B: Mix components 13 to 15 and, thereafter, add A and emulsify the mixture. Thus, a foundation is obtained.

Effects

With the foundation, a cosmetic film that imparts a feeling of smoothness and substance can be obtained regardless of whether the foundation spreads smoothly and easily. A sensation of dryness, tightness or stretching, or the like is, for the most part, not felt after application, adhesion to the skin is excellent, and cosmetic retainability is superior.

Formulation Example 9: Solid Foundation

| (Component) | (wt. %) |
|---|---|
| [Pigment Portion] (38.2 wt. %) | |
| 1. Treated spherical titanium oxide (average primary particle size: 0.4 μm)*[11] | 18.0 |
| 2. Treated iron oxide (mixture of black iron oxide, red iron oxide, and yellow iron oxide)*[11] | 1.7 |
| 3. Treated talc*[11] | 6.0 |
| 4. Treated mica*[11] | 2.0 |
| 5. Nε-lauroyl-L-lysine | 3.5 |
| 6. Polyalkyl•methylsilsesquioxane (average primary particle size: 4 μm) | 5.0 |
| 7. Octylsilylated fine particulate titanium oxide (average primary particle size: 10 nm) | 2.0 |
| [Liquid Portion] | |
| 8. Decamethyl cyclopentasiloxane | 15.0 |
| 9. Methyltrimethiconepolyol (6.5 wt. %) | 10.0 |
| 10. 1,3-butyleneglycol | 5.0 |
| 11. Maltitol | 1.0 |
| 12. Raffinose | 0.5 |
| Surfactant (2 wt. %) | |
| 13. Silicone Compound No. 1 | 1.0 |
| 14. Sorbitan isostearate | 1.0 |
| Solid or paste-like oil agent (5 wt. %) | |
| 15. Paraffin | 5.0 |
| Purified water (12.7 wt. %) | |
| 16. Purified water | 12.7 |
| Oil agent (9.5 wt. %) | |
| 17. Dimethylpolysiloxane (6 cSt) | 3.0 |
| 18. Methylphenylpolysiloxane | 2.0 |
| 19. Octyl paramethoxycinnamate | 2.0 |

-continued

| (Component) | (wt. %) |
|---|---|
| 20. Propylene glycol dicaprate | 2.0 |
| 21. Dipentaerythrityl hexahydroxystearate | 0.5 |
| Bioactive component | |
| 22. Cranberry extract | 1.0 |
| (average primary particle size: 10 nm) Preservative | |
| 23. Paraben | 0.1 |

Note
*[11] Nε-lauroyl-L-lysine 5 wt. % treated pigment

Production Method

A: Uniformly mix the oil-based liquid portion (components 8 to 9, components 13 to 15, components 17 to 21, and component 23) and dissolve the components at 80° C.

B: Add the pre-mixed and crushed pigment portion (components 1 to 7) thereto and uniformly disperse at 80° C.

C: Then, add, emulsify, and disperse the water-based liquid portion (components 10 to 12, component 16, and component 22) that was uniformly pre-mixed and dissolved at 80° C. in the mixture.

D: Degas the obtained emulsion, press it into a cosmetic receptacle, and set it in a hermetic container. Thus, a solid foundation is obtained.

Effects

When applying, the solid foundation does not impart a feeling of dryness to the skin, and has superior compatibility with the skin. The solid foundation has reduced oiliness, and feels good when applied. Moreover cosmetic retainability is good. The stability of the product is good and hardly suffers from separation or agglomeration.

Formulation Example 10: Oil-Based Foundation

| (Component) | (wt. %) |
|---|---|
| 1. Liquid paraffin | 10.0 |
| 2. Squalane | 7.0 |
| 3. Branched fatty acid cholesteryl ester | 7.0 |
| 4. Paraffin wax | 5.0 |
| 5. Starch fatty acid ester | 5.0 |
| 6. Silicone Compound No. 1 | 10.0 |
| 7. Titanium oxide (hydrophobization-treated) | 20.0 |
| 8. Titanated mica (hydrophobization-treated) | 3.0 |
| 9. Mica (hydrophobization-treated) | 30.0 |
| 10. Inorganic coloration pigment (hydrophobization-treated) | 3.0 |

Production Method

A: Heat components 1 to 6 to 90° C. and dissolve.

B: Add components 7 to 10 to the mixture, uniformly mix, and degas.

C: Mold the mixture by pouring it into a mold and cooling.

Effects

The oil-based foundation spreads smoothly, and covers the skin closely. Thus, a beautiful finish is obtained. The oil-based foundation has a good sense of adhesion while producing a natural feeling on the skin with no discomfort.

Formulation Example 11: Water-in-Oil Cream

| (Component) | (wt. %) |
|---|---|
| 1. Dimethyldistearyl ammonium hectorite | 1.0 |
| 2. Dioctadecyl methyl ammonium salt-modified montmorillonite | 1.0 |
| 3. Dimethylpolysiloxane (6 cSt) | 5.0 |
| 4. 2-ethylhexyl paramethoxycinnamate | 2.0 |
| 5. Diethylpentanediol dineopentanoate | 3.0 |
| 6. DC 9011 Silicone Elastomer Blend*[12] | 6.0 |
| 7. Silicone Compound No. 1 | 1.0 |
| 8. Dipropylene glycol | 10.0 |
| 9. Sodium citrate | 0.2 |
| 10. Ethanol | 3.0 |
| 11. Preservative | q.s. |
| 12. Perfume | q.s. |
| 13. Purified water | 67.8 |

Note
*[12] Product in which crosslinking polyether-modified silicone is diluted using decamethyl cyclopentasiloxane (elastomer component: 15%)

Production Method
A: Mix components 1 to 7.
B: Mix and dissolve components 8 to 13, and add A thereto. Then, agitate and emulsify the mixture. Thus, a water-in-oil cream is obtained.

Effects

Oiliness and stickiness is absent, spreading is easy, and a refreshing, clean sensation during use can be obtained. Compatibility with the skin is good and a rich moisturizing feel lasts. Also, a natural matted finish can be obtained. Stability over time of the product is also excellent.

Formulation Example 12: Water-in-Oil Emulsion Composition

| (Component) | (wt. %) |
|---|---|
| 1. Decamethyl cyclopentasiloxane | 6.2 |
| 2. Dimethylpolysiloxane (6 cSt) | 3.0 |
| 3. Dimethylpolysiloxane (2 cSt) | 2.0 |
| 4. Methyl trimethicone (M3T) | 2.0 |
| 5. SH 556*[13] | 3.0 |
| 6. Methylpentanediol dineopentanoate | 3.0 |
| 7. 9040 Silicone Elastomer Blend*[14] | 5.0 |
| 8. Squalane | 5.8 |
| 9. Paraffin wax | 0.3 |
| 10. Palmitate | 0.2 |
| 11. Silicone Compound No. 1 | 2.0 |
| 12. Pseudo-sphingosine | 0.2 |
| 13. Pseudo-ceramide | 5.0 |
| 14. Magnesium stearate | 1.0 |
| 15. Magnesium sulfate | 1.0 |
| 16. Paraoxy benzoic acid methyl | 0.2 |
| 17. Glycerin | 16.0 |
| 18. Dipropylene glycol | 0.5 |
| 19. Purified water | 43.6 |

Note
*[13] Phenyl trimethicone
Note
*[14] Product in which crosslinking organopolysiloxane (dimethicone crosspolymer) is diluted using decamethyl cyclopentasiloxane (elastomer component: 12%)

Production Method
A: Heat components 1 to 13 and component 16 to 80 to 90° C. and agitate so as to dissolve the components.
B: Add component 14 to A and agitate/blend so as to be uniformly dispersed.
C: Separately, mix component 15 and components 17 to 19 so as to form a solution.
D: Add C in small amounts while holding the temperature of B at 80° C. and mixing uniformly. Then, while agitating, cool the mixture to room temperature. Thus, a water-in-oil emulsion composition is obtained.

Effects

The water-in-oil emulsion composition is suitable for skin care, particularly face care. A clean sensation when applying and a natural feeling on the skin, free of discomfort, can be obtained. The finish is somewhat matted and small wrinkles in the skin can be concealed.

Formulation Example 13: Water-in-Oil Emulsion Rouge (Liquid)

| (Component) | (wt. %) |
|---|---|
| 1. FA 4001 CM*[15] | 20.0 |
| 2. BY 11-018*[16] | 25.0 |
| 3. Aerosol-form silicic anhydride | 0.1 |
| 4. Spherical urethane powder | 5.0 |
| 5. Silicone Compound No. 1 | 5.0 |
| 6. Octylmethoxycinnamate | 1.0 |
| 7. Red No. 202 | 0.5 |
| 8. Titanium oxide | 0.5 |
| 9. Titanated mica | 3.0 |
| 10. Perfume | 0.1 |
| 11. Ethanol | 10.0 |
| 12. Preservative | 0.2 |
| 13. Sodium chloride | 0.1 |
| 14. Purified water | 29.5 |

Note
*[15] Decamethyl cyclopentasiloxane solution of (acrylates/polytrimethylsiloxy methacrylate) copolymer (active component: 30%)
Note
*[16] Decamethyl cyclopentasiloxane solution of trimethylsiloxysilicate (active component: 30%)

Production Method
A: Mix and disperse components 1 to 10.
B: Separately, uniformly disperse components 11 to 14.
C: Add B to A and emulsify. Then, degas the emulsion and charge it into a container. Thus, a water-in-oil emulsified rouge is obtained.

Effects

The rouge spreads easily and a sensation during use that is free of stickiness can be obtained. A sensation of tightness or stretching is not easily produced during use and moisturizing effects are enduring. The rouge has superior moisture resistance and water repellency and, therefore is mostly free of color staining; and the product has excellent stability over time.

Formulation Example 14: Emulsion

| (Component) | (wt. %) |
|---|---|
| 1. Decamethyl cyclopentasiloxane | 15.0 |
| 2. Methylphenylpolysiloxane | 5.0 |
| 3. Squalene | 5.0 |
| 4. Pentaerythritol tetra-2-ethylhexanoate | 5.0 |
| 5. Silicone Compound No. 1 | 1.0 |
| 6. BY 22-008M*[17] | 2.0 |
| 7. 9701 Cosmetic Powder*[6] | 2.0 |
| 8. Hydrophobized silica | 0.5 |
| 9. Magnesium ascorbyl phosphate | 1.0 |
| 10. Sodium chloride | 1.0 |
| 11. Polyethylene glycol 11000 | 1.0 |
| 12. Propylene glycol | 8.0 |

-continued

| (Component) | (wt. %) |
|---|---|
| 13. Preservative | q.s. |
| 14. Perfume | q.s. |
| 15. Purified water | remainder |

Note
*[17]Decamethyl cyclopentasiloxane solution of polyether-modified silicone (active component: 12%)

Note
*[6]organopolysiloxane elastomer spherical powder (silica-covered type)

Production Method
A: Uniformly mix components 1 to 6. Then, add and uniformly disperse components 7 and 8.
B: Add and dissolve components 9 to 11 to component 15. Furthermore, uniformly mix components 12 and 13 and then add this mixture thereto.
C: Add B in small portions to A and emulsify. Then, cool the emulsion and add component 14. Thus, an emulsion is obtained.

Effects

An emulsion having a soft, puffy texture is obtained that spreads easily and is free of stickiness. A discomfort-free natural feeling on the skin and superior moisturizing feel last after application. Change over time or due to temperature is minimal and stability is excellent.

Formulation Example 15: Cream

| (Component) | (wt. %) |
|---|---|
| 1. Hydrogenated soy phospholipid | 1.0 |
| 2. Cholesterol | 0.5 |
| 3. Dipropylene glycol | 10.0 |
| 4. Glycerin | 10.0 |
| 5. Purified water | 56.5 |
| 6. Sodium lactate | 1.0 |
| 7. Silicone Compound No. 1 | 1.5 |
| 8. Decamethyl cyclopentasiloxane | 10.0 |
| 9. Methyl trimethicone (M3T) | 1.5 |
| 10. Glyceryl tri(2-ethylhexanoate) | 5.0 |
| 11. Meadowfoam oil | 3.0 |

Production Method
A: Heat components 1 to 4 to 75° C.
A: Heat components 5 and 6 to 75° C.
C: Add B to A and mix. Then, cool the mixture to room temperature.
D: While agitating, add C in small amounts to components 7 to 11 and mix. Thus, a cream is obtained.

Effects

Based on the properties inherent in soy phospholipids, it is anticipated that a liposome having a lipid bilayer structure will be formed in the cream. Compatibility with the skin is good and the cream is free of stickiness. Feel after using is a superior luxurious and moisturizing, and stability over time is also excellent.

Formulation Example 16: Aftershave Cream

| (Component) | (wt. %) |
|---|---|
| 1. SS-3408*[1] | 35.0 |
| 2. SS-2910*[2] | 2.9 |
| 3. Silicone Compound No. 1 | 5.0 |
| 4. Polyethyleneglycol (molecular weight: 400) | 5.0 |
| 5. Sodium L-glutamate | 2.0 |
| 6. Allantoin | 0.1 |
| 7. Aloe extract | 0.1 |
| 8. Preservative | 0.1 |
| 9. Antioxidant | 0.1 |
| 10. Perfume | 0.7 |
| 11. Purified water | 49.0 |

Note
*[1]Caprylyl methicone

Note
*[2]Polyether-modified silicone

Production Method
A: Heat and mix components 1 to 4 and component 10.
B: Heat and mix components 5 to 9 and component 11.
C: Add B in small amounts to A and emulsify. Thus, an aftershave cream is obtained.

Effects

The aftershave cream has an appropriate viscosity and, therefore does not run when used, and also spreads easily and is free of stickiness. With the aftershave cream, irritation of the skin is minimal and, after application, a lasting moisturizing, but clean feel can be imparted. Additionally, the stability of the product is extremely good.

Formulation Example 17: Daytime Use Skin-Lightening Cream

| (Component) | (wt. %) |
|---|---|
| 1. SS-2910*[2] | 1.0 |
| 2. Silicone Compound No. 1 | 2.0 |
| 3. SH 556*[13] | 5.0 |
| 4. SS-3408*[1] | 6.0 |
| 5. Dimethylpolysiloxane (2 cSt) | 6.0 |
| 6. Glycerin | 5.0 |
| 7. Dipropylene glycol | 10.0 |
| 8. Paraoxy benzoic acid methyl | 0.2 |
| 9. Ascorbic acid sulfate sodium | 0.1 |
| 10. Ascorbic acid phosphate sodium | 0.1 |
| 11. γ-aminobutyric acid | 0.1 |
| 12. Appleseed extract (anti-oxidizing agent) | 0.1 |
| 13. Sodium chloride | 0.9 |
| 14. Perfume | 0.1 |
| 15. Purified water | 63.4 |

Note
*[2]Polyether-modified silicone

Note
*[13]Phenyl trimethicone

Note
*[1]Caprylyl methicone

Production Method
A: Heat components 1 to 5 to 60° C. and dissolve.
B: Heat components 6 to 15 to 60° C. and dissolve.
C: Add A to B while agitating in order to emulsify/mix.
D: Then, while agitating, cool the mixture to 30° C., and charge the mixture into a container. Thus, a daytime use skin-lightening cream is obtained.

Effects

The daytime use skin-lightening cream is free of discomfort such as a feeling of dryness when applying, spreads easily, and provides a superior moisturizing sensation during use. The moisturizing effect thereof is lasting and the skin does not become dry and coarse. The daytime use skin-lightening cream is easy to use as a cosmetic base.

Formulation Example 18: W/O Emulsion-Type Skin External Use Preparation

| (Component) | (wt. %) |
| --- | --- |
| 1. Dimethylpolysiloxane (20 cSt) | 10.0 |
| 2. Dimethylpolysiloxane (2 cSt) | 20.0 |
| 3. Silicone Compound No. 1 | 2.0 |
| 4. Ethanol | 20.0 |
| 5. Diisopropylamine dichloroacetate | 0.2 |
| 6. Purified water | 47.8 |

Production Method

A: Dissolve components 1 to 3 by agitating and heating to 70° C.

B: Separately, mix components 4 to 6 so as to form a solution. Heat the solution to 70° C.

C: Add B in small amounts and emulsify while holding the temperature of A at 70° C. and mixing uniformly. Then, while agitating, cool the mixture to 30° C. Thus, a W/O emulsion skin external use preparation is obtained.

Effects

As a result of compounding the silicone compound No. 1, the transdermal absorption rate of the diisopropylamine dichloroacetate (bioactive substance) is accelerated. Additionally, the pharmacological effects of the bioactive component itself are enhanced due to being transdermally absorbed.

Formulation Example 19: Polyol/O-Type Nonaqueous Emulsion Skin External Use Preparation

| (Component) | (wt. %) |
| --- | --- |
| 1. Dimethylpolysiloxane (20 cSt) | 3.0 |
| 2. Dimethylpolysiloxane (2 cSt) | 15.0 |
| 3. Liquid paraffin | 10.0 |
| 4. Cetyl 2-ethylhexanoate | 5.0 |
| 5. Silicone Compound No. 1 | 5.0 |
| 6. Vitamin E | 0.1 |
| 7. Magnesium ascorbyl phosphate | 0.2 |
| 8. Sodium chloride | 1.0 |
| 9. Glycerin | 25.0 |
| 10. 1,3-butylene glycol | 10.7 |
| 11. Dipropylene glycol | 25.0 |

Production Method

A: Dissolve components 1 to 6 by agitating and heating at 50° C.

B: Separately, dissolve components 7 to 11 by agitating and mixing at 50° C.

C: Add B in small amounts and emulsify while holding the temperature of A at 50° C. and mixing uniformly.

D: Then, while agitating, cool the mixture to 30° C. Thus, a polyol/O-type nonaqueous emulsion skin external use preparation is obtained.

Effects

Because a stable emulsion of the nonaqueous system can be obtained, stability of the ascorbic acid derivative can be advantageously maintained and, as a result, it is expected that the benefits inherent in vitamin C (a bioactive substance) will be displayed mildly and for an extended period of time on or within the skin.

Formulation Example 20: Polyol/O-Type Nonaqueous Emulsion Skin External Use Preparation

| (Component) | (wt. %) |
| --- | --- |
| 1. Dimethylpolysiloxane (20 cSt) | 3.0 |
| 2. Dimethylpolysiloxane (2 cSt) | 15.0 |
| 3. Liquid paraffin | 10.0 |
| 4. Cetyl 2-ethylhexanoate | 4.0 |
| 5. Silicone Compound No. 1 | 6.0 |
| 6. Trisodium ascorbyl palmitate phosphate | 0.2 |
| 7. Vitamin E | 0.1 |
| 8. Sodium chloride | 1.0 |
| 9. Glycerin | 25.0 |
| 10. 1,3-butylene glycol | 10.7 |
| 11. Dipropylene glycol | 25.0 |

Production Method

A: Dissolve components 1 to 7 by agitating and heating at 50° C.

B: Separately, dissolve components 8 to 11 by agitating and mixing at 50° C.

C: Add B in small amounts to A and emulsify while holding the temperature at 50° C. and mixing uniformly.

D: Then, while agitating, cool the mixture to 30° C. Thus, a polyol/0-type nonaqueous emulsion skin external use preparation is obtained.

Effects

Because a stable emulsion of the nonaqueous system can be obtained, stability of the trisodium ascorbyl palmitate phosphate can be advantageously maintained and, as a result, it is expected that the preparation will be effectively transdermally absorbed due to properties inherent to said substance, and that the benefits inherent in vitamin C (a bioactive substance) will be displayed mildly and for an extended period of time within the skin.

Formulation Example 21: O/W Cream

| (Component) | (wt. %) |
| --- | --- |
| 1. 2503 Cosmetic Wax*[18] | 5.0 |
| 2. Cetanol | 1.0 |
| 3. Liquid paraffin | 10.0 |
| 4. Dimethylpolysiloxane (20 cSt) | 5.0 |
| 5. Decamethyl cyclopentasiloxane | 5.0 |
| 6. Vaseline | 2.0 |
| 7. Candelilla wax | 2.0 |
| 8. Glyceryl triisostearate | 5.0 |
| 9. Stearic acid | 3.0 |
| 10. Glyceryl monostearate | 1.5 |
| 11. Silicone Compound No. 1 | 5.0 |
| 12. Sorbitan sesquioleate | 0.5 |
| 13. Polyoxyethylene sorbitan monooleate | 1.0 |
| 14. Sodium hydroxide (1% aqueous solution) | 10.0 |
| 15. 1,3-butylene glycol | 5.0 |
| 16. Glycerin | 5.0 |
| 17. Preservative | q.s. |
| 18. Perfume | q.s. |

-continued

| (Component) | (wt. %) |
|---|---|
| 19. BY 29-129*[19] | 5.0 |
| 20. Purified water | 51.0 |

Note
*[18]Stearyl dimethicone

Note
*[19]Aqueous dispersion of organopolysiloxane elastomer spherical powder (active component: 63%)

Production Method

A: Mix, heat, and dissolve components 1 to 13.

B: Mix, heat, and dissolve components 14 to 17 and 20.

C: Add B to A and emulsify, and then cool the emulsion to 40° C. Then, add components 18 and 19 and uniformly mix.

D: Then, cool the mixture to room temperature. Thus, an O/W hand cream is obtained.

Effects

The O/W cream spreads easily, has superior adhesion to the skin, feels rich on the skin without being sticky, and has a dry feeling to touch. Moreover, with the O/W cream, the skin surface is free of oily glossiness and has a matted, natural finish. The O/W cream also provides a benefit of concealing small lines and wrinkles. The product itself has excellent stability over time.

Formulation Example 22: Sunscreen Emulsion

| (Component) | (wt. %) |
|---|---|
| 1. Decamethyl cyclopentasiloxane | 20.0 |
| 2. Caprylyl methicone | 3.0 |
| 3. Sorbitan monoisostearate | 1.0 |
| 4. SS-2910*[2] | 0.3 |
| 5. Silicone Compound No. 1 | 0.3 |
| 6. Dioctadecyl methyl ammonium salt-modified montmorillonite | 0.2 |
| 7. BY 11-018*[16] | 1.0 |
| 8. Octyl paramethoxycinnamate | 4.0 |
| 9. Fatty acid soap treated fine particulate titanium dioxide | 8.0 |
| 10. Sorbitol | 2.0 |
| 11. Sodium chloride | 1.0 |
| 12. Preservative | q.s. |
| 13. Perfume | q.s. |
| 14. Purified water | 59.2 |

Note
*[2]Polyether-modified silicone

Note
*[16]Decamethyl cyclopentasiloxane solution of trimethylsiloxysilicate

Production Method

A: Heat and mix components 1 to 8. Then, uniformly disperse component 9.

B: Separately, heat and mix components 10 to 12 and 14.

C: While agitating, add B to A in small amounts and emulsify. Cool the emulsion and then add component 13. Thus, a sunscreen emulsion is obtained.

Effects

Stickiness and coarseness particular to suncare products are, for the most part, not felt when applying, and the emulsion is fine and is easily spread. A rich moisturizing feel lasts and cosmetic retainability is good. Therefore, ultraviolet light blocking effects last. The stability over time of the product is excellent and the powder does not easily agglomerate.

Formulation Example 23: UV Blocking Cream

| (Component) | (wt. %) |
|---|---|
| 1. Decamethyl cyclopentasiloxane | 17.5 |
| 2. FA 4002 ID*[9] | 12.0 |
| 3. Glyceryl triisooctanoate | 5.0 |
| 4. Octyl paramethoxycinnamate | 6.0 |
| 5. Alkyl•polyether co-modified silicone having a siloxane dendron structure | 1.0 |
| 6. Silicone Compound No. 1 | 0.5 |
| 7. Organo-modified bentonite | 0.2 |
| 8. Silicone treated zinc oxide | 20.0 |
| 9. 9702 Powder*[5] | 3.0 |
| 10. Sodium chloride | 0.5 |
| 11. 1,3-butylene glycol | 2.0 |
| 12. Preservative | q.s. |
| 13. Perfume | q.s. |
| 14. Purified water | 32.3 |

Note
*[9]Isododecane solution of (acrylates/polytrimethylsiloxy methacrylate) copolymer (active component: 40%)

Note
*[5]organopolysiloxane elastomer spherical powder (composite powder with mica)

Production Method

A: Add component 2 to a portion of component 1 so as to form a uniform mixture. Then, add component 8 and disperse using a bead mill.

B: Uniformly mix and blend the remainder of component 1 and components 3 to 7.

C: Mix and dissolve components 9 to 11 and 13.

D: Add C to B and emulsify. Then, add A and component 12. Thus, a UV blocking cream is obtained.

Effects

The UV blocking cream is substantially free of stickiness, and spreads very easily. Additionally, while having superior adhesive sensation, a discomfort free natural feeling on the skin is obtained. The finish thereof is glossy and cosmetic retainability is extremely good. The UV blocking cream is also stable with respect to temperature and the passage of time.

Formulation Example 24: UV Blocking Water-in-Oil Emulsion

| (Component) | (wt. %) |
|---|---|
| 1. Dimethylpolysiloxane (6 cSt) | 9.0 |
| 2. Silicone Compound No. 1 | 1.0 |
| 3. Glyceryl trioctanoate | 2.0 |
| 4. Dimethyldistearyl ammonium hectorite | 0.5 |
| 5. Octadecyl dimethyl benzyl ammonium salt-modified montmorillonite | 0.5 |
| 6. SS-2910*[2] | 1.0 |
| 7. Dispersant of fine particulate titanium oxide in D5*[20] | 30.0 |
| 8. Dispersant of fine particulate zinc oxide in D5*[21] | 30.0 |
| 9. Dipropylene glycol | 3.0 |
| 10. Sodium citrate | 0.2 |
| 11. Preservative | q.s. |

-continued

| (Component) | (wt. %) |
|---|---|
| 12. Perfume | q.s. |
| 13. Purified water | 22.8 |

Note
[*2]Polyether-modified silicone

Note
[*20]Comprises decamethyl cyclopentasiloxane, fine particulate titanium oxide and a dispersing agent (alkyl•polyglycerin co-modified silicone having a siloxane dendron structure); Formulation weight ratio is 50:40:8 (decamethyl cyclopentasiloxane:titanium oxide:dispersing agent).

Note
[*21]Comprises decamethyl cyclopentasiloxane, fine particulate zinc oxide and a dispersing agent (alkyl•polyglycerin co-modified silicone having a siloxane dendron structure); Formulation weight ratio is 50:40:8 (decamethyl cyclopentasiloxane:titanium oxide: dispersing agent).

Production Method

A: Mix components 1 to 6.
B: Mix and dissolve components 9 to 11 and 13. Add the mixture to A and mix/emulsify.
C: Add components 7, 8, and 12 to B so as to form a uniform mixture.

Effects

The UV blocking water-in-oil emulsion spreads easily, is light on the skin, is free of stickiness and oiliness, has a feeling of sheerness, and has excellent cosmetic retainability. Additionally, there is nearly no change due to heat or the passage of time and useability and stability are both superior.

Formulation Example 25: Sunscreen Agent

| (Component) | (wt. %) |
|---|---|
| 1. Dimethylpolysiloxane (6 cSt) | 5.0 |
| 2. 9040 Silicone Elastomer Blend[*14] | 5.0 |
| 3. Glyceryl triisooctanoate | 3.0 |
| 4. Methyl trimethicone | 2.5 |
| 5. SS-3408[*1] | 1.5 |
| 6. Silicone Compound No. 1 | 1.0 |
| 7. Octylmethoxycinnamate | 6.0 |
| 8. Decamethyl cyclopentasiloxane | 24.0 |
| 9. Fine participate zinc oxide[*22] | 25.0 |
| 10. Sodium chloride | 0.5 |
| 11. 1,3-butylene glycol | 2.0 |
| 12. Purified water | 24.5 |
| 13. Perfume | q.s. |

Note
[*14]Product in which crosslinking organopolysiloxane (dimethicone crosspolymer) is diluted using decamethyl cyclopentasiloxane (elastomer component: 12%)

Note
[*1]Caprylyl methicone

Note
[*22]A powder composition prepared by performing surface coating with an alkyl•polyglycerin co-modified silicone having a siloxane dendron structure; wherein 7.1 parts of the surface treatment agent is dissolved in isopropyl alcohol, 28.6 parts of the powder is added and dispersed therein, and the solvent is removed by distillation.

Production Method

A: Uniformly mix components 1 to 6 and then add components 8 and 9.
B: Mix and dissolve components 10 to 12. Add the mixture to A and mix/emulsify.
C: Add component 7 to B and uniformly mix. Thus, a sunscreen agent is obtained.

Effects

The sunscreen agent has excellent dispersion stability of powder and does not easily agglomerate due to changes in temperature or passage of time. When applying, the sunscreen agent displays a smooth feeling to touch and spreads easily, and a cosmetic film with a feeling of sheerness and that is free of stickiness is obtained. Cosmetic retainability is excellent and, as a result, superior durability (sunblocking effect) is obtained.

Formulation Example 26: Water-in-Oil Emulsion Sunscreen

| (Component) | (wt. %) |
|---|---|
| 1. SH 556[*13] | 1.0 |
| 2. Octylmethoxycinnamate | 5.0 |
| 3. Fine particulate zinc oxide[*22] | 25.0 |
| 4. Silicone Compound No. 1 | 5.0 |
| 5. Dipropylene glycol | 5.0 |
| 6. PEG(10)/PPG(14) dimethylether | 1.5 |
| 7. Sodium carboxymethylcellulose | 0.1 |
| 8. Succinoglycan | 0.3 |
| 9. Chelating agent | q.s. |
| 10. Preservative | q.s. |
| 11. Buffer | q.s. |
| 12. Purified water | 57.1 |

Note
[*13]Phenyl trimethicone

Note
[*22]A powder composition prepared by performing surface coating with an alkyl•polyglycerin co-modified silicone having a siloxane dendron structure; wherein 7.1 parts of the surface treatment agent is dissolved in isopropyl alcohol, 28.6 parts of the powder is added and dispersed therein, and the solvent is removed by distillation.

Production Method

A: Uniformly mix components 1, 2, and 4 and then add component 3.
B: Mix and dissolve components 5 to 12 and add A thereto. Then, agitate/emulsify the mixture. Thus, a sunscreen agent is obtained.

Effects

A natural finish with a feeling of sheerness is obtained and a rich moisturizing feel lasts. Moreover, the sunscreen agent displays superior UV ray blocking effects in both the UVA region and the UVB region.

Formulation Example 27: Water-in-Oil Emulsion-Type Sunscreen

| (Component) | (wt. %) |
|---|---|
| 1. Silicone treated iron oxide-containing zinc oxide | 29.0 |
| 2. Silicone Compound No. 1 | 4.0 |
| 3. Decamethyl cyclopentasiloxane | 29.0 |
| 4. Methyl trimethicone (M3T) | 5.0 |
| 5. Isononyl isononanoate | 2.0 |
| 6. Octyl methoxycinnamate | 7.0 |
| 7. Polymethyl silsesquioxane powder | 4.0 |
| 8. Purified water | 13.9 |
| 9. Ethanol | 2.0 |
| 10. Glycerin | 3.0 |
| 11. Carboxyvinyl powder (1% aqueous solution) | 1.0 |
| 12. Sodium chloride | 0.1 |

Production Method

A: Uniformly mix components 1 to 4 using a three-roller mill.
B: Add A to components 5 to 7 and uniformly mix.
C: Add components 8 to 12 to B and uniformly emulsify/mix.
D: Degas C. Thus, a sunscreen is obtained.

Effects

Transparency of the cosmetic film is high and there is no ash-like color when applying. Stickiness particular to suncare products is reduced. Spreadability of the sunscreen is extremely good. The sunscreen displays superior, lasting skin moisturizing effects, excellent product stability over time, and is not prone to agglomeration.

Formulation Example 28: Sun Tanning Cream

| (Component) | (wt. %) |
|---|---|
| 1. SS-3408*1 | 12.0 |
| 2. Dimethylpolysiloxane (2 cSt) | 3.0 |
| 3. Mineral oil | 5.0 |
| 4. Alkyl-modified silicone resin wax | 0.5 |
| 5. Alkyl•polyether co-modified silicone having a siloxane dendron structure | 2.2 |
| 6. Silicone Compound No. 1 | 6.0 |
| 7. Palmitate | 0.2 |
| 8. Dimethyloctylparaaminobenzoic acid | 0.5 |
| 9. 4-t-butyl-4'-methoxy-dibenzoylmethane | 0.5 |
| 10. Kaolin | 0.5 |
| 11. Red iron oxide | 0.2 |
| 12. Yellow iron oxide | 0.3 |
| 13. Black iron oxide | 0.1 |
| 14. Titanium oxide coated mica | 1.0 |
| 15. Sodium L-glutamate | 3.0 |
| 16. 1,3-butylene glycol | 5.0 |
| 17. Dimethyldioctadecylammonium chloride | 0.1 |
| 18. Antioxidant | q.s. |
| 19. Preservative | q.s. |
| 20. Perfume | q.s. |
| 21. Purified water | remainder |

Note
*1)Caprylyl methicone

Production Method
A: Heat and dissolve components 1 to 9 and components 18 and 19.
B: Heat and agitate component 17 and a portion of component 21. Then, add and disperse components 10 to 14.
C: Uniformly dissolve components 15 and 16 and the remainder of component 21, and mix with B.
C: While agitating, add C to A in small amounts and emulsify. Cool the emulsion and add component 20. Thus, a sun tanning cream is obtained.

Effects
Changes such as separation due to temperature or the passage of time and agglomeration of the powder do not occur, and the sun tanning cream has superior stability. Moreover, spreadability is good and superior moisturizing feel is displayed.

Formulation Example 29: Liquid Rouge

| (Component) | (wt. %) |
|---|---|
| 1. Silicone Compound No. 1 | 7.0 |
| 2. Alkyl•polyether co-modified silicone having a siloxane dendron structure | 6.0 |
| 3. Silicic anhydride (average primary particle size: 10 nm) | 1.5 |
| 4. Diisostearyl malate | 15.0 |
| 5. Octyldodecanol | 4.0 |
| 6. SS-3408*1) | 1.0 |
| 7. Isododecane | 3.0 |
| 8. Isohexadecane | 2.0 |
| 9. Heavy liquid isoparaffin | 30.0 |
| 10. Squalane | 9.0 |
| 11. Sunflower oil | 5.0 |
| 12. Trioctanoin | 5.0 |
| 13. Vaseline | 2.0 |
| 14. Microcrystalline wax | 2.0 |
| 15. Red No. 202 | 0.8 |

-continued

| (Component) | (wt. %) |
|---|---|
| 16. Titanium oxide | 0.7 |
| 17. Titanium oxide covered glass powder | 2.0 |
| 18. Titanium oxide covered silica powder | 2.0 |
| 19. Nε-lauroyl-L-lysine | 2.0 |

Note
*1)Caprylyl methicone

Production Method
Mix and heat components 4 to 12 to 90° C. Thereafter, add and uniformly disperse component 3 using a homo-mixer. Then, add components 1 and 2. Add components 13 to 19 while holding the temperature at 90° C. Mix the mixture using a homo-mixer, charge it into a container, and cool. Thus, a liquid rouge is obtained.

Effects
The rouge applies smoothly and easily to the lips and has a sensation during use that is free of stickiness and has excellent gloss on the lips. Additionally, the rouge can protect the lips against drying.

Formulation Example 30: Rouge

| (Component) | (wt. %) |
|---|---|
| 1. Carnauba wax | 0.5 |
| 2. Candelilla wax | 5.0 |
| 3. Ceresin | 10.0 |
| 4. Squalane | 25.0 |
| 5. Isododecane | 2.0 |
| 6. Isohexadecane | 2.0 |
| 7. Methyl trimethicone (M3T) | 1.0 |
| 8. Glycerin triisostearate | 9.0 |
| 9. Alkyl•polyglycerin co-modified silicone having a siloxane dendron structure | 3.0 |
| 10. Glycerin diisostearate | 18.0 |
| 11. Hydroxypropyl-β-cyclodextrin | 1.0 |
| 12. Cholesterol stearate | 3.5 |
| 13. Red iron oxide coated with silicone compound No. 1*23 | 0.2 |
| 14. Glycerin | 0.5 |
| 15. Purified water | 2.0 |
| 16. Colorant | q.s. |
| 17. Perfume | q.s. |
| 18. Preservative | q.s. |

Note
*23Product in which 3% silicone compound is added to red iron oxide and then heated.

Production Method
A: Heat component 12 to 60° C. Then, add and mix component 13 therewith so as to be uniformly dispersed.
B: Separately, mix, heat, and melt component 11 and about 0.5% of component 15.
C: Add B to A while agitating and mix so as to be uniformly dispersed.
D: Next, add the remainder of component 15 (about 1.5%) and component 14 to C and mix. Thus, a hydrate composition is obtained.
E: Melt components 1 to 10 at 80° C. While agitating, add D thereto and uniformly disperse.
F: Add components 16 to 18 to E and disperse/agitate. Then, mold the product. Thus, a rouge is obtained.

Effects
The hydroxypropylated β cyclodextrin, water, cholesterol ester, and hydrate composition covered with the silicone compound No. 1 are stably compounded in the rouge. As a result, the product displays excellent moisture retaining capability, has superior moisture durability, and has excellent moisturizing effects.

Formulation 31: Lipstick

| (Component) | (wt. %) |
| --- | --- |
| 1. Polyethylene-polypropylene copolymer | 5.0 |
| 2. Candelilla wax | 5.0 |
| 3. Carnauba wax | 5.0 |
| 4. Vaseline | 10.0 |
| 5. Cetyl 2-ethylhexanoate | 10.0 |
| 6. Diglycerindiisostearate | 14.5 |
| 7. Macadamia nut oil | 7.0 |
| 8. Isododecane | 2.0 |
| 9. Isohexadecane | 1.0 |
| 10. Inulin stearate (Rheopearl ISK2; manufactured by Chiba Flour Milling Co., Ltd.) | 20.0 |
| 11. Silicone Compound No. 1 | 2.0 |
| 12. Red No. 201 | 1.0 |
| 13. Red No. 202 | 3.0 |
| 14. Yellow No. 4 aluminum lake | 3.0 |
| 15. Titanium oxide | 1.0 |
| 16. Black iron oxide | 0.5 |
| 17. Iron oxide titanated mica | 10.0 |
| 18. Preservative | q.s. |
| 19. Perfume | q.s. |

Production Method

A: Heat and dissolve components 1 to 11. Then, add components 12 to 18 and mix uniformly.

B: Add component 19 to A, and fill a container with the mixture. Thus, a lipstick is obtained.

Effects

The lipstick has a rich feeling to touch and can be applied smoothly. During use, the lipstick is free of stickiness and prevents drying of the lips. Moreover, beautiful color development and luster is obtained and cosmetic retainability is excellent.

Formulation Example 32: Rouge

| (Component) | (wt. %) |
| --- | --- |
| 1. Microcrystalline wax | 10.0 |
| 2. Paraffin wax | 15.0 |
| 3. Carnauba wax | 5.0 |
| 4. Vaseline | 5.0 |
| 5. Diisostearyl malate | 7.0 |
| 6. Glyceryl triisostearate | 9.5 |
| 7. Propylene glycol dicaprate | 7.0 |
| 8. Inulin stearate (Rheopearl ISK2; manufactured by Chiba Flour Milling Co., Ltd.) | 2.0 |
| 9. Silicone Compound No. 1 | 3.0 |
| 10. Alkyl•polyether co-modified silicone having a siloxane dendron structure | 2.0 |
| 11. Decamethyl cyclopentasiloxane | 10.0 |
| 12. FA 4001 CM*[15] | 3.0 |
| 13. DC 593*[10] | 2.0 |
| 14. Red No. 201 | 1.0 |
| 15. Red No. 202 | 1.0 |
| 16. Yellow No. 4 | 2.0 |
| 17. Titanium oxide | 4.0 |
| 18. Black iron oxide | 0.5 |
| 19. Iron oxide titanated mica | 3.0 |
| 20. Titanated mica | 2.0 |
| 21. Purified water | 5.0 |
| 22. 1,3-butylene glycol | 1.0 |
| 23. Preservative | q.s. |
| 24. Perfume | q.s. |

Note
*[15]Decamethyl cyclopentasiloxane solution of (acrylates/polytrimethylsiloxy methacrylate) copolymer (active component: 30 wt. %)
Note
*[10]Dimethylpolysiloxane (100 cSt) solution of trimethylsiloxysilicate (active component: 33%)

Production Method

A: Heat and dissolve components 1 to 13. Then, add components 14 to 20 and mix uniformly.

B: Uniformly mix components 21 to 23 and, thereafter, add A and mix.

C: Add component 24 to B, and fill a container with the mixture. Thus, a rouge is obtained.

Effects

The lipstick has a rich feeling to touch and can be applied smoothly. During use, the lipstick is free of stickiness and prevents drying of the lips. Additionally, the emulsion stability of the product is extremely good.

Formulation Example 33: Lip Gloss

| (Component) | (wt. %) |
| --- | --- |
| 1. Dimer dilinoleyl hydrogenated rosin condensate | 5.0 |
| 2. Dimer dilinoleyl diisostearate | 10.0 |
| 3. Isotridecyl isononanoate | 10.0 |
| 4. SH 556 FLUID*[13] | 5.0 |
| 5. Decamethyl cyclopentasiloxane | 2.5 |
| 6. Hydrogenated polyisobutene | 35.5 |
| 7. Hydrogenated polystyrene/isoprene copolymer, hydrogenated polydecene | 30.0 |
| 8. Silicone Compound No. 1 | 2.0 |

Note
*[13]Phenyl trimethicone

Production Method

A: Heat components 1 to 8 at 40 to 50° C., and then mix and disperse uniformly.

B: Degas the mixture and then mold the mixture by charging it into a container and allowing it to sit at room temperature.

Effects

A discomfort free lip gloss that provides a natural feeling on the skin is obtained. An appropriate and pleasant moisturizing feel lasts on the surface of the skin. The lip gloss is free of color and oil stains and the moisturizing feel lasts.

Formulation Example 34: Mascara

| (Component) | (wt. %) |
| --- | --- |
| 1. FA 4002 ID*[9] | 19.0 |
| 2. Palmitate/dextrin ethylhexanoate | 8.0 |
| 3. Polyethylene wax | 3.5 |
| 4. Beeswax | 6.5 |
| 5. Lecithin | 0.5 |
| 6. SS-3408*[1] | 21.0 |
| 7. $C_{11-12}$ fluid isoparaffin | 19.0 |
| 8. Silicone Compound No. 1 | 4.0 |
| 9. Iron oxide | 5.0 |
| 10. Aerosil RY200*[24] | 3.5 |
| 11. Talc | 10.0 |

Note
*[9]Isododecane solution of (acrylates/polytrimethylsiloxy methacrylate) copolymer (active component: 40%)
Note
*[1]Caprylyl methicone
Note
*[24]Aerosil RY200 (manufactured by Nippon Aerosil Co., Ltd.): Hydrophobized silica Production Method A: Thoroughly mix and dissolve components 1 to 8. As necessary, heat the mixture to 40° C.

B: Add components 9 to 11 to A and disperse using a roller.

Effects

The mascara spreads easily, is free of stickiness and oiliness, has moisture resistance, water repellency, and anti-perspirant properties, and has excellent cosmetic retainability. The mascara also has superior stability and does not vary with temperature or time.

Formulation Example 35: Mascara

| (Component) | (wt. %) |
|---|---|
| 1. Isododecane | 23.0. |
| 2. Isohexadecane | 1.0 |
| 3. Dimethyl palmityl polysiloxane | 1.0 |
| 4. Dimethylpolysiloxane (100,000 cSt) | 1.0 |
| 5. Microcrystalline wax | 5.0 |
| 6. Beeswax | 3.0 |
| 7. Silicone Compound No. 1 | 3.0 |
| 8. Silicone coated black iron oxide | 14.0 |
| 9. Bentonite | 2.0 |
| 10. Nylon fiber (average length: 2 μm) | 2.0 |
| 11. Paraoxybenzoic acid ester | 0.5 |
| 12. Absolute ethanol | 2.5 |
| 13. Polyvinylalcohol | 0.5 |
| 14. Alkyl acrylate copolymer emulsion (50% dispersion liquid) | 19.5 |
| 15. Alkyl acrylate-styrene copolymer emulsion (50% dispersion liquid) | 8.0 |
| 16. Purified water | 14.0 |

Production Method

A: Mix and dissolve components 1 to 7. Then, add and uniformly disperse components 8 to 10 while agitating using a homo-disper mixer.
B: Dissolve component 11 in component 12 and add and uniformly blend this mixture with component 16.
C: Uniformly mix B with components 14 and 15. Then, add component 13 and uniformly mix.
D: Add A in small amounts to C while agitating using a homo-disper mixer. Thus, a mascara is obtained.

Effects

The mascara spreads easily and has a sensation during use that has little stickiness or oiliness. A mascara with superior durability can be obtained that has moisture resistance, water repellency, anti-perspirant properties, and that is not easily displaced due to light impacts. Additionally, stability of the product itself is excellent with regard to temperature and the passage of time.

Formulation Example 36: Mascara

| (Component) | (wt. %) |
|---|---|
| 1. Decamethyl cyclopentasiloxane | 19.4 |
| 2. Light liquid isoparaffin | 14.6 |
| 3. Methyl trimethicone (M3T) | 1.5 |
| 4. FA 4001 CM*[15] | 31.0 |
| 5. Dextrin fatty ester | 14.0 |
| 6. Silicone Compound No. 1 | 3.0 |
| 7. Alkyl·glycerin co-modified silicone having a siloxane dendron structure | 1.0 |
| 8. Organo-modified bentonite | 1.5 |
| 9. Hydrophobized silicic anhydride | 2.0 |
| 10. Nylon fiber (average length: 2 μm) | 2.0 |
| 11. Carbon black | 10.0 |

Note
*[15]Decamethyl cyclopentasiloxane solution of (acrylates/polytrimethylsiloxy methacrylate) copolymer (active component: 30%)

Production Method

Uniformly mix components 1 to 11. Then, fill a container with the mixture. Thus, a mascara is obtained.

Effects

The mascara spreads easily and is free of stickiness and oiliness. Additionally, because the mascara has superior moisture resistance, water repellency, and anti-perspirant properties, cosmetic retainability is good. Additionally, there is nearly no change due to heat or the passage of time and stability is superior.

Formulation Example 37: Eye Shadow

| (Component) | (wt. %) |
|---|---|
| 1. Decamethyl cyclopentasiloxane | 13.0 |
| 2. Dimethylpolysiloxane (6 cSt) | 10.0 |
| 3. Methyl trimethicone (M3T) | 2.0 |
| 4. Silicone Compound No. 1 | 2.0 |
| 5. PEG(10)lauryl ether | 0.5 |
| 6. Silicone treated chromium oxide*[25] | 6.2 |
| 7. Silicone treated ultramarine blue*[25] | 4.0 |
| 8. Silicone treated titanium-coated mica*[25] | 6.0 |
| 9. Sodium chloride | 2.0 |
| 10. Propylene glycol | 8.0 |
| 11. Preservative | q.s. |
| 12. Perfume | q.s. |
| 13. Purified water | 46.3 |

Note
*[25]Silicone treatment: 3% methylhydrogenpolysiloxane was added to the powder and then heated.

Production Method

A: Mix components 1 to 5 and add and uniformly disperse components 6 to 8 therein.
B: Uniformly dissolve components 9 to 11 and 13.
C: While agitating, add B to A in small amounts and emulsify. Then, add component 12. Thus, an eye shadow is obtained.

Effects

The eye shadow spreads easily, is free of oiliness and powderiness, and has a refreshing, clean sensation during use that lasts. With the eye shadow, compatibility with the skin is good, moisture resistance, water repellency, and anti-perspirant properties are excellent. Therefore, make up does not smear easily. The eye shadow also has superior stability and does not vary with temperature or time.

Formulation Example 38: Solid Powder Eye Shadow

| (Component) | (wt. %) |
|---|---|
| 1. Talc (hydrophobization-treated) | 16.0 |
| 2. Sericite (hydrophobization-treated) | 30.0 |
| 3. Titanated mica (hydrophobization-treated) | 35.0 |
| 4. Ultramarine blue (hydrophobization-treated) | 4.0 |
| 5. Iron oxide (hydrophobization-treated) | 2.0 |
| 6. SS-2910*[2] | 5.0 |
| 7. Silicone Compound No. 1 | 5.0 |
| 8. Tetrakistrimethylsiloxysilane (M4Q) | 2.0 |
| 9. Liquid paraffin | 0.5 |
| 10. Paraffin | 0.5 |

Note
*[27]Polyether-modified silicone

Production Method

A: Agitate/mix components 1 to 5 using a blender.
B: Heat and dissolve components 6 to 10.
C: Blast B onto A and agitate further. Thereafter, crush the resulting product and compress it using a molding machine. Thus, a solid powder eye shadow is obtained.

Effects

Sensation during use and finish of the solid powder eye shadow are superior. Bonding of the powder is excellent and superior moisture resistance, water repellency, and anti-perspirant properties is displayed. Therefore, cosmetic retainability is excellent.

Formulation Example 39: Anti-Perspirant Aerosolized Cosmetic Composition

| (Component) | (wt. %) |
|---|---|
| 1. Aluminum hydroxy chloride | 3.0 |
| 2. Zinc oxide | 2.0 |
| 3. Silica | 3.0 |
| 4. Silver ion/zinc ion/ammonium ion-carrying zeolite | 1.0 |
| 5. Calcium stearate | 0.1 |
| 6. Dimethylpolysiloxane (6cs) | 2.0 |
| 7. Cetyl octonoic acid | 1.0 |
| 8. Liquid paraffin | 1.0 |
| 9. Isohexadecane | 5.0 |
| 10. Silicone Compound No. 1 | 5.0 |
| 11. Sorbitan oleic acid | 1.0 |
| 12. Antioxidant | q.s. |
| 13. Perfume | q.s. |
| 14. Liquified petroleum gas | Remainder |

Production Method

A: Mix components 6 to 13 (oil phase portion) so as to form a uniform liquid.
B: Mix and uniformly disperse components 1 to 5 (powders) in the oil phase portion.
C: Charge component 14 (propellant). Thus, an anti-perspirant aerosolized cosmetic is obtained.

Effects

Adhesion of the powder is excellent, whiteness after use is not noticeable, and safety is high. The aerosol anti-perspirant composition is free of stickiness after application, and provides an appropriate dry sensation. Moreover, a smooth, natural feeling on the skin can be obtained.

Formulation Example 40: Nonaqueous Pressurized Anti-Perspirant Product

| (Component) | (wt. %) |
|---|---|
| 1. 15 wt. % 1,2-hexanediol solution of aluminum chlorohydrate | 12.0 |
| 2. Dimethylpolysiloxane (10 cSt) | 3.0 |
| 3. Decamethyl cyclopentasiloxane | 3.0 |
| 4. Silicone Compound No. 1 | 3.0 |
| 5. Perfume | 1.0 |
| 6. Butane | 25.0 |
| 7. Isobutane | 30.0 |
| 8. Propane | 3.0 |
| 9. Dimethyl ether | 20.0 |

Production Method

A: Mix components 1 to 5 so as to form a uniform liquid.
C: Charge components 6 to 8 (propellants).
C: Lastly, charge component 9 (propellant). Thus, a non-aqueous pressurized anti-perspirant product is obtained.

Effects

A transparent, uniform, pressurized liquid can be obtained and, therefore, separation of the AP active components and the like does not occur and product life is long. The nonaqueous pressurized anti-perspirant product provides instant anti-perspirant effects and whiteness is not noticeable after use. A natural, moisturized feeling on the skin after application can be obtained.

Formulation Example 41: Anti-Perspirant Lotion Composition

| (Component) | (wt. %) |
|---|---|
| 1. Aluminum hydroxy chloride | 5.0 |
| 2. POE(15) POP(5) cetyl ether phosphate | 5.0 |
| 3. Purified water | 5.0 |
| 4. Talc | 0.4 |
| 5. Regular spherical shape silica | 0.4 |
| 6. Smectite | 0.4 |
| 7. Nylon powder | 0.4 |
| 8. Polyethylene powder | 0.4 |
| 9. Decamethyl cyclopentasiloxane | 1.0 |
| 10. SH 556 FLUID*[13] | 1.0 |
| 11. Polyether-modified silicone having a siloxane dendron structure | 1.0 |
| 12. Silicone Compound No. 1 | 0.5 |
| 13. Triclosan | 0.1 |
| 14. *Betula alba* extract | 0.1 |
| 15. Rosemary extract | 0.1 |
| 16. Perfume | 1.0 |
| 17. Ethanol | Balance |

Note
*[13]Phenyl trimethicone

Production Method

A: Mix and dissolve components 9 to 17 so as to form a uniform liquid.
B: Mix and dissolve components 1 to 3 in A.
C: Then, thoroughly mix and uniformly disperse components 4 to 8.

Effects

A transparent, uniform liquid agent can be obtained and, therefore, active components and the like do not separate and stability over time of the anti-perspirant lotion composition is excellent. Anti-perspirant effects are expressed rapidly, immediately after application to the skin. A feeling of tightness caused by evaporation of the ethanol after application is suppressed, and a natural feeling on the skin that is dry and free of stickiness is provided.

Formulation Example 42: W/O Solid Anti-Perspirant Stick Composition

| (Component) | (wt. %) |
|---|---|
| 1. Stearyl alcohol | 25.0 |
| 2. Behenyl alcohol | 0.5 |
| 3. Hydrogenated castor oil | 4.0 |
| 4. Polypropylene glycol (average molecular weight: 1,000) | 7.0 |
| 5. PPG-14 butyl ether | 1.0 |
| 6. Decamethyl cyclopentasiloxane | 32.0 |
| 7. Alkyl•polyether co-modified silicone having a siloxane dendron structure | 3.0 |
| 8. Silicone Compound No. 1 | 2.5 |
| 9. Aluminum-zirconium-tetrachlorohydrate-glycine | 25.0 |

Production Method

A: Dissolve components 1 to 3 and components 6 to 8 by heating and agitating at 80° C.
B: While maintaining a temperature of 65° C., add and dissolve components 4 and 5 while agitating.
C: While maintaining a temperature of 65° C., add and uniformly disperse component 9 by thoroughly agitating.

D: Pour the mixture into a container and solidify at room temperature.

Effects

The W/O solid anti-perspirant stick composition can be applied to the skin smoothly without resistance, and a pleasant, natural sensation during use can be obtained because a film thereof is free of stickiness and an appropriate degree of moisturizing feel is provided. White residue is, for the most part, unnoticeable after drying. Moreover, the durability of the anti-perspirant effects is excellent.

Formulation Example 43: Aerosol Type Anti-Perspirant Composition

| (Component) | (wt. %) |
| --- | --- |
| 1. Aluminum hydroxy chloride*[26] | 5.0 |
| 2. Aluminum hydroxy chloride*[27] | 1.5 |
| 3. Purified water | 10.0 |
| 4. POE(10) POP(5) cetyl ether phosphate | 1.5 |
| 5. Magnesia silica | 1.0 |
| 6. Porous silica | 0.5 |
| 7. Polymethyl silsesquioxane powder | 1.0 |
| 8. Decamethyl cyclopentasiloxane | 2.0 |
| 9. Silicone Compound No. 1 | 0.5 |
| 10. Isopropyl methylphenol | 0.05 |
| 11. *Eucalyptus globulus* leaf extract | 0.5 |
| 12. Soy extract | 0.1 |
| 13. *Melissa officinalis* leaf extract | 0.1 |
| 14. Apple extract | 0.1 |
| 15. Perfume M*[28] | 0.15 |
| 16. Ethanol | 26.0 |
| 17. LPG (0.15 MPa/20° C.) | 50.0 |

Note
*[26]REACH 101 MICRO-DRY (trade designation, manufactured by Reheis, Inc.)
Note
*[27]REACH 501 MICRO-DRY (trade designation, manufactured by Reheis, Inc.)
Note
*[28]Prepared according to the perfume composition examples shown in Table 9.

Production Method
A: Mix and dissolve components 1 to 4 so as to form a uniform liquid. (aqueous phase)
B: Separately, mix and dissolve components 8 to 16 so as to form a uniform liquid. (ethanol phase)
C: Thoroughly mix the aqueous phase and the ethanol phase so as to form a uniform liquid. (stock solution)
D: Mix with and uniformly disperse components 5 to 7 in the stock solution.
E: Lastly, charge component 17. Thus, an aerosol type anti-perspirant composition is obtained.

Effects

A transparent, uniform, pressurized liquid can be obtained and, therefore, separation of the anti-perspiration active components and the like does not occur and product life is long. Anti-perspirant effects are expressed rapidly, immediately after application to the skin. A natural, moisturized feeling on the skin after application that is free of stickiness can be obtained.

TABLE 4

| Perfume M | |
| --- | --- |
| Component | Content (%) |
| Aldehyde C-8 | 0.1 |
| Aldehyde C-9 | 0.1 |
| Aldehyde C-10 | 0.1 |
| Aldehyde C-11 Undecylenic | 0.1 |
| Aldehyde C-12 lauric | 0.1 |
| Allylheptanoate | 0.1 |
| Ambroxane | 0.1 |
| Bergamot oil | 4.0 |
| Citral | 1.0 |
| Citronellol | 8.0 |
| Citronellyl nitrile | 1.0 |
| Cyclamen aldehyde | 0.5 |
| Alpha-damascone | 0.1 |
| Beta-damascone | 0.1 |
| Dihydromyrcenol | 0.5 |
| Dipropylene glycol | 3.4 |
| Elemi Absolute | 3.0 |
| Ethyl vanillin | 0.1 |
| *Eucalyptus* oil | 0.5 |
| Galaxolide 50 benzyl benzoate | 12.0 |
| Gardamide | 0.3 |
| Geranyl nitrile | 1.0 |
| Grapefruit oil | 5.5 |
| Hedione | 3.5 |
| Helional | 1.0 |
| Cis-3-hexenol | 0.1 |
| Cis-3-hexenyl isobutyrate | 0.1 |
| Hexyl cinnamic aldehyde | 2.0 |
| Trans-2-hexenol | 0.2 |
| Indole pure | 0.1 |
| Ionone beta | 1.0 |
| Jasmacyclene | 3.0 |
| Juniper berry oil | 0.1 |
| Karanal | 0.1 |
| Lemon oil | 10.0 |
| Lemonile | 0.5 |
| Ligustral | 0.1 |
| Lilial | 2.0 |
| Lime oil | 2.0 |
| Linalol | 5.0 |
| Linalyl acetate | 1.5 |
| Lyral | 2.0 |
| Methyl heptenone | 1.0 |
| Nerol 900 | 1.0 |
| Orange oil | 3.0 |
| Orsolate | 0.5 |
| Pentalide | 1.0 |
| Phenylethyl phenylacetate | 0.5 |
| Phenylethyl alcohol | 1.0 |
| Pineapple base | 1.0 |
| Polysantole | 0.5 |
| Rhubafuran | 0.5 |
| Santalinol | 0.5 |
| Sweetie oil | 2.0 |
| Terpineol | 3.0 |
| Tetrahydro muguol | 0.5 |
| Tonalide | 8.0 |
| Total | 100.0 |

Formulation Example 44: W/O Solid Anti-Perspirant Stick Composition

| (Component) | (wt. %) |
| --- | --- |
| 1. Caprylyl methicone | 17.5 |
| 2. $C_{12\text{-}15}$ alkyl benzoate | 12.5 |
| 3. Polydecene | 11.3 |
| 4. Silicone Compound No. 1 | 6.9 |
| 5. β-sitosterol | 2.4 |
| 6. γ-orizanol | 2.4 |
| 7. Aluminum•zirconium•pentachlorohydrate | 18.8 |
| 8. Purified water | 18.8 |
| 9. Glycerin | 9.4 |

Production Method
A: Dissolve components 1 to 4 by heating and agitating at 80° C.
B: Add and dissolve components 5 and 6 while agitating and maintaining a temperature of 80° C.
C: Separately, mix and dissolve components 7 to 9, and then heat the mixture to 65° C.
D: Add C in small amounts and emulsify while agitating and maintaining the temperature of B at 65° C.
E: Allow the emulsion to sit at rest so as to degas the emulsion. Then, pour the emulsion into a container and solidify at room temperature.

Effects

The W/O solid anti-perspirant stick composition has a semi-transparent, high-quality appearance and appropriate stick hardness. The sensation of application is extremely smooth and refreshing, and the durability of the anti-perspirant effects is excellent. Moreover, there is no white residue after application.

Formulation Example 45: W/O Emulsion Type Anti-Perspirant Cream Composition

| (Component) | (wt. %) |
| --- | --- |
| 1. Mineral oil | 4.0 |
| 2. Cetearyl alcohol | 4.7 |
| 3. Glyceryl stearate | 2.0 |
| 4. PEG-20 stearate | 1.2 |
| 5. Silicone Compound No. 1 | 1.5 |
| 6. Phenoxyethanol | 0.4 |
| 7. Titanium oxide | 0.2 |
| 8. Glycerin | 6.0 |
| 9. Aluminum-zirconium tetrachlorohydrex glycine | 15.0 |
| 10. Purified water | 65.0 |

Production Method
A: Dissolve components 1 to 6 by heating at 80° C. and agitating.
B: While maintaining a temperature of 80° C. and agitating, add and uniformly disperse component 7 in A.
C: Separately, mix and dissolve components 8 to 10, and then heat the mixture to 65° C.
D: Add C in small amounts and emulsify while maintaining the temperature of B at 65° C. and agitating.

Effects

The cream has a smooth, natural sensation of application that is free of discomfort. Balance between immediate effects and durability of anti-perspirant and moisturizing effects is excellent. The cream provides moisture to the skin and restores elasticity. Moreover, for the most part, there is no white residue after application.

Formulation Example 46: Hair Conditioner

| (Component) | (wt. %) |
| --- | --- |
| 1. Cetanol | 5.6 |
| 2. Stearyltrimonium chloride | 1.5 |
| 3. Behentrimonium chloride | 0.8 |
| 4. Mineral oil | 1.0 |
| 5. Decamethyl cyclopentasiloxane | 3.0 |
| 6. Dimethylpolysiloxane (5,000 cSt) | 0.5 |
| 7. SH 556 FLUID*[13] | 2.0 |
| 8. Silicone Compound No. 1 | 0.5 |
| 9. Methylisothiazolinone | 0.1 |
| 10. EDTA-2Na | 0.1 |
| 11. Glycerin | 2.0 |
| 12. Purified water | 82.9 |

Note
*[13]Phenyl trimethicone

Production Method
A: Thoroughly mix components 1 to 8, and heat and agitate at 80° C. so as to form a uniform dispersion.
B: Separately, heat and dissolve components 10 to 12 at 80° C.
C: Emulsify the mixture by adding A to B in small amounts while agitating.
D: Cool C while agitating and add component 9 when the temperature is 40° C. or lower.

Effects

The hair conditioner spreads smoothly on the hair when applied and excellent smoothness lasts when rinsing with running water. Moreover, a clean, light, and excellent sliding feeling is provided to all parts of the hair, including the ends when towel-drying. Furthermore, conditioning effects after drying are superior (fingers pass through the hair easily and lightly, a sense of volume is provided, dryness is suppressed, and a natural luster is imparted).

Formulation Example 47: Hair Conditioner

| (Component) | (wt. %) |
| --- | --- |
| 1. Stearyltrimonium chloride | 1.44 |
| 2. Cetyl alcohol | 2.4 |
| 3. Octyldodecanol | 0.5 |
| 4. Cetyl ethylhexanoate | 0.6 |
| 5. Squalane | 0.2 |
| 6. Purified water | 89.86 |
| 7. Glycerin | 2.0 |
| 8. Preservative | q.s. |
| 9. Perfume | q.s. |
| 10. An O/W emulsion obtained by emulsifying a mixed liquid comprising Silicone compound No. 1 and dimethylpolysiloxane (2 cSt) at a ratio of 1:9 | 3.0 |
| 11. Citric acid | q.s. |

Production Method
A: Heat, mix, and dissolve components 1 to 5.
B: Heat, mix, and dissolve components 6 to 7.
C: Add the composition obtained in B to the composition obtained in A and emulsify.
D: Cool the composition obtained in C, add components 8 to 10, and thoroughly mix.
E: As necessary, add component 11.

Note that respective synergistic effects can be expected by further compounding, after Step C, a dimethylsilicone, a dimethylpolysiloxane (dimethiconol) capped at both molecular terminals with dimethyl silanol groups, a phenyl-modified silicone, an amino-modified silicone, an amino/polyether co-modified silicone, or similar emulsion; an aqueous dispersion of silicone elastomer powder, and/or a polyether-modified silicone or similar water-soluble silicone oil, or the like.

Formulation Example 48: Rinse-Type Hair Treatment

| (Component) | (wt. %) |
| --- | --- |
| 1. Cetyl alcohol | 5.6 |
| 2. Mineral oil | 1.0 |
| 3. Stearyltrimonium chloride | 1.2 |
| 4. Behentrimonium chloride | 0.64 |
| 5. Decamethyl cyclopentasiloxane | 2.3 |
| 6. Dimethicone (2 cSt) | 1.0 |
| 7. Dimethicone (5,000 cSt) | 1.0 |
| 8. SH 556 FLUID*[13] | 2.0 |
| 9. Silicone Compound No. 1 | 0.1 |
| 10. Glycerin-modified silicone having a siloxane dendron structure | 0.1 |
| 11. Glycerin | 2.0 |
| 12. EDTA-2Na | 0.1 |
| 13. Purified water | 82.76 |
| 14. Panthenol | 0.1 |
| 15. Tocopherol | 0.04 |
| 16. Lysine HCl | 0.02 |
| 17. Glycine | 0.02 |
| 18. Histidine | 0.02 |
| 19. Preservative | q.s. |
| 20. Perfume | q.s. |

Note
*[13]Phenyl trimethicone

Production Method

A: Heat, thoroughly mix, and dissolve components 1 to 10 so as to form a uniform dispersion.

B: Heat, mix, and dissolve components 11 to 13.

C: Add the composition obtained in B to the composition obtained in A and emulsify.

D: Cool the composition obtained in C, and add components 14 to 20.

Note that respective synergistic effects can be expected by further compounding a dimethylpolysiloxane (dimethiconol) capped at both molecular terminals with dimethyl silanol groups, a silicone wax, an amino-modified silicone, a long chain alkyl.amino co-modified silicone, an amino/polyether co-modified silicone, a polysilicone-13, or the like in addition to components 1 to 9 in Step A.

Formulation Example 49: Leave on-Type Hair Treatment

| (Component) | (wt. %) |
| --- | --- |
| 1. Cetyl alcohol | 4.0 |
| 2. Mineral oil | 1.0 |
| 3. Stearyltrimonium chloride | 1.0 |
| 4. Behentrimonium chloride | 0.2 |
| 5. Decamethyl cyclopentasiloxane | 1.4 |
| 6. Dimethicone (2 cSt) | 0.6 |
| 7. Dimethicone (5,000 cSt) | 0.6 |
| 8. SH 556 FLUID*[13] | 1.2 |
| 9. Silicone Compound No. 1 | 0.1 |
| 10. Glycerin | 2.0 |
| 11. EDTA-2Na | 0.1 |
| 12. Purified water | 87.6 |
| 13. Panthenol | 0.1 |
| 14. Tocopherol | 0.04 |
| 15. Lysine HCl | 0.02 |
| 16. Glycine | 0.02 |
| 17. Histidine | 0.02 |
| 18. Preservative | q.s. |
| 19. Perfume | q.s. |

Note
*[13]Phenyl trimethicone

Production Method

A: Heat, thoroughly mix, and dissolve components 1 to 9 so as to form a uniform dispersion.

B: Heat, mix, and dissolve components 10 to 12.

C: Add the composition obtained in B to the composition obtained in A and emulsify.

D: Cool the composition obtained in C, and add components 13 to 19.

Note that respective synergistic effects can be expected by further compounding a dimethylpolysiloxane (dimethiconol) capped at both molecular terminals with dimethyl silanol groups, a silicone wax, an amino-modified silicone, a long chain alkyl.amino co-modified silicone, an amino/polyether co-modified silicone, a polysilicone-13, or the like in addition to components 1 to 9 in Step A.

Formulation Example 50: Shampoo

| (Component) | (wt. %) |
| --- | --- |
| 1. POE(2) lauryl ether sodium sulfate (70% aqueous solution) | 17.86 |
| 2. Cocamide propyl betaine (30% aqueous solution) | 8.33 |
| 3. Cetanol | 0.50 |
| 4. Cationized cellulose (2% aqueous solution) | 25.00 |
| 5. Cationized guar gum | 0.05 |
| 6. Copolymer-type cationic polymer of dimethyldiallyl ammonium halide and acrylamide (9% aqueous solution) | 1.67 |
| 7. Sodium benzoic acid | 0.30 |
| 8. Glycol distearate | 1.00 |
| 9. An O/W emulsion obtained by emulsifying a mixed liquid comprising Silicone compound No. 1 and dimethylpolysiloxane (2 cSt) at a ratio of 1:9 | 5.00 |
| 10. Citric acid | 0.05 |
| 11. Purified water | 40.24 |

Production Method

A: Thoroughly mix and completely dissolve components 1 to 3 and components 7, 8, and 11 while maintaining a temperature of 70° C. and agitating.

B: Add components 4 to 6 to A and completely dissolve therein while maintaining a temperature of 70° C.

C: Cool B while agitating and add component 9 at a temperature of 55° C.

D: Further cool the mixture to room temperature, and add component 10 while agitating.

Effects

Foaming is excellent and a creamy, fine, uniform lather is obtained. Moreover, tactile sensation when washing hair is excellent. Furthermore, appropriate and natural smoothness is imparted to the hair, even when wet after rinsing.

Formulation Example 51: Shampoo

| (Component) | (wt. %) |
| --- | --- |
| 1. Purified water | 45.33 |
| 2. Polyquaternium-10 | 0.3 |

-continued

| (Component) | (wt. %) |
|---|---|
| 3. EDTA-2Na | 0.1 |
| 4. Glycerin | 1.5 |
| 5. Sodium laureth sulfate (27% aqueous solution) | 30.0 |
| 6. Sodium laureth-6 carboxylate (24% aqueous solution) | 10.0 |
| 7. Cocamide propyl betaine, NaCl (30% aqueous solution) | 10.0 |
| 8. Polyquaternium-7 | 0.27 |
| 9. Preservative | q.s. |
| 10. Perfume | q.s. |
| 11. Cocamide MEA | 2.0 |
| 12. An O/W emulsion obtained by emulsifying a mixed liquid comprising Silicone compound No. 1 and dimethylpolysiloxane (2 cSt) at a ratio of 1:9 | 0.5 |
| 13. Citric acid | q.s. |

Production Method

A: Heat, mix, and dissolve components 1 to 4.
B: Add components 5 to 7 to the composition obtained in A so as to form a uniform mixture.
C: Cool the composition obtained in B, add components 8 to 12, and thoroughly mix so as to form a uniform mixture.
D: As necessary, add component 13 to adjust the pH.

Note that respective synergistic effects can be expected by further compounding, after Step C, a dimethylsilicone, a dimethylpolysiloxane (dimethiconol) capped at both molecular terminals with dimethyl silanol groups, a phenyl-modified silicone, an amino-modified silicone, an amino/polyether co-modified silicone, or similar emulsion; an aqueous dispersion of silicone elastomer powder, and/or a polyether-modified silicone or similar water-soluble silicone oil, or the like.

Formulation Example 52: Hair Cream (Set-Type)

| (Component) | (wt. %) |
|---|---|
| 1. Carrageenan | 1.0 |
| 2. POE(60) hardened castor oil | 1.0 |
| 3. Carboxyvinyl polymer | 0.6 |
| 4. Triethanolamine | q.s. (pH = 7.5) |
| 5. Glycerin | 2.0 |
| 6. Perfume | q.s. |
| 7. Octylmethoxycinnamate | 0.1 |
| 8. Ethanol | 25.0 |
| 9. Purified water | 58.3 |
| 10. N-methacryloyloxydiethyl-N,N-dimethylaminoethyl-α-N-methylcarboxybetaine•alkylester methacrylate copolymer | 3.0 |
| 11. Alkyl acrylate copolymer TEA (30% ethanol solution) | 1.0 |
| 12. An O/W emulsion obtained by emulsifying a mixed liquid comprising Silicone compound No. 1 and dimethylpolysiloxane (2 cSt) at a ratio of 1:9 | 8.0 |

Production Method

A: Thoroughly mix and uniformly dissolve half the volume of component 9 and components 1 to 3 and component 5.
B: Place component 4 and components 6 to 8 in a separate container and uniformly dissolve them.
C: While agitating, add the remainder of component 9 in small amounts to B so as to form a uniform dispersion liquid.
D: While agitating, add components 10 and 11 in small amounts to the dispersion liquid of C so as to obtain a uniform viscous liquid.
E: While agitating, add component 12 in small amounts to D so as to obtain a uniform cream.

Effects

After application and until dry, the tactile sensation is smooth and a brush can be easily passed through the hair. Moreover, stickiness is minimal. After drying, the hair is free of stiffness and has natural smoothness. Furthermore, setting durability is also superior.

Formulation Example 53: Hair Mist

| (Component) | (wt. %) |
|---|---|
| 1. Purified water | 75.7 |
| 2. Sorbitol | 0.6 |
| 3. Creatine | 0.2 |
| 4. Urea | 1.0 |
| 5. 1,3-butylene glycol | 2.0 |
| 6. Preservative | q.s. |
| 7. Ethanol | 15.0 |
| 8. Glycereth-25 PCA isosteate | 0.5 |
| 9. Perfume | q.s. |
| 10. BY 25-339*[29] | 1.0 |
| 11. An O/W emulsion obtained by emulsifying a mixed liquid comprising Silicone compound No. 1 and dimethylpolysiloxane (2 cSt) at a ratio of 1:9 | 1.0 |
| 12. Bisethoxydiglycol cyclohexanedicarboxylate | 2.0 |
| 13. Hydroxypropyltrimonium starch chloride | 1.0 |

Note
*[29]Polyether-modified silicone

Production Method

A: Mix and dissolve components 1 to 6.
A: Mix and dissolve components 7 to 10.
C: Add the composition obtained in B to the composition obtained in A and solubilize the mixture.
D: Add components 11 to 13 to the composition obtained in C and mix thoroughly so as to obtain a uniform mixture.

Formulation Example 54: Hair Foam

| (Component) | (wt. %) |
|---|---|
| Stock solution | |
| 1. Copolymer of polyvinylpyrrolidone and vinyl acetate | 5.0 |
| 2. Vinylpyrrolidone•N,N-dimethylaminoethyl methacrylic acid copolymer diethyl sulfate salt | 0.5 |
| 3. SH 556 FLUID*[13] | 2.0 |
| 4. An O/W emulsion obtained by emulsifying a mixed liquid comprising Silicone compound No. 1 and dimethylpolysiloxane (2 cSt) at a ratio of 1:9 | 1.0 |
| 5. Ethanol | 12.0 |
| 6. Preservative | q.s. |
| 7. Perfume | q.s. |
| 8. Purified water | 79.5 |
| Charging formulation | |
| 9. Stock solution | 95.0 |
| 10. Liquid petroleum gas (LPG) | 5.0 |

Note
*[13]Phenyl trimethicone

Production Method

A: Thoroughly mix components 1 to 8 so as to form a uniform dispersion.
B: Charge the composition obtained in A (stock solution) into a container (can). After attaching a valve, charge component 10.

Formulation Example 55: Hair Spray

Stock Solution

| (Component) | (wt. %) |
| --- | --- |
| Stock Solution | |
| 1. Ethyl alcohol | 92.4 |
| 2. Alkanolamine liquid of acrylic resin (active ingredient = 50%) | 7.0 |
| 3. Cetyl alcohol | 0.1 |
| 4. An O/W emulsion obtained by emulsifying a mixed liquid comprising Silicone compound No. 1 and dimethylpolysiloxane (2 cSt) at a ratio of 1:9 | 0.5 |
| 5. Perfume | q.s. |
| Charging formulation | |
| 6. Stock Solution | 50.0 |
| 7. Dimethyl ether | 50.0 |

Production Method

A: Add component 2 to 5 to component 1 and thoroughly mix so as to form a uniform dispersion.

B: Filter the composition obtained in A.

C: Charge the composition obtained in B (stock solution) into a container (can). After attaching a valve, charge component 7.

Formulation Example 56: Hair Wax

| (Component) | (wt. %) |
| --- | --- |
| 1. Diethylhexyl succinate | 10.0 |
| 2. Squalane | 1.0 |
| 3. Shea butter | 1.0 |
| 4. Silicone Compound No. 1 | 2.0 |
| 5. Candelilla wax | 5.5 |
| 6. Microcrystalline wax | 6.0 |
| 7. Carnauba wax | 6.0 |
| 8. Ceteth-6 | 6.0 |
| 9. Ceteth-10 | 6.0 |
| 10. Glyceryl stearate (SE) soap impurities | 1.5 |
| 11. Hydroxystearic acid | 4.5 |
| 12. Purified water | 47.5 |
| 13. 1,3-butylene glycol | 3.0 |
| 14. Sodium hydroxide | q.s. |
| 15. PEG-90M | q.s. |
| 16. Preservative | q.s. |

Production Method

A: Heat, dissolve, and thoroughly mix components 1 to 11 so as to form a uniform dispersion.

B: Heat, mix, and dissolve components 12 to 14.

C: Add the composition obtained in B to the composition obtained in A and emulsify.

D: While heating, sequentially add components 15 and 16 to the composition obtained in B and thoroughly mix so as to form a uniform mixture.

E: Charge D into a container and solidify by cooling.

Note that respective synergistic effects can be expected by further compounding a silicone wax, an alkylsilicone resin wax, a polypropylsilsesquioxane, a long chain alkyl.amino co-modified silicone, an amino/polyether co-modified silicone, a polysilicone-13, or the like in addition to components 1 to 11 in Step A.

Formulation Example 57: Hair Cream

| (Component) | (wt. %) |
| --- | --- |
| 1. Vaseline | 4.0 |
| 2. Cetyl ethylhexanoate | 3.0 |
| 3. Silicone Compound No. 1 | 1.0 |
| 4. Isohexadecane | 2.0 |
| 5. Dimethicone (350 cSt) | 1.0 |
| 6. PEG-40 hydrogenated castor oil | 1.0 |
| 7. Polyacrylamide | 1.0 |
| 8. Purified water | 80.9 |
| 9. Glycerin | 3.0 |
| 10. Hydroxyethylcellulose | 0.1 |
| 11. Ethanol | 3.0 |
| 12. Preservative | q.s. |

Production Method

A: Heat and dissolve components 1 to 5 and thoroughly mix so as to form a uniform dispersion.

B: Heat components 6 to 9 and thoroughly mix so as to dissolve the components.

C: Add the composition obtained in A to the composition obtained in B and emulsify.

D: Add components 10 and 11 sequentially to the composition obtained in C and mix thoroughly so as to form a uniform mixture.

Note that respective synergistic effects can be expected by further compounding a dimethylsilicone, a dimethylpolysiloxane (dimethiconol) capped at both molecular terminals with dimethyl silanol groups, a silicone wax, a phenyl-modified silicone, an amino-modified silicone, a long chain alkyl.amino co-modified silicone, an amino/polyether co-modified silicone, a polysilicone-13, or the like in addition to components 1 to 5 in Step A.

Formulation Example 58: Hair Lotion

| (Component) | (wt. %) |
| --- | --- |
| 1. Carbomer | 0.4 |
| 2. Hydroxyethylcellulose | 0.1 |
| 3. PEG-6 | 1.5 |
| 4. Purified water | 88.2 |
| 5. Ethanol | 3.5 |
| 6. PEG-40 hydrogenated castor oil | 0.5 |
| 7. Trilaureth-4-phosphoric acid | 0.1 |
| 8. Cetyl ethylhexanoate | 2.0 |
| 9. An O/W emulsion obtained by emulsifying a mixed liquid comprising Silicone compound No. 1 and dimethylpolysiloxane (2 cSt) at a ratio of 1:9 | 1.2 |
| 10. FZ-4150*[30] | 2.5 |
| 11. Preservative | q.s. |
| 12. Sodium hydroxide | q.s. |

Note
*[30]An O/W emulsion obtained by emulsifying dimethicone using a polyether-modified silicone (active component: 30%)

Production Method

A: Heat, mix, and dissolve components 1 to 4.

B: Heat, mix, and dissolve components 5 to 7.

C: Add the composition obtained in B to the composition obtained in A and emulsify.

D: Add components 8 to 12 to the composition obtained in C and mix thoroughly so as to form a uniform mixture.

Note that respective synergistic effects can be expected by further compounding a dimethylsilicone, a dimethylpolysiloxane (dimethiconol) capped at both molecular terminals with dimethyl silanol groups, a phenyl-modified silicone, an amino-modified silicone, an amino/polyether co-modified silicone, or similar emulsion; an aqueous dispersion of silicone elastomer powder, a polyether-modified silicone or similar water-soluble silicone oil, or the like in addition to components 8 to 12 in Step D.

Formulation Example 59: Oil for Use on Hair

| (Component) | (wt. %) |
| --- | --- |
| 1. BY11-003*[31] | 67.0 |
| 2. Silicone Compound No. 1 | 3.0 |
| 3. Dimethicone (350 cSt) | 2.0 |
| 4. Decamethyl cyclopentasiloxane | 28.0 |
| 5. Perfume | q.s. |

Note
*[31]Decamethyl cyclopentasiloxane solution of dimethicone gum (dimethicone gum component: 10%)

Production Method
A: Appropriately heat components 1 to 4 and mix thoroughly so as to form a uniform dispersion.
B: Add component 5 to A and mix thoroughly so as to form a uniform mixture.

Note that respective synergistic effects can be expected by further compounding a dimethylpolysiloxane (dimethiconol) capped at both molecular terminals with dimethyl silanol groups, a silicone wax, a phenyl-modified silicone, an amino-modified silicone, a long chain alkyl.amino co-modified silicone, an amino/polyether co-modified silicone, a polysilicone-13, or the like in addition to components 1 to 4 in Step A.

Formulation Example 60: Oxidation-Type Hair Color

First Agent

| (Component) | (wt. %) |
| --- | --- |
| 1. Steareth-2 | 3.0 |
| 2. Steareth-21 | 2.0 |
| 3. Stearyl PPG-15 | 5.0 |
| 4. Cetostearyl alcohol | 4.0 |
| 5. Behenyl alcohol | 2.0 |
| 6. Silicone Compound No. 1 | 2.0 |
| 7. Behenyltrimethylammonium chloride | 0.8 |
| 8. Purified water | 69.4 |
| 9. EDTA-2Na | 0.5 |
| 10. Anhydrous sodium sulfite | 0.5 |
| 11. Sodium ascorbate | 0.1 |
| 12. 1,3-butylene glycol | 3.0 |
| 13. p-phenylenediamine | 0.25 |
| 14. p-aminophenol | 0.1 |
| 15. m-aminophenol | 0.05 |
| 16. Polyquaternium-39 | 0.3 |
| 17. Ammonium hydrogen carbonate | 2.0 |
| 18. Strong aqueous ammonia | 5.0 |

Production Method
A: Heat and dissolve components 1 to 7 and mix thoroughly so as to form a uniform dispersion.
B: Heat, mix, and dissolve components 8 to 15.
C: Add the composition obtained in A to the composition obtained in B and emulsify.
D: Add components 16 to 18 sequentially to the composition obtained in C and mix so as to form a uniform mixture.

Second Agent

| (Component) | (wt. %) |
| --- | --- |
| 1. Cetostearyl alcohol | 4.5 |
| 2. Sodium laurylsulfate | 0.5 |
| 3. Preservative | q.s. |
| 4. Etidronic acid | 0.1 |
| 5. Disodium hydrogen phosphate | 0.3 |
| 6. Purified water | 77.46 |
| 7. Hydrogen peroxide solution (35% aqueous solution) | 17.14 |
| 8. Phosphoric acid | q.s. |

Production Method
E: Heat and dissolve component 1.
F: Heat, mix, and dissolve components 2 to 6.
G: Add the component obtained in E to the composition obtained in F, and emulsify.
H: Cool the composition obtained in G, add component 7 and, as necessary, component 8, and mix thoroughly, so as to form a uniform mixture.

Formulation Example 61: Hair Manicure

| (Component) | (wt. %) |
| --- | --- |
| 1. Black No. 401 | 0.4 |
| 2. Purple No. 401 | 0.1 |
| 3. Orange No. 205 | 0.3 |
| 4. Benzyl alcohol | 5.0 |
| 5. Citric acid | 0.5 |
| 6. Hydroxyethylcellulose | 2.0 |
| 7. Stearyltrimethylammonium chloride | 0.5 |
| 8. PEG-40 hydrogenated castor oil | 0.5 |
| 9. An O/W emulsion obtained by emulsifying a mixed liquid comprising Silicone compound No. 1 and dimethylpolysiloxane (2 cSt) at a ratio of 1:9 | 1.0 |
| 10. Ethanol | 10.0 |
| 11. Preservative | q.s. |
| 12. Perfume | q.s. |
| 13. Purified water | 79.7 |
| 14. Sodium citrate | q.s. |

Production Method
A: Thoroughly mix and dissolve components 1 to 13.
B: Add component 14 to the composition obtained in A in order to adjust the pH.

Formulation Example 62: Permanent Setting Agent

First Agent

| (Component) | (wt. %) |
| --- | --- |
| 1. EDTA-2Na | 0.1 |
| 2. Etidronic acid | 0.1 |
| 3. Preservative | q.s. |
| 4. Purified water | 81.2 |
| 5. PEG-40 hydrogenated castor oil | 0.6 |
| 6. Perfume | 0.3 |
| 7. Ammonium thioglycolate (50% aqueous solution) | 13.0 |
| 8. Strong aqueous ammonia | 1.0 |
| 9. Monoethanolamine | 1.2 |
| 10. Ammonium hydrogen carbonate | 2.0 |
| 11. An O/W emulsion obtained by emulsifying a mixed liquid comprising Silicone compound No. 1 and dimethylpolysiloxane (2 cSt) at a ratio of 1:9 | 0.5 |
| 12. Phosphoric acid | q.s. |

Production Method
A: Appropriately heat, mix, and dissolve components 1 to 4.
B: Heat, mix, and dissolve components 5 and 6.

C: Sequentially add components 7 to 11 to the composition obtained in B and mix thoroughly so as to obtain a uniform mixture.
D: As necessary, add component 12 to the composition obtained in C and mix.
Second Agent

| (Component) | (wt. %) |
|---|---|
| 1. Polyquaternium-10 | 0.4 |
| 2. EDTA-2Na | 0.1 |
| 3. Preservative | q.s. |
| 4. Sodium dihydrogen phosphate | 0.05 |
| 5. Disodium hydrogen phosphate | 0.5 |
| 6. Purified water | 90.95 |
| 7. Sodium bromate | 8.0 |
| 8. pH adjusting agent | q.s. |

Preparation Procedure
E: Appropriately heat, mix, and dissolve components 1 to 6.
F: Add component 7 to the composition obtained in E. Component 8 is added thereto, if necessary.

Formulation Example 62: Liquid Foundation (W/O)

| (Components) | |
|---|---|
| 1. Isododecane | 20 parts |
| 2. Isohexadecane | 10 parts |
| 3. Isotridecyl isononanoate | 3 parts |
| 4. Glyceryl tricapryl-caprate | 2 parts |
| 5. Polyether-modified silicone*[1] | 1.5 parts |
| 6. Silicone Compound No. 1 | 0.5 parts |
| 7. Organo-modified clay mineral (Bentone 38V) | 1.5 parts |
| 8. Octyl methoxycinnamate | 5 parts |
| 9. Octylsilane treated titanium oxide | 8.5 parts |
| 10. Octylsilane treated red iron oxide | 0.4 parts |
| 11. Octylsilane treated yellow iron oxide | 1 part |
| 12. Octylsilane treated black iron oxide | 0.1 parts |
| 13. Dimethicone, dimethicone crosspolymer*[2] | 2 parts |
| 14. Isododecane/(acrylates/polytrimethylsiloxy methacrylate) copolymer*[3] | 1 part |
| 15. Trimethylsiloxysilicate | 1 part |
| 16. 1,3-butylene glycol | 5 parts |
| 17. Glycerin | 3 parts |
| 18. Sodium chloride | 0.5 parts |
| 19. Preservative | q.s. |
| 20. Purified water | remainder |
| 21. Perfume | q.s. |

Note
*[1]ES-5300, manufactured by Dow Corning Toray Co., Ltd.
Note
*[2]DC9045, manufactured by Dow Corning
Note
*[3]FA-4002ID, manufactured by Dow Corning Toray Co., Ltd.

Production Method
Step 1: Components 1, 2, 5, 7, 8, 13, 14, and 15 are agitated and mixed.
Step 2: Components 3, 4, and 9 to 12 are kneaded and mixed using a three-roll mill.
Step 3: While agitating, add the compound of Step 2 to the compound obtained in Step 1 and agitate/mix further.
Step 4: Add an aqueous phase formed by uniformly dissolving components 16 to 21 to the mixture obtained in Step 3, emulsify, and fill a container with the emulsion. Thus, a product is obtained.

During use, the resulting W/O liquid foundation has superior emulsion stability, moisture resistance, and cosmetic durability. Moreover, fineness is excellent, wrinkles are concealed, a light tactile sensation is provided, and durability of bonding and moisturizing effects is superior.

The invention claimed is:
1. A liquid organopolysiloxane having fluidity at a temperature of at least 100° C., a silicon-bonded glycerin derivative group, and a crosslinked structure comprising a carbon-silicon bond at the crosslinking portion,
wherein the glycerin derivative group is bonded to the silicon atom via a linking group that is at least divalent, comprising at least one type of hydrophilic unit selected from hydrophilic units represented by structural formulae (4-1) to (4-3) below:

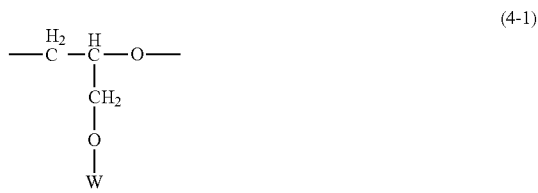

(4-1)

wherein W is a hydrogen atom or an alkyl group having from 1 to 20 carbons;

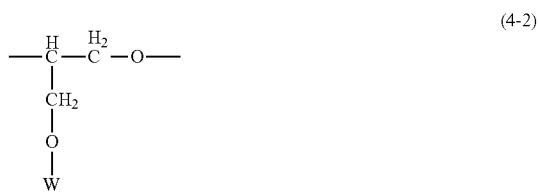

(4-2)

wherein W is as defined above; and

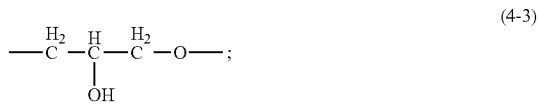

(4-3)

and an average value of the number of repetitions of the hydrophilic unit represented by the structural formulae (4-1) to (4-3) is in a range from 1.1 to 2.9; and
further comprising at least one monovalent organic group in the molecule which,
when expressed as a functional group $L^1$ and i=1, is a silylalkyl group having a siloxane dendron structure expressed by general formula (3) below:

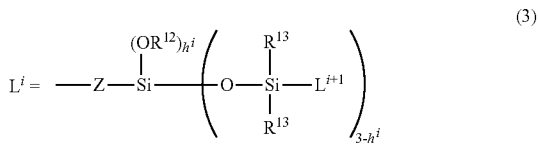

(3)

wherein $R^{12}$ is a substituted or unsubstituted, straight or branched monovalent hydrocarbon group having from 1 to 30 carbons;
$R^{13}$ are each independently a phenyl group or an alkyl group having from 1 to 6 carbons;
Z is a divalent organic group;
i represents a generation of the aforementioned silylalkyl group represented by $L^i$ and is an integer of 1 to k when k is a number of generations that is a number of repetitions of the silylalkyl group; the number of generations k is an integer from 1 to 10; $L^{i+1}$ is the silylalkyl group when i is less than k, and the $R^{13}$ moiety when i=k; and $h^i$ is a number in a range of 0 to 3.

2. The liquid organopolysiloxane according to claim 1, wherein the glycerin derivative group is a glycerin derivative group-containing organic group bonded to the silicon atom via a linking group that is at least divalent.

3. The liquid organopolysiloxane according to claim 1, wherein the glycerin derivative group is a hydrophilic segment bonded to the silicon atom via a linking group that is at least divalent, comprising at least one linearly bonded hydrophilic unit selected from the hydrophilic units represented by the structural formulae (4-1) to (4-3) above; or the glycerin derivative group is a glycerin derivative group-containing organic group bonded to the silicon atom via a linking group that is at least divalent, comprising at least one type of hydrophilic unit selected from the hydrophilic units represented by the structural formulae (4-1) to (4-3) above, and a branch unit selected from groups represented by structural formulae (4-4) to (4-6) below:

$$\begin{array}{c} H_2C-O-\\ \overset{H_2}{\underset{|}{C}}-CH-O- \end{array} \quad (4\text{-}4)$$

$$\begin{array}{c} H_2C-O-\\ |\\ -O-CH-O- \end{array} \quad (4\text{-}5)$$

$$\begin{array}{c} H_2C-O-\\ |\\ -CH-CH_2-O-. \end{array} \quad (4\text{-}6)$$

4. The liquid organopolysiloxane according to claim 1, wherein the glycerin derivative group is a diglycerin derivative group-containing organic group expressed by general formula (5-1) below:

$$\diagdown_R\diagup^O\diagdown\underset{OH}{\diagup}\diagdown^O\diagdown\underset{OH}{\diagup}\diagdown_{OH} \quad (5\text{-}1)$$

wherein R is a divalent organic group; or general formula (5-2) below:

$$\text{(5-2)}$$
HO—/—OH
  |
  O
  |
\_R—O—/—OH wherein R is as defined above.

5. The liquid organopolysiloxane according to claim 1, further comprising at least one additional monovalent organic group in the molecule selected from:

a substituted or unsubstituted, straight or branched monovalent hydrocarbon group having from 9 to 60 carbons; and an alkyl group substituted by a chain polysiloxane structure expressed by general formula (4) below:

$$-C_tH_{2t}\left[\begin{array}{c}R^{14}\\|\\Si-O\\|\\R^{14}\end{array}\right]_r\begin{array}{c}R^{14}\\|\\Si-R^{14}\\|\\R^{14}\end{array} \quad (4)$$

wherein $R^{14}$ are each independently substituted or unsubstituted, straight or branched monovalent hydrocarbon groups having from 1 to 30 carbons, hydroxyl groups, or hydrogen atoms and at least one of the $R^{14}$ moieties is the monovalent hydrocarbon group; t is a number in a range from 2 to 10; and r is a number in a range from 1 to 100.

6. The liquid organopolysiloxane according to claim 1, obtained by reacting:
(A) an organohydrogenpolysiloxane;
(B) a glycerin derivative group-containing organic compound having reactive unsaturated group; and
(C) at least one type of organic compound selected from the group consisting of (C1) an organic compound having an average number of reactive unsaturated group in the molecule that is greater than 1 and (C2) an organic compound having not less than one reactive unsaturated group and not less than one epoxy group in the molecule.

7. The liquid organopolysiloxane according to claim 6 wherein an average value of a number of silicon-bonded hydrogen atoms per molecule of the component (A), which reacts with the reactive unsaturated groups of the component (C) constituting the crosslinking portion, is greater than 0.1 and less than 2.0.

8. The liquid organopolysiloxane according to claim 6, wherein the component (A) is expressed by average composition formula (1): $R^1_a H_b SiO_{(4-a-b)/2}$ (1) wherein $R^1$ are each independently monovalent organic groups, $1.0 \leq a \leq 3.0$, and $0.001 \leq b \leq 1.5$.

9. The liquid organopolysiloxane according to claim 6, wherein the component (C) is at least one organic compound selected from (C1-1) to (C1-5) and (C2-1) to (C2-2) below:
(C1-1) an α,ω-diene expressed by general formula (2-1):

$$CH_2=CH(CH_2)_xCH=CH_2 \quad (2\text{-}1)$$

wherein $1 \leq x \leq 20$;
(C1-2) an α,ω-diyne expressed by general formula (2-2):

$$CH \equiv C(CH_2)_x C \equiv CH \quad (2\text{-}2)$$

wherein $1 \leq x \leq 20$;
(C1-3) an α,ω-ene-yne expressed by general formula (2-3):

$$CH_2=CH(CH_2)_x C \equiv CH \quad (2\text{-}3)$$

wherein $1 \leq x \leq 20$;
(C1-4) a bisalkenyl polyether compound expressed by general formula (2-4):

$$C_m H_{2m-1} O(C_n H_{2n} O)_y C_m H_{2m-1} \quad (2\text{-}4)$$

wherein $2 \leq m \leq 20$, $2 \leq n \leq 4$, y is a total value of the repetitions of the oxyethylene unit, the oxypropylene unit, and the oxybutylene unit, and $1 \leq y \leq 180$;
(C1-5) an unsaturated group-containing silicone compound expressed by average composition formula (2-5):

$$R^2_p R^3_q SiO_{(4-p-q)/2} \quad (2\text{-}5)$$

wherein $R^2$ may each be independent, but are monovalent organic groups that are different from $R^3$;

$R^3$ are each independently monovalent unsaturated aliphatic hydrocarbon groups having from 2 to 30 carbons, $1.0 \leq p \leq 2.5$, and $0.001 \leq q \leq 1.5$;

(C2-1) an unsaturated epoxy compound expressed by general formula (2-6):

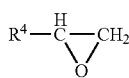
(2-6)

wherein $R^4$ is a substituted or unsubstituted, straight or branched monovalent hydrocarbon group having one reactive unsaturated group and from 2 to 20 carbons; and (C2-2) an unsaturated group-containing cycloaliphatic epoxy compound expressed by general formula (2-7):

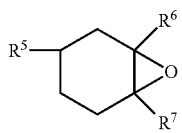
(2-7)

wherein $R^5$ is a substituted or unsubstituted, straight or branched monovalent hydrocarbon group having one reactive unsaturated group and from 2 to 20 carbons, $R^6$ is a hydrogen atom or a methyl group, and $R^7$ is a hydrogen atom or a methyl group.

10. The liquid organopolysiloxane according claim 8, wherein at least one of the monovalent organic group $R^1$ moiety in the average composition formula (1) is (D7) $L^1$, here, $L^1$ is a silylalkyl group having a siloxane dendron structure and, when i=1, is expressed by general formula (3) below:

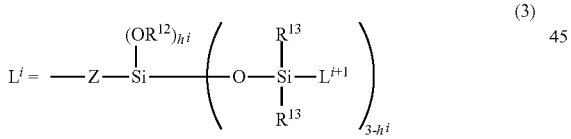
(3)

wherein $R^{12}$ is a substituted or unsubstituted, straight or branched monovalent hydrocarbon group having from 1 to 30 carbons;

$R^{13}$ are each independently a phenyl group or an alkyl group having from 1 to 6 carbons;

Z is a divalent organic group;

i represents a generation of the aforementioned silylalkyl group represented by $L^i$ and is an integer of 1 to k when k is a number of generations that is a number of repetitions of the silylalkyl group; the number of generations k is an integer from 1 to 10; $L^{i+1}$ is the silylalkyl group when i is less than k, and the $R^{13}$ moiety when i=k; and $h^i$ is a number in a range of 0 to 3; and other(s) of the monovalent organic group $R^1$ moiety in the average composition formula (1) is selected from (D1) to (D10) below:

(D1) a substituted or unsubstituted, straight or branched monovalent hydrocarbon group having from 1 to 60 carbons;

(D2) a polyoxyalkylene group expressed by $-R^8O(AO)_z R^9$ wherein AO is an oxyalkylene group having from 2 to 4 carbons, $R^8$ is a substituted or unsubstituted, straight or branched divalent hydrocarbon group having from 3 to 5 carbons, $R^9$ is a hydrogen atom or a substituted or unsubstituted, straight or branched monovalent hydrocarbon group having from 1 to 24 carbons or a substituted or unsubstituted, straight or branched acyl group having from 2 to 24 carbons, and z=1 to 100;

(D3) a substituted or unsubstituted, straight or branched alkoxy group having from 1 to 30 carbons;

(D4) a hydroxyl group;

(D5) an ester group expressed by $-R^{10}-COOR^{11}$ wherein $R^{11}$ is a substituted or unsubstituted, straight or branched divalent hydrocarbon group having from 2 to 20 carbons, and $R^{11}$ is a substituted or unsubstituted, straight or branched monovalent hydrocarbon group having from 1 to 30 carbons;

(D6) an ester group expressed by $-R^{17}-OCOR^{18}$ wherein $R^{17}$ is a substituted or unsubstituted, straight or branched divalent hydrocarbon group having from 2 to 20 carbons, and $R^{18}$ is a substituted or unsubstituted, straight or branched monovalent hydrocarbon group having from 1 to 30 carbons;

(D7) $L^1$, here, $L^1$ is a silylalkyl group having a siloxane dendron structure and, when i=1, is expressed by general formula (3) below:

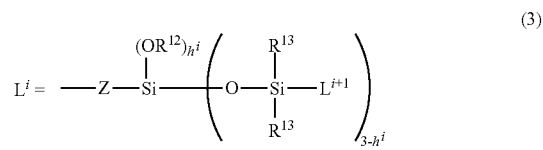
(3)

wherein $R^{12}$ is a substituted or unsubstituted, straight or branched monovalent hydrocarbon group having from 1 to 30 carbons;

$R^{13}$ are each independently a phenyl group or an alkyl group having from 1 to 6 carbons;

Z is a divalent organic group;

i represents a generation of the aforementioned silylalkyl group represented by $L^i$ and is an integer of 1 to k when k is a number of generations that is a number of repetitions of the silylalkyl group; the number of generations k is an integer from 1 to 10; $L^{i+1}$ is the silylalkyl group when i is less than k, and the $R^{13}$ moiety when i=k; and $h^i$ is a number in a range of 0 to 3;

(D8) an alkyl group substituted by a chain polysiloxane structure expressed by general formula (4) below:

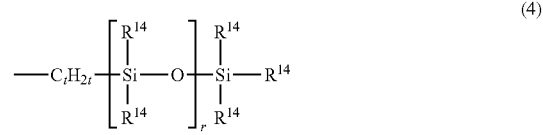
(4)

wherein $R^{14}$ are each independently substituted or unsubstituted, straight or branched monovalent hydrocarbon groups having from 1 to 30 carbons, hydroxyl groups, or hydrogen atoms and at least one of the $R^{14}$ moieties is the monovalent hydrocarbon group; t is a number in a range from 2 to 10; and r is a number in a range from 1 to 100;

(D9) an epoxy group expressed by general formula (5) below:

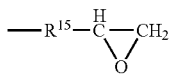

(5)

wherein $R^{15}$ is a substituted or unsubstituted, straight or branched divalent hydrocarbon group having from 2 to 20 carbons; and (D10) a cycloaliphatic epoxy group expressed by general formula (6) below:

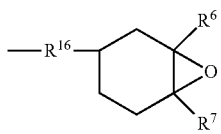

(6)

wherein $R^{16}$ is a substituted or unsubstituted, straight or branched divalent hydrocarbon group having from 2 to 20 carbons, and $R^6$ and $R^7$ are as defined above.

11. A composition comprising the liquid organopolysiloxane described in claim 1, and at least one type of oil agent.

12. An emulsion composition comprising the composition described in claim 11.

13. A raw material for use in an external use preparation or a cosmetic composition comprising the liquid organopolysiloxane described claim 1.

14. The raw material for use in an external use preparation or a cosmetic composition according to claim 13 that is a tactile sensation improver, a film-forming agent, a binder, a viscosity adjuster, a thickening agent, a moisturizing agent, a skin adhesive, a surfactant, an emulsifier, or a powder dispersing agent.

15. An external use preparation or a cosmetic composition comprising the liquid organopolysiloxane described in claim 1.

16. The external use preparation or the cosmetic composition according to claim 15, characterized by not comprising a compound including an oxyalkylene structure where an average value of the number of repetitions of the oxyalkylene unit is two or more.

17. A manufacturing method for the liquid organopolysiloxane described in claim 1, wherein: (A) an organohydrogenpolysiloxane, (B) a glycerin derivative group-containing organic compound having reactive unsaturated group, and (C) at least one type of organic compound selected from the group consisting of (C1) an organic compound having an average number of reactive unsaturated group in the molecule that is greater than 1 and (C2) an organic compound having not less than one reactive unsaturated group and not less than one epoxy group in the molecule are essential components; and each of the components except the component (A) are reacted sequentially with the component (A) in the presence of a hydrosilylation reaction catalyst.

18. The manufacturing method for a liquid organopolysiloxane according to claim 17, wherein in the manufacturing of the liquid organopolysiloxane, the components (A) and (B) are first reacted and, thereafter, crosslinking is conducted by adding the component (C); and an optional component (Q) shown below may be reacted with the component (A) before the reacting of the components (A) and (B), may be further reacted after the reacting of the components (A) and (B), or may be further reacted after the crosslinking by the component (C);

wherein component (Q) is a compound having one reactive unsaturated group in the molecule with the exception of the (C2) compound.

19. The manufacturing method for a liquid organopolysiloxane according to claim 17, wherein in the manufacturing of the liquid organopolysiloxane, the components (A) and (C) that lead to the crosslinking portion are first reacted and, thereafter, the component (B) is added and reacted; and an optional component (Q) shown below may be reacted with the component (A) before the reacting of the components (A) and (C), may be further reacted after the reacting of the components (A) and (C), or may be further reacted after the reacting the component (B):

wherein component (Q) is a compound having one reactive unsaturated group in the molecule with the exception of the (C2) compound.

20. A manufacturing method for a liquid organopolysiloxane or a composition thereof comprising adding at least one type of acidic substance to the liquid organopolysiloxane obtained via the reaction described in claim 17 or a composition including the liquid organopolysiloxane and, thereafter removing volatile components by heating or reducing pressure.

* * * * *